US008578761B2

(12) United States Patent
Fukumura et al.

(10) Patent No.: US 8,578,761 B2
(45) Date of Patent: Nov. 12, 2013

(54) CONCENTRATION SENSOR DEVICE AND CONCENTRATION DETECTING METHOD

(75) Inventors: Kenji Fukumura, Obu (JP); Tetsuo Yoshioka, Okazaki (JP); Tetsuo Fujii, Toyohashi (JP); Takaaki Kawai, Obu (JP); Hirofumi Higuchi, Okazaki (JP); Teruo Oda, Gamagori (JP); Yasuyuki Okuda, Aichi-gun (JP)

(73) Assignee: DENSO CORPORATION, Kariya (JP)

( * ) Notice: Subject to any disclaimer, the term of this patent is extended or adjusted under 35 U.S.C. 154(b) by 878 days.

(21) Appl. No.: 12/733,694

(22) PCT Filed: Mar. 25, 2009

(86) PCT No.: PCT/JP2009/001334
§ 371 (c)(1),
(2), (4) Date: Mar. 16, 2010

(87) PCT Pub. No.: WO2009/119087
PCT Pub. Date: Oct. 1, 2009

(65) Prior Publication Data
US 2010/0235107 A1 Sep. 16, 2010

(30) Foreign Application Priority Data

| Mar. 26, 2008 | (JP) | 2008-080855 |
| Mar. 4, 2009 | (JP) | 2009-051258 |
| Mar. 6, 2009 | (JP) | 2009-054056 |
| Mar. 13, 2009 | (JP) | 2009-061105 |
| Mar. 13, 2009 | (JP) | 2009-061106 |

(51) Int. Cl.
*G01N 33/00* (2006.01)

(52) U.S. Cl.
USPC ....... 73/61.41; 73/61.43; 73/61.45; 73/61.53; 310/313 R; 310/313 A; 310/15

(58) Field of Classification Search
USPC .......... 73/54.43–61.68, 313 R, 313 A, 313 B, 73/19.01, 19.1, 23.2, 23.31, 24.01, 24.04, 73/24.06, 29.01, 335.04, 29.05, 31.05; 310/313 R, 313 A, 313 B
See application file for complete search history.

(56) References Cited

U.S. PATENT DOCUMENTS

| 4,794,323 A * | 12/1988 | Zhou et al. ................... 324/71.5 |
| 4,961,833 A | 10/1990 | Sakai et al. |

(Continued)

FOREIGN PATENT DOCUMENTS

| JP | A-56-148047 | 11/1981 |
| JP | 58-004666 | * 1/1983 |

(Continued)

OTHER PUBLICATIONS

Office Action mailed Jan. 15, 2013 in corresponding JP Application No. 2009-061105 (and English translation).

(Continued)

*Primary Examiner* — Hezron E Williams
*Assistant Examiner* — Hoang Nguyen
(74) *Attorney, Agent, or Firm* — Posz Law Group, PLC

(57) ABSTRACT

A concentration sensor device includes a sensor unit, a substrate, and a sedimentation limit unit. The sensor unit detects a concentration of a specific component contained in liquid. The substrate has a face to which the sensor unit is arranged. The sedimentation limit unit is integrally arranged with the sensor unit or arranged at an upstream side of the sensor unit in a flowing direction of the liquid. The sedimentation limit unit is configured to prevent sedimentation of a foreign object on the sensor unit. The sedimentation limit unit includes a piezoelectric element to vibrate when electricity is supplied so as to promote the foreign object to be separated from the sensor unit. The substrate has a recess recessed in a thickness direction of the substrate.

10 Claims, 23 Drawing Sheets

(56) References Cited

U.S. PATENT DOCUMENTS

| | | | |
|---|---|---|---|
| 5,182,523 A | 1/1993 | Ertel et al. | |
| 5,321,331 A * | 6/1994 | Baer et al. | 310/313 D |
| 5,367,264 A | 11/1994 | Brabetz | |
| 5,589,396 A * | 12/1996 | Frye et al. | 436/73 |
| 6,498,419 B1 * | 12/2002 | Takeuchi et al. | 310/321 |
| 6,781,388 B2 * | 8/2004 | Wang et al. | 324/690 |
| 6,997,037 B2 | 2/2006 | Thurston | |
| 7,168,300 B2 | 1/2007 | Kawanishi et al. | |
| 7,692,432 B2 * | 4/2010 | Yoshida et al. | 324/663 |
| 8,378,694 B2 * | 2/2013 | David et al. | 324/663 |
| 2002/0114125 A1 | 8/2002 | Toyoda et al. | |
| 2002/0141136 A1 | 10/2002 | Toyoda et al. | |
| 2004/0251919 A1 | 12/2004 | Stahlmann et al. | |
| 2005/0116174 A1 * | 6/2005 | Berdermann et al. | 250/370.01 |
| 2005/0161467 A1 | 7/2005 | Jones | |
| 2006/0042940 A1 | 3/2006 | Kawanishi et al. | |
| 2006/0049714 A1 * | 3/2006 | Liu et al. | 310/313 R |
| 2008/0238449 A1 * | 10/2008 | Shizu et al. | 324/689 |
| 2009/0100911 A1 | 4/2009 | Kawanishi et al. | |
| 2009/0157345 A1 | 6/2009 | Yoshioka et al. | |
| 2011/0120219 A1 * | 5/2011 | Barlesi et al. | 73/304 C |

FOREIGN PATENT DOCUMENTS

| | | |
|---|---|---|
| JP | A-61-164144 | 7/1986 |
| JP | A-62-167541 | 7/1987 |
| JP | A-63-309847 | 12/1988 |
| JP | A-03-269560 | 12/1991 |
| JP | Y2-04-032606 | 8/1992 |
| JP | A-59-131154 | 7/1994 |
| JP | B2-H06-79010 | 10/1994 |
| JP | A-08-201326 | 8/1996 |
| JP | B2-2571465 | 10/1996 |
| JP | A-H09-068515 | 3/1997 |
| JP | A-09-138196 | 5/1997 |
| JP | A-2000-009728 | 1/2000 |
| JP | A-2006-308942 | 11/2006 |

OTHER PUBLICATIONS

International Search Report of the International Searching Authority issued on Jun. 23, 2009 in connection with corresponding PCT application No. PCT/JP2009/001334.

Written Opinion of the International Searching Authority issued on Jun. 23, 2009 in connection with corresponding PCT application No. PCT/JP2009/001334.

Office Action mailed Nov. 6, 2012 in corresponding Japanese application No. 2009-61105 (and English translation).

Office Action mailed Nov. 6, 2012 in corresponding Japanese application No. 2009-61106 (and English translation).

* cited by examiner (A)　　　　　　(B)　　　　　　(C)

(A)

(B)

(A)

(B)

(A)

(B)

(C)

MIXTURE FLUID →

CONCENTRATION SENSOR DEVICE AND CONCENTRATION DETECTING METHOD

CROSS REFERENCE TO RELATED APPLICATION

This application is a U.S. national stage of PCT/JP2009/001334 filed on Mar. 25, 2009, and is based on Japanese Patent Application No. 2008-80855 filed on Mar. 26, 2008, Japanese Patent Application No. 2009-51258 filed on Mar. 4, 2009, Japanese Patent Application No. 2009-54056 filed on Mar. 6, 2009, Japanese Patent Application No. 2009-61105filed on Mar. 13, 2009, and Japanese Patent Application No. 2009-61106 filed on Mar. 13, 2009, the disclosures of which are incorporated herein by reference in their entirety.

FIELD OF THE INVENTION

The present invention relates to a concentration sensor device and a concentration detecting method. In particular, the present invention relates to a concentration detecting device, a concentration sensor, device, a mixture ratio calculating device, a concentration detecting method, and a mixture ratio calculating method, so as to detect concentrations or a mixture ratio of mixture fluid.

BACKGROUND ART

A concentration sensor device is widely used for detecting a concentration of a specific component contained in a variety of liquids. For example, recently, use of alcohol-mixed fuel is promoted, in which a biological origin component such as alcohol is mixed in an oil-origin component such as gasoline or light oil. Properties or controls of an internal combustion engine are changed by a mixture ratio between the oil-origin component and the biological origin component. The mixture ratio may correspond to an alcohol concentration. Therefore, the alcohol concentration of the mixture fuel is required to be accurately detected.

Thus, a concentration of a specific component of liquid is required to be accurately detected in a variety of fields, other than the alcohol-mixed fuel. JP-A-5-507561 discloses a concentration sensor device to detect an alcohol concentration of mixture fuel, for example.

The sensor device disclosed in JP-A-5-507561 includes a casing defining a passage through which fuel flows, and a sensor element arranged in the casing. The sensor element is exposed to mixture fuel flowing through the passage, and detects the alcohol concentration by directly contacting the fuel. However, in JP-A-5-507561, the passage defined by the casing has a complicated labyrinth shape, and the sensor element having a large size is arranged in the complicated passage. Therefore, foreign solid object or air bubble contained in the fuel easily adheres onto a detector of the sensor element. As a result, accuracy for detecting the concentration of the specific component contained in fuel may be lowered, due to the adhesion of the foreign object or the bubble.

JP-A-5-87764 discloses a device to measure an alcohol amount (a ratio of alcohol to gasoline) in mixture liquid containing alcohol and gasoline. The device includes an electrode, a sensor element and an electronic measuring circuit. The electrode defines a part of casing through which the mixture liquid flows. The sensor element is arranged in the casing. The electronic measuring circuit evaluates a capacitance of a capacitor defined by the electrode and the sensor element. The electronic measuring circuit detects a permittivity of the mixture liquid based on the capacitance, and calculates a mixture ratio of alcohol to gasoline based on the detected permittivity.

The electrode and the sensor element are located in the mixture liquid so as to detect the capacitance representing the permittivity of the mixture liquid. Foreign objects contained in the mixture liquid may adhere onto the electrode or the sensor element, thereby the capacitance of the capacitor defined by the electrode and the sensor element may be varied. Because a permittivity of the foreign object contained in the mixture liquid is typically larger than that of the mixture liquid, the detected capacitance may be larger than an expected value. When the capacitance of the capacitor is varied by the foreign object, a relative permittivity calculated based on the capacitance is varied, and the mixture ratio of alcohol to gasoline calculated based on the relative permittivity is varied. Thus, accuracy for detecting the mixture ratio of alcohol to gasoline may be lowered.

Recently, alcohol receives attention as an alternative fuel for gasoline. For example, mixture fuel starts to widespread such as a bio-gasoline containing gasoline and ethanol as a main component, or bio-mixed light oil containing light oil and fatty acid methyl ester as a main component. When the mixture fuel is used, concentrations of gasoline and alcohol are timely detected so as to obtain alcohol amount, such that fuel amount suitable for operation state of an internal combustion engine is injected to a combustion chamber. JP-A-5-87764 or JP-A-2008-268169 discloses a concentration detecting device to detect concentrations of gasoline and alcohol.

For example, the detecting device disclosed in JP-A-5-87764 detects alcohol concentration. Mixture fuel (mixture fluid) containing gasoline and alcohol to be measured is introduced between electrodes located in a casing, and a capacitance (permittivity) of the mixture fuel is measured. Further, a liquid properties sensor disclosed in JP-A-2008-268169 detects a mixture ratio of alcohol to gasoline. Comb-teeth shape electrode is arranged on a semiconductor substrate, and the substrate is immersed in liquid fuel such as gasoline, so as to measure a capacitance (permittivity).

However, the mixture fuel may contain water, for example, other than gasoline and ethanol. Specifically, water may be mixed in ethanol in a purification process. Further, water contained in air may melt in the mixture fuel, when the mixture fuel contacts air. Furthermore, water may be mixed in the mixture fuel by human error, when the mixture fuel is transported. When water is mixed into the mixture fuel, the capacitance (permittivity) of the mixture fuel is varied based on concentrations (ratio) of gasoline, ethanol and water. However, the mixture fuel is defined to contain only gasoline an alcohol, and only the concentrations of gasoline and alcohol are measured. Thus, water may generate measurement error.

SUMMARY OF THE INVENTION

In view of the foregoing problems, it is a first object of the present invention to provide a concentration sensor device having a high detection accuracy, in which a foreign object is restricted from adhering onto a sensor part. It is a second object of the present invention to provide a mixture ratio calculating device in which a detection accuracy is restricted from decreasing, and a mixture ratio calculating method using the mixture ratio calculating device. It is a third object of the present invention to provide a concentration detecting method and device, in which concentrations are properly detected in mixture fluid containing three or more components.

According to an example of the present invention, a concentration sensor device includes a sedimentation limit unit. The sedimentation limit unit prevents sedimentation of foreign object on a sensor unit. The sedimentation limit unit is integrally arranged with the sensor unit or arranged at an upstream side of the sensor unit in a flowing direction of liquid. Due to the sedimentation limit unit, the foreign object contained in liquid can be prevented from adhering and accumulating to the sensor unit. Therefore, the sedimentation of foreign object on the sensor unit can be prevented, such that accuracy for detecting a specific component concentration can be raised.

For example, the sedimentation limit unit includes a piezoelectric element. The piezoelectric element vibrates when electricity is supplied. Therefore, when a foreign object adheres onto the sensor unit, the foreign object is promoted to separate from the sensor unit, due to the vibration. Therefore, the sedimentation of foreign object on the sensor unit can be prevented, such that accuracy for detecting a specific component concentration can be raised.

For example, the piezoelectric element is arranged on a face of the substrate opposite from the sensor unit. Therefore, a position of the piezoelectric element is not affected by the sensor unit, and a large area is provided for the piezoelectric element on the face opposite from the sensor unit. Thus, the piezoelectric element can have sufficient vibration area without increasing a size. Further, the sensor unit and the piezoelectric element can be separately formed from each other. Therefore, producing process can be simplified.

For example, a through electrode passes through the substrate so as to connect the piezoelectric element and a circuit unit arranged on the sensor unit side. Therefore, the through electrode is not exposed from the substrate. Thus, the through electrode and mixture fuel are restricted from contacting with each other. As a result, corrosion and damage of the through electrode due to water, for example, contained in the mixture fuel can be reduced. Thus, endurance property of the through electrode can be increased.

For example, the piezoelectric element is arranged on the same face of the substrate as the sensor unit. Therefore, the piezoelectric element can be arranged adjacent to the sensor unit, while securing of vibration area for the piezoelectric element is difficult. Thus, the foreign object adhering on the sensor unit can be promoted to separate from the sensor unit.

For example, the piezoelectric element is arranged between the substrate and the sensor unit. Thus, the piezoelectric element can be arranged in a wide area without being affected by the sensor unit. Further, the piezoelectric element and the sensor unit can be arranged adjacent to each other. Therefore, the vibration area of the piezoelectric element can be secured without increasing the size, and the foreign object adhering on the sensor unit can be promoted to separate from the sensor unit.

For example, the concentration sensor device further has a recess. That is, the substrate has a diaphragm-shaped recess. Therefore, vibration of the sensor unit can be promoted by the piezoelectric element arranged adjacent to the recess. Thus, the foreign object adhering on the sensor unit can be more promoted to separate from the sensor unit.

For example, the piezoelectric element is arranged along the recess located on a face opposite from the sensor unit. Therefore, the whole of the substrate having the diaphragm-shaped recess is vibrated by the piezoelectric element. Thus, the foreign object adhering on the sensor unit can be more promoted to separate from the sensor unit.

For example, an open side of the substrate defining the recess is covered with an insulation film. The piezoelectric element is arranged on a face of the insulation film opposite from the substrate. Therefore, the piezoelectric element makes the insulation film to vibrate. The vibration of the insulation film makes the substrate to vibrate through the recess. Thus, the foreign object adhering on the sensor unit can be promoted to separate from the sensor unit.

For example, an open side of the substrate defining the recess is covered with an insulation film. The sensor unit and the piezoelectric element are arranged on the insulation film. That is, the sensor unit and the piezoelectric element are arranged on the same face of the insulation film. Therefore, when the piezoelectric element makes the insulation film to vibrate, the sensor unit arranged on the insulation film is also vibrated. Thus, the foreign object adhering on the sensor unit can be promoted to separate from the sensor unit.

For example, an open side of the substrate defining the recess is covered with an insulation film. An insulator is layered on a face of the insulation film opposite from the substrate. The piezoelectric element is arranged opposite to the recess through the insulation film, and the sensor unit is arranged to oppose to the piezoelectric element through the insulator. When the piezoelectric element vibrate, the vibration is transmitted to the insulation film and the insulator. That is, the piezoelectric element makes not only the insulation film but also the insulator to vibrate. Therefore, the sensor unit arranged on the insulator can be vibrated. Thus, the foreign object adhering on the sensor unit can be promoted to separate from the sensor unit.

For example, a space is defined between the substrate and the insulation film by the recess, and the space is sealed with gas. The piezoelectric element and the gas resonate with each, when kind or pressure of the gas is controlled, for example. Therefore, the vibration of the piezoelectric element is effectively transmitted toward the sensor unit. Thus, the foreign object adhering on the sensor unit can be promoted to separate from the sensor unit.

For example, the sensor unit has a comb-teeth shaped electrode pattern, and the electrode pattern constructs the piezoelectric element. That is, the electrode pattern corresponds to the sensor unit, and the electrode pattern corresponds to the piezoelectric element. Therefore, self-cleaning can be performed by the vibration of the sensor unit.

For example, an electrode is arranged on a face of the substrate opposite from the sensor unit. Therefore, when a potential difference is applied between the electrode pattern of the piezoelectric element constructing the sensor unit and the electrode, the electrode pattern, that is the sensor unit, vibrates in accordance with the vibration of the substrate. Therefore, self-cleaning can be performed by the vibration of the sensor unit.

For example, the piezoelectric element has an electrode pattern layered on a face of the sensor unit opposite from the substrate. That is, the electrode pattern of the piezoelectric element covers a face of the sensor unit opposite from the substrate. Therefore, the sensor unit is vibrated by the vibration of the electrode pattern of the piezoelectric element. Thus, self-cleaning can be performed by the vibration of the sensor unit.

For example, the piezoelectric element has an electrode pattern layered on a face of the substrate opposite from the sensor unit. That is, the electrode pattern of the piezoelectric element is formed on a face of the substrate opposite from the sensor unit. Therefore, the vibration of the piezoelectric element is transmitted to the sensor unit through the substrate. Thus, the foreign object adhering on the sensor unit can be promoted to separate from the sensor unit.

For example, the piezoelectric element has a first electrode pattern constructing the sensor unit, and a second electrode pattern arranged on a face of the substrate opposite from the sensor unit. Therefore, the sensor unit is vibrated by the vibration of the first electrode pattern, and the sensor unit is vibrated by the vibration of the second electrode pattern transmitted through the substrate. Thus, the foreign object adhering on the sensor unit can be promoted to separate from the sensor unit, and the self-cleaning can be performed by the vibration of the sensor unit.

For example, the piezoelectric element has a first electrode pattern layered on the sensor unit opposite from the piezoelectric element, and a second electrode pattern arranged on a face of the substrate opposite from the sensor unit. Therefore, the sensor unit is vibrated by the vibration of the first electrode pattern, and the sensor unit is vibrated by the vibration of the second electrode pattern transmitted through the substrate. Thus, the foreign object adhering on the sensor unit can be promoted to separate from the sensor unit, and the self-cleaning can be performed by the vibration of the sensor unit.

For example, the sedimentation limit unit is arranged in a liquid passage defined by a passage portion, and has a charge part and a trap part separated from the sensor unit. The charge part applies voltage to liquid flowing through the liquid passage to charge the liquid. Foreign object contained in the liquid is charged together with the liquid. Therefore, the charged object contained in the liquid is trapped by the trap part before arriving at the sensor unit, when the liquid passes through the trap part. Thus, adhesion and sedimentation of the foreign object to the sensor unit can be reduced, such that detection accuracy of the specific component contained in the liquid can be raised.

For example, a wall portion is arranged in the liquid passage. The wall portion separates a flow of the liquid passing through the charge part into the sensor unit or the trap part. The foreign object easily moves toward the trap part. Therefore, the foreign object is difficult to flow into the sensor unit, because the flow of the liquid is separated into the sensor unit or the trap part, due to the wall portion. Thus, adhesion and sedimentation of the foreign object to the sensor unit can be reduced, such that detection accuracy of the specific component contained in the liquid can be raised.

For example, the sedimentation limit unit has an eliminator arranged at a downstream side of the sensor unit. The eliminator removes electricity of the liquid charged by the charge part and the trap part. The charged liquid may electrically affect equipment and device arranged at a downstream side of the sensor unit. Therefore, the eliminator removes electricity of the liquid passing through the sensor unit. Thus, the charged liquid can be restricted from affecting equipment and device arranged at the downstream side of the sensor unit. Accordingly, affecting to outside can be reduced.

For example, a polarity of voltage applied to the charge part is different from that applied to the trap part between positive (+) and negative (−). For example, when the charge part applies positive pressure, the trap part applies negative pressure. The charge part and the trap part maintain their polarity without inversion. That is, when the charge part applies the positive pressure, the charge part maintains the positive pressure, and the trap part maintains the negative pressure. Therefore, the trap of the foreign object charged by the charge part can be achieved by the trap part, such that the foreign object is restricted from moving toward the sensor unit. Thus, adhesion and sedimentation of the foreign object relative to the sensor unit can be reduced, and accuracy for detecting specific component contained in liquid can be increased.

For example, voltage applied to liquid at the charge part and the trap part is alternate voltage equal to or higher than 1 kHz. The maximum value of the negative voltage and the minimum value of the positive voltage are set to be the grounded voltage. When direct voltage or alternate voltage having low frequency is applied to liquid, electrochemical reaction may be generated in the liquid and a variety of components contained in the liquid. Therefore, the alternate voltage equal to or higher than 1 kHz is applied to the charge part and the trap part so as to prevent an irreversible reaction in the liquid. Thus, the liquid is prevented from changing, such that affecting to outside can be reduced.

For example, the trap part has at least one or more board-shaped electrode member. The board-shaped electrode member extends parallel to the axis of the liquid passage, and an upstream side of the electrode member has a width corresponding to a chord in a cross-section perpendicular to the axis of the liquid passage. That is, at the upstream side of the liquid passage, the electrode member has a width extending from an end of the passage portion to the other end of the passage portion. The width of the electrode member is decreased from the upstream side to the downstream side. That is, the width of the electrode portion adjacent to the charge part is large, and the width of the electrode portion adjacent to the sensor unit is small. Therefore, foreign object contained in the liquid passing through the charge part is effectively removed at the upstream side having the large width. Further, because the electrode member extends parallel to the liquid passage, pressure loss of the liquid flowing through the liquid passage can be reduced. Thus, while the pressure loss of the liquid can be reduced, foreign object contained in the liquid can be collected at the upstream side of the sensor unit, such that a concentration detection accuracy of the sensor unit can be made high.

For example, the trap part has one or more board-shaped electrode member. The electrode member extends to be inclined relative to an axis of the liquid passage. The electrode member narrows at least a part of the width of the liquid passage from the upstream side to the downstream side. Therefore, liquid flowing through the liquid passage flows between the electrode members, and a width between the electrode members gradually becomes narrow. Thus, foreign object contained in the liquid is easily collected by the trap part. Accordingly, foreign object contained in liquid can be collected at the upstream side of the sensor unit, such that concentration detection accuracy of the sensor unit can be made higher.

For example, the trap part has at least one or more electrode member, and the electrode member has a tube shape and a cone shape. That is, the trap part has the electrode member having a cone shape or a pyramid shape, for example. An inner diameter of the electrode member is decreased from the upstream side to the downstream side. Therefore, liquid passes through the electrode member, and the inner diameter of the electrode member is gradually decreased. Thus, foreign object contained in the liquid is easily collected by the trap part. Accordingly, foreign object contained in liquid can be collected at the upstream side of the sensor unit, such that concentration detection accuracy of the sensor unit can be made higher.

For example, the trap part has at least one or more electrode member 85, and the electrode member has a tube shape and a cone shape. That is, the trap part has the electrode member having a cone shape or a pyramid shape, for example. The electrode member has a shape in a manner that a flow of the liquid is guided to an inner wall of the passage portion from an upstream side to a downstream side in the liquid passage.

Therefore, the liquid passes through the electrode member to gradually be closer to the inner wall of the passage portion. Thus, foreign object contained in the liquid is easily collected by the trap part, and the pressure loss of the liquid becomes relatively small. Accordingly, foreign object contained in liquid can be collected at the upstream side of the sensor unit, such that concentration detection accuracy of the sensor unit can be made higher.

For example, the concentration sensor device has a vibration providing portion to give vibration to the passage portion. Foreign objects may be accumulated to the charge part and the trap part arranged in the liquid passage after a long time use. The vibration providing portion intermittently vibrates the passage portion defining the liquid passage, such that the charge part and the trap part vibrate together with the passage portion. Thus, sedimentation of the foreign object to the charge part and the trap part can be reduced.

For example, the concentration sensor device includes a protection film to cover the sensor unit. The protection film has a sedimentation limit unit located on an end face of the protection film opposite from the sensor unit. That is, the sensor unit integrally includes the sedimentation limit unit. Therefore, foreign object can be restricted from adhering on the protection film and the protection film covering the sensor unit. Thus, adhesion and sedimentation of foreign objects to the sensor unit can be reduced, such that accuracy for detecting a specific component contained in the liquid can be increased.

For example, a face of the protection film opposite from the sensor unit has a rough face or a convex shape. Therefore, foreign object can be restricted from adhering on the protection film. Thus, adhesion and sedimentation of foreign objects to the sensor unit can be reduced, such that accuracy for detecting a specific component contained in the liquid can be increased.

For example, the protection film has a passage formation part. The passage formation part forms a flow of liquid on a surface of the protection film. Therefore, foreign object adhering on the protection film is removed by the flow of the liquid. The foreign object can be restricted from adhering on the protection film. Thus, adhesion and sedimentation of foreign objects to the sensor unit can be reduced, such that accuracy for detecting a specific component contained in the liquid can be increased.

For example, the protection film is made of a porous member. The porous member has plural holes allowing the liquid to pass through and prohibiting the foreign object to pass through. Therefore, the foreign object is accumulated on the porous member, and does not adhere on the sensor unit. Thus, adhesion and sedimentation of foreign objects to the sensor unit can be reduced, such that accuracy for detecting a specific component contained in the liquid can be increased.

For example, the concentration sensor device includes a vibration providing portion to give vibration to the porous member: When the porous member is used, foreign object contained in the liquid accumulates on the surface of the porous member. Therefore, when the porous member is vibrated by the vibration providing portion, the foreign object accumulated on the porous member can be promoted to separate from the porous member.

According to an example of the present invention, a concentration sensor device includes a piezoelectric element. The piezoelectric element vibrates when electricity is supplied. Therefore, when a foreign object adheres onto the sensor unit, the foreign object is promoted to separate from the sensor unit, due to the vibration. Therefore, the sedimentation of foreign object on the sensor unit can be prevented, such that accuracy for detecting alcohol concentration can be raised.

For example, the piezoelectric element is arranged on a face opposite from the sensor unit through the substrate. Therefore, a position of the piezoelectric element is not affected by the sensor unit, and a large area is provided for the piezoelectric element on the face opposite from the sensor unit. Thus, the piezoelectric element can have sufficient vibration area without increasing a size. Further, the sensor unit and the piezoelectric element can be separately formed from each other. Therefore, producing process can be simplified.

For example, a through electrode passes through the substrate so as to connect the piezoelectric element and a circuit unit arranged on the sensor unit side. Therefore, the through electrode is not exposed from the substrate. Thus, the through electrode and mixture fuel are restricted from contacting with each other. As a result, corrosion and damage of the through electrode due to water, for example, contained in the mixture fuel can be reduced. Thus, endurance property of the through electrode can be increased.

For example, the piezoelectric element is arranged on the same face of the substrate as the sensor unit. Therefore, the piezoelectric element can be arranged adjacent to the sensor unit, while securing of vibration area for the piezoelectric element is difficult. Thus, the foreign object adhering on the sensor unit can be promoted to separate from the sensor unit.

For example, the piezoelectric element is arranged between the substrate and the sensor unit. Thus, the piezoelectric element can be arranged in a wide area without being affected by the sensor unit. Further, the piezoelectric element and the sensor unit can be arranged adjacent to each other. Therefore, the vibration area of the piezoelectric element can be secured without increasing the size, and the foreign object adhering on the sensor unit can be promoted to separate from the sensor unit.

For example, the substrate further has a recess. That is, the substrate has a diaphragm-shaped recess. Therefore, vibration of the sensor unit can be promoted by the piezoelectric element arranged adjacent to the recess. Thus, the foreign object adhering on the sensor unit can be more promoted to separate from the sensor unit.

For example, the piezoelectric element is arranged along the recess located on a face opposite from the sensor unit. Therefore, the whole of the substrate having the diaphragm-shaped recess is vibrated by the piezoelectric element. Thus, the foreign object adhering on the sensor unit can be more promoted to separate from the sensor unit.

For example, an open side of the substrate defining the recess is covered with an insulation film. The piezoelectric element is arranged on a face of the insulation film opposite from the substrate. Therefore, the piezoelectric element makes the insulation film to vibrate. The vibration of the insulation film makes the substrate to vibrate through the recess. Thus, the foreign object adhering on the sensor unit can be promoted to separate from the sensor unit.

For example, an open side of the substrate defining the recess is covered with an insulation film. The sensor unit and the piezoelectric element are arranged on the insulation film. That is, the sensor unit and the piezoelectric element are arranged on the same face of the insulation film. Therefore, when the piezoelectric element makes the insulation film to vibrate, the sensor unit arranged on the insulation film is also vibrated. Thus, the foreign object adhering on the sensor unit can be promoted to separate from the sensor unit.

For example, an open side of the substrate defining the recess is covered with an insulation film. An insulator is layered on a face of the insulation film opposite from the substrate. The piezoelectric element is arranged opposite to the recess through the insulation film, and the sensor unit is arranged to oppose to the piezoelectric element through the insulator. When the piezoelectric element vibrates, the vibration is transmitted to the insulation film and the insulator. That is, the piezoelectric element makes not only the insulation film but also the insulator to vibrate. Therefore, the sensor unit arranged on the insulator can be vibrated. Thus, the foreign object adhering on the sensor unit can be promoted to separate from the sensor unit.

For example, a space is defined between the substrate and the insulation film by the recess, and the space is sealed with gas. The piezoelectric element and the gas resonate with each, when kind or pressure of the gas is controlled, for example. Therefore, the vibration of the piezoelectric element is effectively transmitted toward the sensor unit. Thus, the foreign object adhering on the sensor unit can be promoted to separate from the sensor unit.

For example, the sensor unit has a comb-teeth shaped electrode pattern, and the electrode pattern constructs the piezoelectric element. That is, the electrode pattern corresponds to the sensor unit, and the electrode pattern corresponds to the piezoelectric element. Therefore, self-cleaning can be performed by the vibration of the sensor unit.

For example, the concentration sensor device further includes an electrode arranged on a face of the substrate opposite from the sensor unit. Therefore, when a potential difference is applied between the electrode, pattern of the piezoelectric element constructing the sensor unit and the electrode, the electrode pattern, that is the sensor unit, vibrates in accordance with the vibration of the substrate. Therefore, self-cleaning can be performed by the vibration of the sensor unit.

For example, the piezoelectric element has an electrode pattern layered on a face of the sensor unit opposite from the substrate. That is, the electrode pattern of the piezoelectric element covers a face of the sensor unit opposite from the substrate. Therefore, the sensor unit is vibrated by the vibration of the electrode pattern of the piezoelectric element. Thus, self-cleaning can be performed by the vibration of the sensor unit.

For example, the piezoelectric element has an electrode pattern layered on a face of the substrate opposite from the sensor unit. That is, the electrode pattern of the piezoelectric element is formed on a face of the substrate opposite from the sensor unit. Therefore, the vibration of the piezoelectric element is transmitted to the sensor unit through the substrate. Thus, the foreign object adhering on the sensor unit can be promoted to separate from the sensor unit.

For example, the piezoelectric element has a first electrode pattern constructing the sensor unit, and a second electrode pattern arranged on a face of the substrate opposite from the sensor unit. Therefore, the sensor unit is vibrated by the vibration of the first electrode pattern, and the sensor unit is vibrated by the vibration of the second electrode pattern transmitted through the substrate. Thus, the foreign object adhering on the sensor unit can be promoted to separate from the sensor unit, and the self-cleaning can be performed by the vibration of the sensor unit.

For example, the piezoelectric element has a first electrode pattern layered on the sensor unit opposite from the piezoelectric element, and a second electrode pattern arranged on a face of the substrate opposite from the sensor unit. Therefore, the sensor unit is vibrated by the vibration of the first electrode pattern, and the sensor unit is vibrated by the vibration of the second electrode pattern transmitted through the substrate. Thus, the foreign object adhering on the sensor unit can be promoted to separate from the sensor unit, and the self-cleaning can be performed by the vibration of the sensor unit.

According to an example of the present invention, a mixture ratio calculating device includes a sensor portion and a calculating portion. The sensor portion has a pair of electrodes arranged in mixture liquid, and a detecting circuit to detect a capacitance of a capacitor defined by the pair of electrodes. The calculating portion calculates a mixture ratio of the mixture liquid based on a signal output from the sensor portion. The sensor portion has at least three pairs of electrodes having capacitances different from each other. The calculating portion calculates relative permittivities corresponding to at least three of the detected capacitances contained in the output signal of the sensor portion. The calculating portion calculates a regression line corresponding to at least three of the calculated relative permittivities and the capacitances, or calculates a regression line corresponding to at least three of the calculated relative permittivities and reciprocals of the capacitances. The calculating portion calculates a corrected relative permittivity based on the regression line, and calculates the mixture ratio of the mixture liquid based on the corrected relative permittivity.

The relative permittivity is corrected by calculating the regression line defined between at least three of the capacitances including the permittivities of the mixture liquid to be detected and at least three of the relative permittivities corresponding to the capacitances. Alternatively, the relative permittivity is corrected by calculating the regression line defined between the reciprocals of the capacitances and the relative permittivities. The mixture ratio of the mixture liquid is calculated based on the corrected relative permittivity. That is, the mixture ratio is calculated based on the relative permittivity, in which influence of contaminant adhering on the electrode is eliminated. Therefore, according to the mixture ratio calculating device of the present invention, accuracy for detecting the mixture ratio can be restricted from being lowered.

Parameters used for calculating the relative permittivity of the mixture liquid and the mixture ratio of the mixture liquid are stored in a memory. The memory stores a capacitance of the pair of electrodes in a vacuum state, and the relative permittivities of the components contained in the mixture liquid. In this case, a temperature measuring portion may be included to measure a temperature of the mixture liquid, and the memory may store temperature characteristics of the relative permittivities of the components contained in the mixture liquid. Therefore, the mixture ratio of the mixture liquid can be calculated in accordance with the temperature variation of the mixture liquid.

For example, surface of the pair of electrodes may be covered and protected by a protection film. Thus, the electrode can be restricted from being corroded by the mixture liquid.

For example, the electrode may have a comb-teeth shape. Thus, opposing area between the electrodes can be efficiently increased, compared with a case in which the electrode has a flat board shape. Therefore, a size of the mixture ratio calculating device can be made small.

For example, a comparing step may be performed after a first calculating step is finished. In the comparing step, the three calculated relative permittivities are compared with each other. When at least two of the relative permittivities have the same value in the comparing step, a fifth calculating step is performed to calculate the mixture ratio of the mixture liquid based on the relative permittivities having the same value. When the relative permittivities are different from each other in the comparing step, second, third and fourth calculating steps are performed. When two of the relative permittivies have the same value among at least three relative permittivies calculated in the first calculating step, the two relative permittivities are free from the contaminant. In this case, difference between the two relative permittivities is zero. Therefore, the relative permittivity free from the contaminant can be calculated by performing the comparing step. Thus, the second and third calculating steps can be omitted, when at least two relative permittivities free from the contaminant are calculated. Therefore, a processing speed of the calculating portion can be made fast.

As an example of the present invention, a concentration detecting method detects concentrations of components of mixture fluid, and the mixture fluid is constructed by N (integer≥3) kinds of known components. Permittivities of the mixture fluid are measured at different temperatures of (N−1) points, and the concentrations of the components are calculated based on known permittivies of the components at the different temperatures of (N−1) points and the measured permittivities of the mixture fluid at the different temperatures of (N−1) points.

The concentrations of the components are detected by using a difference between the permittivies of the components and a difference between the temperature characteristics of the permittivities. When the concentrations (contained ratio) of the components are defined as $a_1, a_2, \ldots, a_N$, an equality of $a_1+a_2+\ldots+a_N=1$ is defined. Further, when the permittivities of the mixture fluid are measured at different temperatures of (N−1) points, permittivities $\epsilon_1, \epsilon_2, \ldots, \epsilon_{N-1}$ of (N−1) are obtained. The measured permittivity $\epsilon_1, \epsilon_2, \ldots, \epsilon_{N-1}$ is equal to a sum of multiplications between the known permittivity of the component and the concentration of the component at the same temperature. Therefore, the equalities of (N−1) can be defined. Thus, according to the concentration detecting method for the mixture fluid, simultaneous equation constructed by the equalities of N can be defined relative to unknowns of N of the concentrations $a_1, a_2, \ldots, a_N$. The concentrations $a_1, a_2, \ldots, a_N$ can be properly determined by solving the simultaneous equation.

Thus, the concentration detecting method detects concentrations of components of the mixture fluid constructed by N (integer≥3) kinds of known components. The method can properly detect the concentrations of the mixture fluid containing three or more components.

In the above method, for example, when the N is equal to 3, the components are defined to have concentrations a1, a2, a3, respectively. The two different temperatures are defined to be $T_1, T_2$, respectively. The components are defined to have permittivies $\epsilon_{a1}, \epsilon_{b2}, \epsilon_{c1}$ at the temperature $T_1$, respectively. The components are defined to have permittivities $\epsilon_{a2}, \epsilon_{b2}, \epsilon_{c2}$ at the temperature $T_2$, respectively. The mixture fluid is defined to have permittivies $\epsilon_1, \epsilon_2$ at the temperatures $T_1, T_2$, respectively. In this case, the concentrations a1, a2, a3 of the components can be calculated based on the following formulas.

$$a1+a2+a3=1 \quad \text{(Formula A)}$$

$$\epsilon_1 = \epsilon_{a1} \cdot a1 + \epsilon_{b1} \cdot a2 + \epsilon_{c1} \cdot a3 \quad \text{(Formula B)}$$

$$\epsilon_2 = \epsilon_{a2} \cdot a1 + \epsilon_{b2} \cdot a2 + \epsilon_{c2} \cdot a3 \quad \text{(Formula C)}$$

The above method is suitable for detecting concentrations of mixture fuel for an internal combustion engine in which water has a possibility to be mixed. For example, the components may be constructed by ethanol, gasoline, and water. Gasoline contains hundreds of components having approximately the same permittivity, and the gasoline is defined as a single component. Further, the components may be constructed by fatty acid methyl ester, light oil and water.

In the method, the permittivity of the mixture fluid may be measured based on an output voltage of a C/V converter. Two of capacitance detecting elements are connected in series with each other, and are driven by carrier waves. The wave has a predetermined voltage, and phases of the waves are opposite from each other. Signal output from a connection point between the capacitance detecting elements is input into the C/V converter having a feedback capacitance.

Therefore, influence of a parasitic capacitance generated by the wiring can be cancelled. Thus, the permittivity can be more accurately measured, compared with a case in which a single capacitance detecting element is used, and the concentrations of the components can be more accurately detected.

As an example of the present invention, the concentration detecting method may be performed by a concentration detecting device.

The device detects concentrations of components contained in mixture fluid containing N (integer≥3) kinds of know components. The device includes a temperature measuring portion, a permittivity measuring portion and a concentration calculating portion. The temperature measuring portion measures temperatures of the mixture fluid at different points of (N−1). The permittivity measuring portion measures permittivities of the mixture fluid at the different temperatures of (N−1) points. Known permittivities of the components at the different temperatures of (N−1) points are stored in a memory. The concentration calculating portion calculates concentrations of the components based on the known permittivities stored in the memory and the measured permittivities of the mixture fluid at the different temperatures of (N−1) points.

Thus, the concentration detecting method can be conducted for the mixture fluid.

The concentration detecting device may further include a heater to form the different temperature of (N−1) points.

The temperature of the mixture fluid is changed by time passage, such that the permittivities of the mixture fluid are measured at the different temperatures of (N−1) points. However, when the device includes the heater, the temperature of the mixture fluid can be changed in a short time. Thus, the device can detect the concentrations of the components.

In the device, a temperature detecting element of the temperature measuring portion, and a capacitance detecting element of the permittivity measuring portion may be arranged on a single chip. Therefore, size reduction and cost reduction are performed compared with a case in which a temperature detecting element and a capacitance detecting element are separately arranged in a pipe through which the mixture fluid flows.

Further, when the device includes the heater, a temperature detecting element of the temperature measuring portion, a capacitance detecting element of the permittivity measuring portion, and a heater element of the heater may be arranged on a single chip. Thus, size reduction and cost reduction are performed.

In this case, the chip may have a groove to thermally separate the heater element from the temperature detecting element and the permittivity detecting element. Thus, heat can be restricted from conducting from the heater element to the temperature detecting element and the permittivity detecting element through the chip. In this case, the temperature and the permittivity can be properly measured, compared with a case in which the groove is not defined in the chip. Therefore, the concentrations of the components can be more accurately detected.

When the capacitance detecting element is formed on the chip, the capacitance detecting element may be made of a pair of comb-teeth electrodes. Thus, the mixture fluid can be easily introduced between the pair of comb-teeth electrodes arranged on the sensor chip. Further, a value of the detected capacitance can be increased by raising comb-teeth density, such that accuracy for measuring the permittivity can be raised.

Further, when the device includes the heater, an agitating portion to agitate mixture fluid may be arranged between the heater element and a set of the temperature detecting element and the capacitance detecting element. The heater element is arranged at an upstream side of mixture fluid, and the temperature detecting element and the capacitance detecting element are arranged at a downstream side of mixture fluid.

The agitating portion may be a fin, mesh or filter, and temperature variation of mixture fluid generated by using the heater element can be eliminated by the agitating portion. Thus, the temperature and the permittivity can be properly measured. Therefore, the concentrations of the components can be more properly measured. Especially, when the capacitance detecting element having the large electrode dimension is used, the temperature of mixture fluid between the electrodes is required to be made uniform by using the agitating portion, because a volume of the mixture fluid between the electrodes is large.

In the device, the capacitance detecting element of the permittivity measuring portion may be made of a pair of electrodes. One of the electrodes may further operate as the temperature detecting element of the temperature Measuring portion. Thus, size reduction and cost reduction can be performed.

In the device, the permittivity of the mixture fluid may be measured based on an output voltage of a C/V converter. Two of capacitance detecting elements are connected in series with each other, and are driven by carrier waves. The wave has a predetermined voltage, and phases of, the waves are opposite from each other. Signal output from a connection point between the capacitance detecting elements is input into the C/V converter having a feedback capacitance.

Therefore, influence of a parasitic capacitance generated by the wiring can be cancelled. Thus, the permittivity can be more accurately measured, compared with a case in which a single capacitance detecting element is used, and the concentrations of the components can be more accurately detected.

In the method, for example, when the N is equal to 3, the components are defined to have concentrations a1, a2, a3, respectively. The two different temperatures are defined to be $T_1$, $T_2$, respectively. The components are defined to have permittivies $\epsilon_{a1}$, $\epsilon_{b1}$, $\epsilon_{c1}$ at the temperature $T_1$, respectively. The components are defined to have permittivies $\epsilon_{a2}$, $\epsilon_{b2}$, $\epsilon_{c2}$ at the temperature $T_2$, respectively. The mixture fluid is defined to have permittivies $\epsilon_1$, $\epsilon_2$ at the temperatures $T_1$, $T_2$, respectively. In this case, the concentrations of the components can be calculated based on the following formulas.

$$a1+a2+a3=1 \quad \text{(Formula A)}$$

$$\epsilon_1 = \epsilon_{a1} \cdot a1 + \epsilon_{b1} \cdot a2 + \epsilon_{c1} \cdot a3 \quad \text{(Formula B)}$$

$$\epsilon_2 = \epsilon_{a2} \cdot a1 + \epsilon_{b2} \cdot a2 + \epsilon_{c2} \cdot a3 \quad \text{(Formula C)}$$

The device can be used for detecting concentrations of mixture fuel having a possibility to accidentally contain water, when the mixture fuel is used for an internal combustion engine. For example, the components are constructed by ethanol, gasoline and water, or the components are constructed by fatty acid methyl ester, light oil and water.

Thus, the concentration detecting method and device detect concentrations of components of mixture fluid containing N (integer≥3) kinds known components. The concentration detecting method and device can properly detect the concentrations of mixture fluid containing three or more components.

DETAILED DESCRIPTION OF PREFERRED EMBODIMENT

Embodiments are described with reference to drawings. Substantially the same construction part has the same reference number among the embodiments, and description of the same construction part is omitted. A concentration sensor device to be described below detects a concentration of a bio-origin alcohol contained in mixture fuel, as a specific component contained in liquid, for example.

(First Embodiment)

Figure 1:
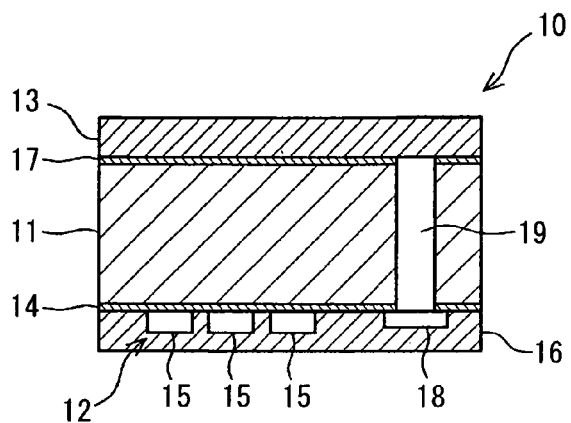
FIG. 1 is a schematic cross-sectional view illustrating a concentration sensor device according to a first embodiment of the present invention.
Figure 2:
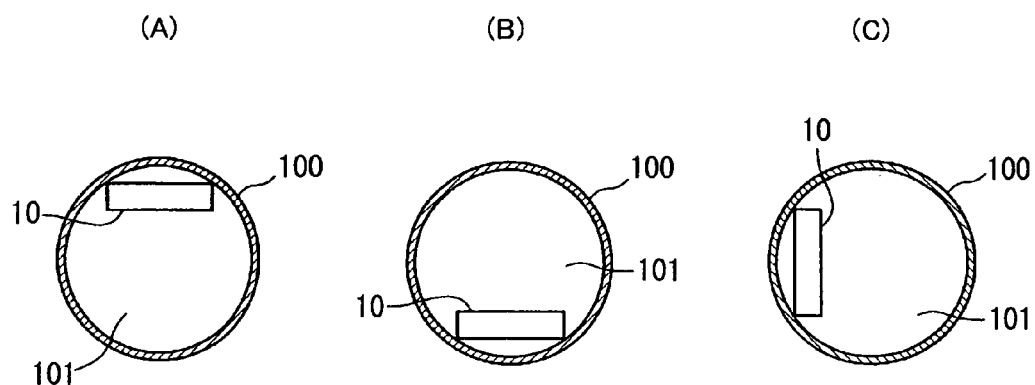
FIG. 2 is a view illustrating arrangement positions of the concentration sensor device to a pipe portion.

FIG. 1 shows a concentration sensor device according to a first embodiment. As shown in FIG. 1, a concentration sensor device 10 of the first embodiment includes a substrate 11, a sensor unit 12 and a piezoelectric element 13. The substrate 11 is made of a silicon semiconductor, for example. As shown in FIG. 2, the concentration sensor device 10 is arranged in a pipe portion 100 through which mixture fuel flows. The concentration sensor device 10 is arranged to an upper part shown in FIG. 2(A), a bottom part shown in FIG. 2(B), or a side part shown in FIG. 2(C) of the pipe portion 100.

As shown in FIG. 1, the sensor unit 12 is arranged on a first face of the substrate 11. An insulation film 14 is arranged between the sensor unit 12 and the substrate 11. The insulation film 14 is a silicon oxide film, for example. The sensor unit 12 has plural electrodes 15. For example, a permittivity and a relative permittivity between the electrodes 15 of the sensor unit 12 are changed by a concentration of alcohol contained in the mixture fuel. The sensor unit 12 detects the permittivity and the relative permittivity between the electrodes 15, thereby a concentration of alcohol contained in the mixture fuel is detected. That is, a mixture ratio between an oil-origin fuel and a bio-origin fuel is detected. The sensor unit 12 has a known construction, thereby a specific description of the construction is omitted. The sensor unit 12 is protected by a protection film 16. The protection film 16 is made of silicon nitride film, for example. The sensor unit 12 may electrically detect the concentration based on a capacitance and an impedance between the electrodes 15. Further, the concentration of the specific component contained in liquid may be optically detected based on a light refractive index and a translucency of light having a predetermined wavelength, for example. In the first embodiment, the sensor unit 12 detects the concentration of the specific component contained in liquid based on the permittivity between the electrodes 15.

The piezoelectric element 13 is arranged on a second face of the substrate 11 opposite from the sensor unit 12. An insulation film 17 is arranged between the piezoelectric element 13 and the substrate 11. The insulation film 17 is silicon oxide film, for example. The piezoelectric element 13 has a non-illustrated construction sandwiching a piezoelectric member between electrodes. The piezoelectric element 13 vibrates when electricity is supplied.

The concentration sensor device 10 includes a circuit unit 18. The circuit unit 18 is arranged on the first face of the substrate with the sensor unit 12. The circuit unit 18 has a non-illustrated process circuit and connection pad, for example. The process circuit processes a signal output from the sensor unit 12 and a signal input into the piezoelectric element 13, for example. A bonding wire connecting the concentration sensor device 10 and outside connection terminal is connected to the connection pad. The circuit unit 18 is arranged on the same face as the sensor unit 12, and is arranged adjacent to the sensor unit 12. The circuit unit 18 is protected by the protection film 16 made of the silicon nitride film, similar to the sensor unit 12.

The piezoelectric element 13 is electrically connected to the circuit unit 18 by a through electrode 19 passing through the substrate 11. The piezoelectric element 13 vibrates based on a signal from the circuit unit 18. The piezoelectric element 13 and the circuit unit 18 are connected by the through electrode 19, thereby the through electrode 19 is not exposed to outside of the substrate 11. As shown in FIG. 2, the concentration sensor device 10 is arranged inside of a fuel passage 101 defined in the pipe portion 100. Therefore, the concentration sensor device 10 is exposed to mixture fuel flowing through the fuel passage 101. The mixture fuel containing alcohol easily contains metal-corrosive component such as water. As shown in FIG. 1, the through electrode 19 is arranged in the substrate 11, thereby the through electrode 19 is difficult to contact the fuel. Therefore, even when the concentration sensor device 10 is exposed to the mixture fuel, corrosion and wearing of the through electrode 19 can be decreased, such that endurance of the through electrode 19 can be improved.

In the first embodiment, when the piezoelectric element 13 is vibrated by electricity, the substrate 11 and the sensor unit 12 are also vibrated, because the substrate 11 and the sensor unit 12 are integrated with the piezoelectric element 13. Therefore, when foreign objects of the mixture fuel adhere on the sensor unit 12 exposed to the mixture fuel, the foreign objects are promoted to be separated from the sensor unit 12, due to the vibration of the sensor unit 12 generated in accordance with the vibration of the piezoelectric element 13. Thus, adhesion of the foreign objects to the sensor unit 12 can be reduced, such that detection accuracy for the alcohol concentration contained in the mixture fuel can be increased. Further, a frequency for separating the foreign objects may be set in a manner that a wavelength is equal to or lower than a size of the foreign objects. For example, a wavelength of the vibration of the piezoelectric element 13 for separating the foreign objects is set to be equal to or smaller than a dimension of the foreign object.

In the first embodiment, the piezoelectric element 13 is arranged on the second face of the substrate 11 opposite from the sensor unit 12. Therefore, a location of the piezoelectric element 13 is not restricted by the sensor unit 12, and a location of the sensor unit 12 is not restricted by the piezoelectric element 13. Thus, a location area of the piezoelectric element 13 can be sufficiently secured. Accordingly, a vibration area of the piezoelectric element 13 can be secured without increasing a size of the concentration sensor device 10. Further, each of the sensor unit 12 and the piezoelectric element 13 can be produced in a process independent from each other. Therefore, the producing process can be made simple.

Further, in the first embodiment, the through electrode 19 connecting the piezoelectric element 13 and the circuit unit 18 passes through the substrate 11. Therefore, the through electrode 19 is difficult to be exposed to the mixture fuel containing water, for example. Thus, corrosion and damage of the through electrode 19 can be reduced, such that endurance of the through electrode 19 can be increased.

(Second and Third Embodiments)

Figure 3:
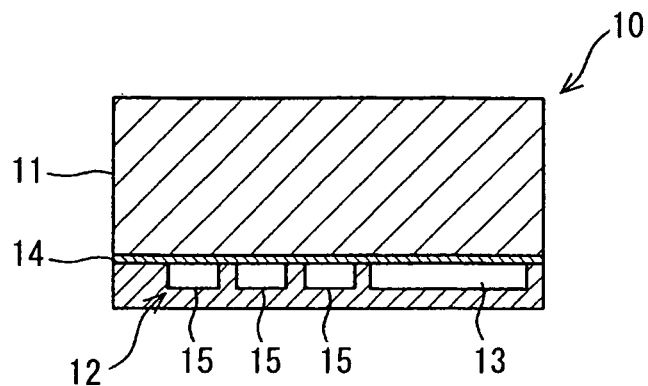
FIG. 3 is a schematic cross-sectional view illustrating a concentration sensor device according to a second embodiment.
Figure 4:
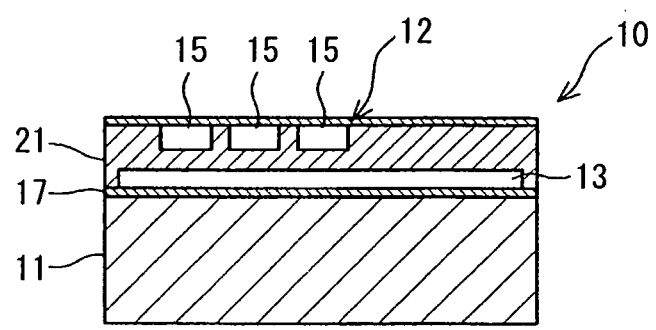
FIG. 4 is a schematic cross-sectional view illustrating a concentration sensor device according to a third embodiment.

A concentration sensor device according to a second embodiment is shown in FIG. 3, and a concentration sensor device according to a third embodiment is shown in FIG. 4.

In the second embodiment, as shown in FIG. 3, the sensor unit 12 and the piezoelectric element 13 are arranged on the same face of the substrate 11. In a case that the sensor unit 12 and the piezoelectric element 13 are arranged on the same face of the substrate 11, a size of the device 10 may be increased to secure a location area for the sensor unit 12 and the piezoelectric element 13. If the size of the device is maintained without the increasing, a vibration area of the piezoelectric element 13 may be decreased. In contrast, when the sensor unit 12 and the piezoelectric element 13 are arranged on the same face of the substrate 11, the sensor unit 12 and the piezoelectric element 13 are arranged adjacent to each other. Thus, because the sensor unit 12 directly vibrates due to the vibration of the piezoelectric element 13, the separation of the foreign objects can be more promoted.

In the third embodiment, as shown in FIG. 4, the device 10 has an insulator layer 21 arranged on a face of the substrate 11 through the insulation film 17. The insulation film 17 is made of silicon oxide film, and the insulator layer 21 is made of silicon nitride film. The piezoelectric element 13 is arranged on a face of the insulation film 17 opposite from the substrate 11. The insulator layer 21 covers the piezoelectric element 13 arranged on the insulation film 17. The sensor unit 12 is arranged on a face of the insulator layer 21 opposite from the substrate 11. Thus, the piezoelectric element 13 is arranged between the substrate 11 and the sensor unit 12.

In the third embodiment, because the piezoelectric element 13 is arranged between the substrate 11 and the sensor unit 12, locations of the piezoelectric element 13 and the sensor unit 12 are not affected by each other. Further, because the piezoelectric element 13 is arranged between the substrate 11 and the sensor unit 12, the sensor unit 12 and the piezoelectric element 13 are arranged adjacent to each other. Therefore, while a process for forming the sensor unit 12 and the piezoelectric element 13 may become complicated, a vibration area of the piezoelectric element 13 can be secured, and the sensor unit 12 and the piezoelectric element 13 can be arranged adjacent to each other.

(Fourth Embodiment)

Figure 5:
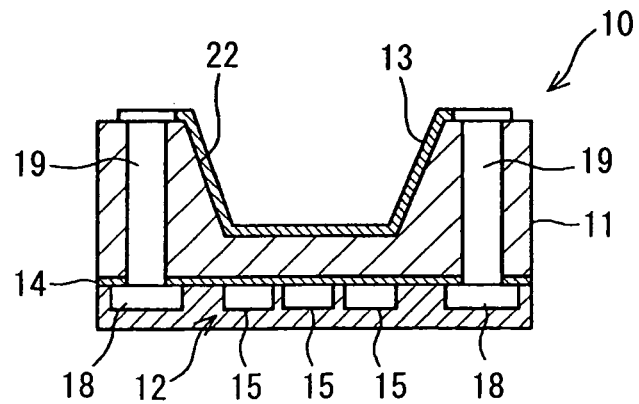
FIG. 5 is a schematic cross-sectional view illustrating a concentration sensor device according to a fourth embodiment.

FIG. 5 shows a concentration sensor device according to a fourth embodiment.

As shown in FIG. 5, a concentration sensor device 10 according to the fourth embodiment has a recess 22 defined in the substrate 11. The recess 22 has a diaphragm shape recessed from a first face of the substrate 11 toward a second face of the substrate 11 opposite from the first face. The sensor unit 12 and the circuit unit 18 are arranged on a flat face of the substrate 11 opposite from the recess 22. The piezoelectric element 13 is arranged along an open end face of the recess 22, thereby the piezoelectric element 13 covers an open face of the recess 22 of the substrate 11. Thus, the piezoelectric element 13 is arranged opposite from the sensor unit 12 and the circuit unit 18 through the substrate 11.

The device 10 includes the through electrode 19 passing through the substrate 11 in the thickness direction. A first end of the through electrode 19 is connected to the circuit unit 18, and a second end of the through electrode 19 is connected to the piezoelectric element 13. Therefore, the piezoelectric element 13 is electrically connected to the circuit unit 18 through the through electrode 19.

In the fourth embodiment, because the piezoelectric element 13 is arranged along the recess 22, a distance between the piezoelectric element 13 and the sensor unit 12 is reduced. Further, because the substrate 11 has a diaphragm shape due to the recess 22, and because the substrate 11 is vibrated by the piezoelectric element 13, the sensor unit 12 arranged on the substrate 11 can be more promoted to vibrate. Thus, the separation of the foreign objects adhering on the sensor unit 12 can be more promoted.

(Fifth Embodiment)

Figure 6:
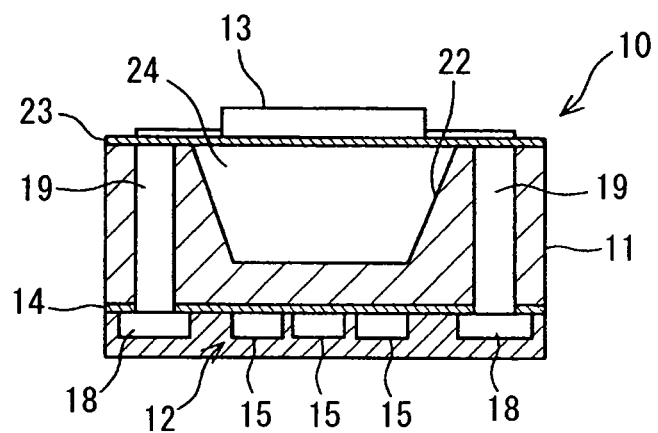
FIG. 6 is a schematic cross-sectional view illustrating a concentration sensor device according to a fifth embodiment.

FIG. 6 shows a concentration sensor device according to a fifth embodiment.

As shown in FIG. 6, a concentration sensor device 10 according to the fifth embodiment has the recess 22 defined in the substrate 11. The recess 22 has a diaphragm shape recessed from a first face of the substrate 11 toward a second face of the substrate 11 opposite from the first face. The sensor unit 12 and the circuit unit 18 are arranged on a flat face of the substrate 11 opposite from the recess 22. Further, the device 10 includes an insulation film 23 to close an open side of the recess 22 of the substrate 11. An end of the open side of the recess 22 is closed by the insulation film 23. The insulation film 23 is made of silicon oxide film, for example.

The piezoelectric element 13 is arranged on a face of the insulation film 23 opposite from the substrate 11. Therefore, the piezoelectric element 13 is arranged opposite from the sensor unit 12 and the circuit unit 18 through the substrate 11. The piezoelectric element 13 is connected to the circuit unit 18 by the through electrode 19 passing through the substrate 11. Because an open side of the recess 22 is covered by the insulation film 23, a space 24 is defined between the substrate 11 and the insulation film 23. The space 24 is filled with gas such as nitrogen or air.

In the fifth embodiment, because the recess 22 defined in the substrate 11 is closed by the insulation film 23, the space 24 is defined between the substrate 11 and the insulation film 23. The space 24 is filled with gas such as nitrogen or air. The eigen-frequency of the gas in the space 24 is varied by changing a kind, a pressure and an amount of the gas. Therefore, when the eigen-frequency of the gas and a frequency of the piezoelectric element 13 are made approximately equal to each other, the gas in the space 24 resonates with the piezoelectric element 13. Thus, the vibration of the piezoelectric element 13 is transmitted to the sensor unit 12 located opposite from the piezoelectric element 13 through the substrate 11, due to the resonance of the gas in the space 24. Accordingly, even when the substrate 11 is arranged between the piezoelectric element 13 and the sensor unit 12, the vibration of the sensor unit 12 can be promoted so as to promote the separation of the foreign object from the sensor unit 12.

(Sixth, Seventh and Eighth Embodiments)

Figure 7:
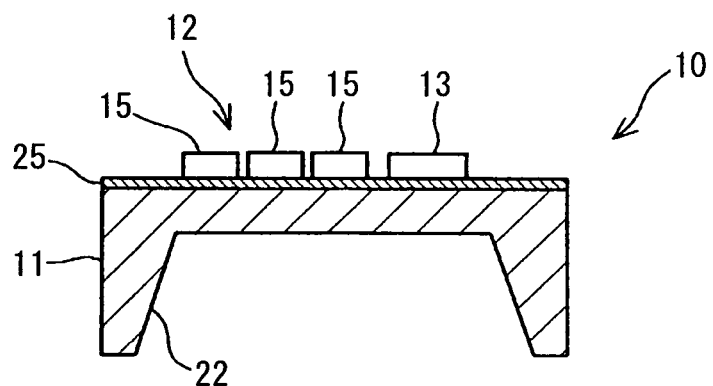
FIG. 7 is a schematic cross-sectional view illustrating a concentration sensor device according to a sixth embodiment.
Figure 8:
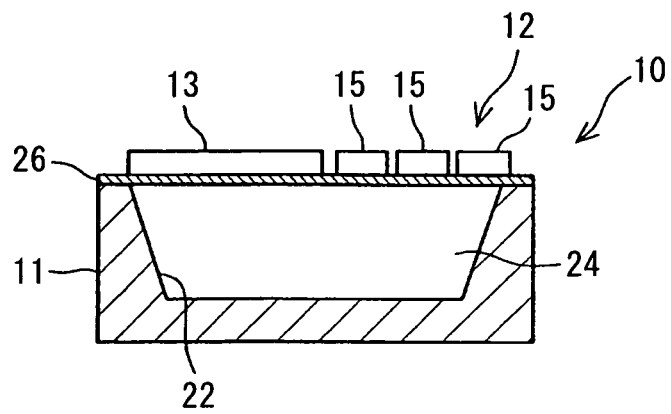
FIG. 8 is a schematic cross-sectional view illustrating a concentration sensor device according to a seventh embodiment.
Figure 9:
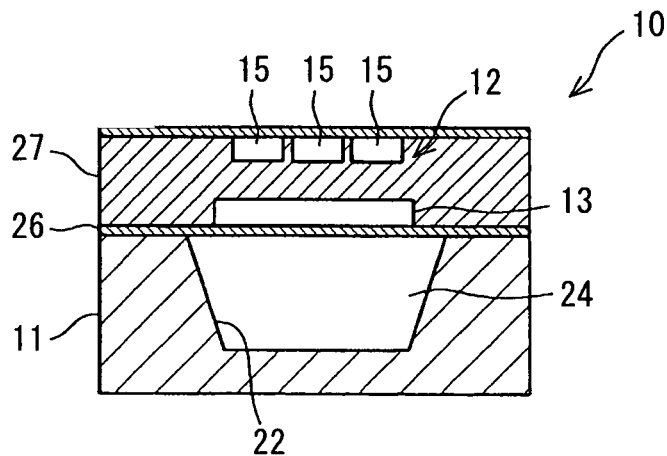
FIG. 9 is a schematic cross-sectional view illustrating a concentration sensor device according to an eighth embodiment.

Concentration sensor devices according to a sixth, a seventh and an eighth embodiment are shown in FIG. 7, FIG. 8 and FIG. 9, respectively.

In the sixth embodiment, as shown in FIG. 7, the sensor unit 12 and the piezoelectric element 13 are arranged on a flat face of the substrate 11. That is, in the sixth embodiment, the sensor unit 12 and the piezoelectric element 13 are arranged on the same side of the substrate 11. An insulation film 25 made of silicon oxide film is arranged between the substrate 11 and a set of the sensor unit 12 and the piezoelectric element 13. When the piezoelectric element 13 vibrates, the vibration is transmitted to the sensor unit 12 through the substrate 11, in which a thickness of the substrate 11 is decreased by the recess 22. Therefore, the vibration of the sensor unit 12 can be promoted, such that the separation of the foreign object can be promoted.

In the seventh embodiment, as shown in FIG. 8, an insulation film 26 made of silicon oxide film closes the recess 22, and the sensor unit 12 and the piezoelectric element 13 are arranged on a face of the insulation film 26 opposite from the substrate 11. That is, in the seventh embodiment, the sensor unit 12 and the piezoelectric element 13 are arranged on the same side of the substrate 11. Therefore, when the piezoelectric element 13 vibrates, the vibration is transmitted to the sensor unit 12 through the insulation film 26. Thus, the vibration of the sensor unit 12 can be promoted, such that the separation of the foreign object can be promoted.

In the eighth embodiment, as shown in FIG. 9, an insulator layer 27 made of silicon nitride film is arranged on a face of the insulation film 26 opposite from the substrate 11. The sensor unit 12 is arranged on a face of the insulator layer 27 opposite from the substrate 11. The piezoelectric element 13 is arranged on the face of the insulation film 26 opposite from the substrate 11. That is, the piezoelectric element 13 is arranged between the substrate 11 and the sensor unit 12. Therefore, when the piezoelectric element 13 vibrates, the vibration is transmitted to the sensor unit 12 through the insulator layer 27 layered on the insulation film 26. Thus, the vibration of the sensor unit 12 can be promoted, such that the separation of the foreign object can be promoted.

(Ninth Embodiment)

Figure 10:
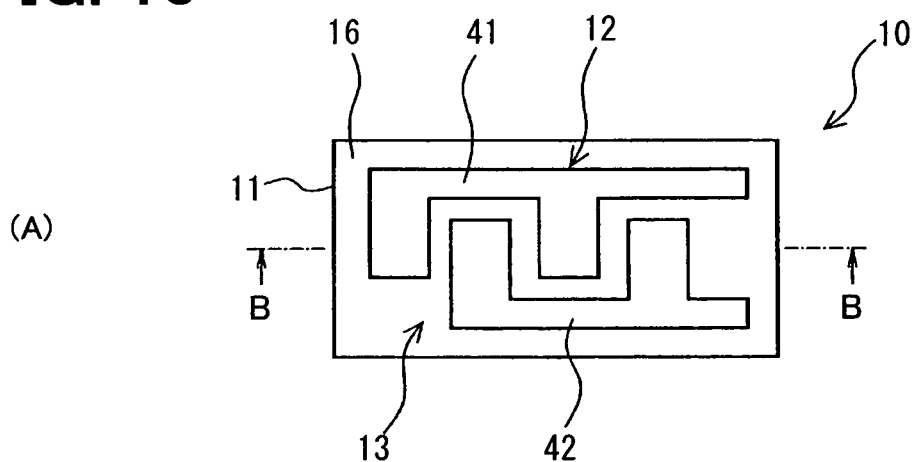
FIG. 10(A) is a schematic plan view illustrating a concentration sensor device according to a ninth embodiment.
FIG. 10(B) is a cross-sectional view taken alone line B-B of FIG. 10(A)
Figure 10:
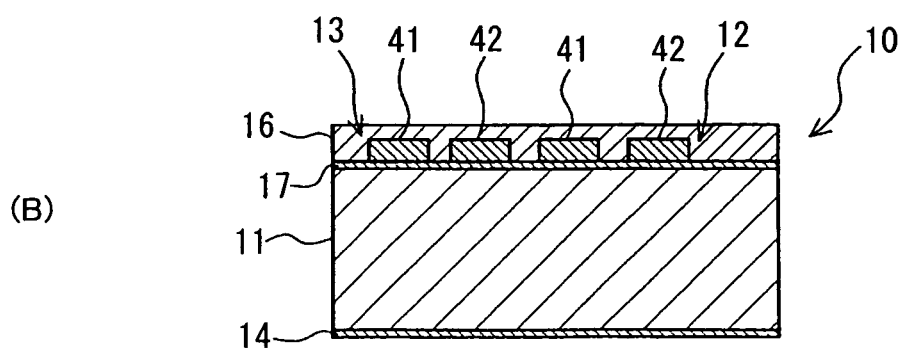

FIG. 10 shows a concentration sensor device according to a ninth embodiment.

In the ninth embodiment, as shown in FIG. 10, a concentration sensor device 10 includes the substrate 11 and the sensor unit 12. As shown in FIG. 10(B), the insulation film 14 is arranged on an end face of the substrate 11 opposite from the sensor unit 12, and the insulation film 17 is arranged between the substrate 11 and the sensor unit 12. As shown in FIG. 10(A), the sensor unit 12 has plural electrode patterns 41, 42. The electrode patterns 41, 42 have comb-teeth shapes opposing to each other. The sensor unit 12 detects alcohol concentration contained in mixture fuel by detecting a permittivity and a relative permittivity between the electrode patterns 41, 42 opposing to each other. The electrode patterns 41, 42 of the sensor unit 12 are protected by the protection film 16.

In the ninth embodiment, the electrode pattern 41, 42 is made of a piezoelectric element having a comb-teeth shape. That is, the electrode pattern 41, 42 is formed into the comb-teeth shape by evaporating a piezoelectric material such as PZT and by sputtering AgPd, for example. The electrode pattern 41, 42 is electrically connected to a non-illustrated circuit unit. Therefore, a predetermined voltage is applied to the electrode pattern 41, 42 from the circuit unit. A space between the electrode patterns 41, 42 is distorted by applying the voltage between the electrode patterns 41, 42. When voltage to generate a predetermined vibration pattern is applied between the electrode patterns 41, 42 from the circuit unit, vibration is generated, and the vibration is parallel to a sensor face of the sensor unit 12 and perpendicular to a thickness direction of the substrate 11. That is, in the ninth embodiment, the electrode pattern 41, 42 of the sensor unit 12 represents both of the sensor unit 12 to measure a permittivity of fuel and the piezoelectric element 13 to define a sedimentation limit unit.

The circuit unit performs a time-division operation between a measurement of permittivity of fuel and a generating a vibration by supplying electricity to the sensor unit 12.

That is, the circuit unit switches voltage pattern applied to the electrode pattern 41, 42 between when measuring the permittivity of fuel and when making the sensor unit 12 to vibrate as the piezoelectric element 13.

In the ninth embodiment, the comb-teeth shaped electrode, pattern 41, 42 constructing the sensor unit 12 represents both of the sensor unit 12 and the piezoelectric element 13. That is, the sensor unit 12 and the piezoelectric element 13 are integrated with each other. Therefore, self-cleaning can be performed relative to the sensor unit 12 by self-vibration, such that removal of foreign object can be promoted from the sensor unit 12 and the protection film 16 protecting the sensor unit 12. A surface of the protection film 16 may be flat and smooth, or concave and rough between the electrode patterns 41, 42. In a case that the surface of the protection film 16 is made rough, vibration between the electrode patterns 41, 42 generates a distortion of the protection film 16. Thus, foreign object adhering in a concave defined in the rough surface can be removed by the distortion of the protection film 16.

(Tenth Embodiment)

Figure 11:
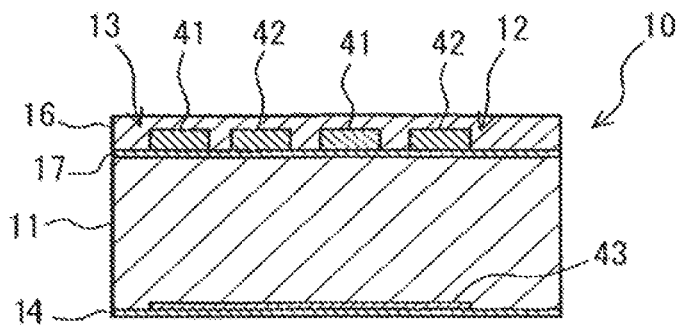
FIG. 11 is a schematic cross-sectional view illustrating a concentration sensor device according to a tenth embodiment, the view corresponding to FIG. 10(B)

FIG. 11 shows a concentration sensor device according to a tenth embodiment. The tenth embodiment is a modification of the ninth embodiment, and the modified difference will be described.

In the tenth embodiment, as shown in FIG. 11, a concentration sensor device 10 includes an electrode 43 arranged on a face of the substrate 11 opposite from the sensor unit 12. The electrode 43 and the end face of the substrate 11 opposite from the sensor unit 12 are covered with the insulation film 14. The electrode pattern 41, 42 constructing the sensor unit 12 has a structure similar to the ninth embodiment.

The electrode 43 is electrically connected to a non-illustrated circuit unit together with the electrode pattern 41, 42. Therefore, the predetermined voltage is applied between the electrode pattern 41, 42 and the electrode 43. A compression wave is generated between the electrode pattern 41, 42 and the electrode 43 in a thickness direction of the substrate 11 by applying the predetermined voltage between the electrode pattern 41, 42 and the electrode 43. When voltage to generate a predetermined vibration pattern is applied between the electrode pattern 41, 42 and the electrode 43 from the circuit unit, vibration is generated in the thickness direction of the substrate 11. The circuit unit sets a polarity of the electrode 43 to be negative (−), for example, and switches a polarity of the electrode pattern 41, 42 to be positive (+) or negative (−). Therefore, vibration is generated between the electrode pattern 41, 42 and the electrode 43 in the thickness direction of the substrate 11.

In the tenth embodiment, the electrode 43 is arranged on the substrate 11 opposite from the sensor unit 12. Therefore, when potential difference is provided between the electrode 43 and the electrode pattern 41, 42 of the piezoelectric element constructing the sensor unit 12, the electrode pattern 41, 42 vibrates. That is, the sensor unit 12 vibrates together with the substrate 11. Thus, self-cleaning of the sensor unit 12 can be performed by self-vibration. Further, when the voltage pattern applied between the electrode 43 and the electrode pattern 41, 42 is changed, the vibration generated in the thickness direction of the substrate 11 can be combined to the vibration parallel to the sensor unit 12 between the electrode patterns 41, 42.

(Eleventh Embodiment)

Figure 12:
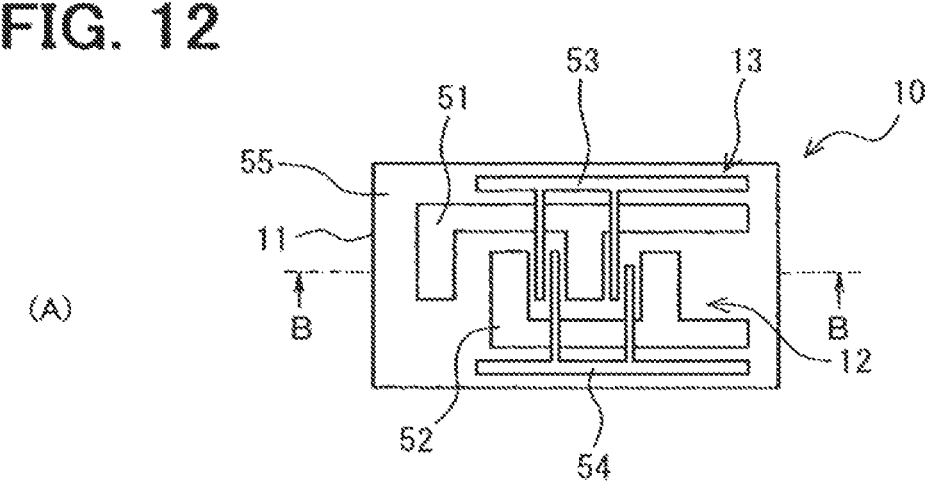
FIG. 12(A) is a schematic plan view illustrating a concentration sensor device according to an eleventh embodiment.
FIG. 12(B) is a cross-sectional view taken alone line B-B of FIG. 12(A)
Figure 12:
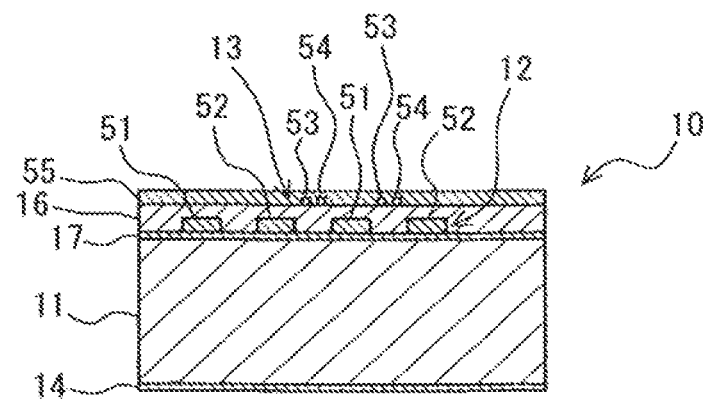

FIG. 12 shows a concentration sensor device according to an eleventh embodiment.

In the eleventh embodiment, as shown in FIG. 12, a concentration sensor device 10 includes the substrate 11, the sensor unit 12 and the piezoelectric element 13. As shown in FIG. 12(B), the insulation film 14 is arranged on an end face of the substrate 11 opposite from the sensor unit 12, and the insulation film 17 is arranged between the substrate 11 and the sensor unit 12. As shown in FIG. 12(A), the sensor unit 12 has plural electrodes 51, 52. The electrodes 51, 52 are arranged to oppose to each other. As shown in FIG. 12(A), the electrode 51, 52 has a comb-teeth shape. The sensor unit 12 detects alcohol concentration contained in mixture fuel by detecting a permittivity and a relative permittivity between the electrodes 51, 52. The electrodes 51, 52 of the sensor unit 12 are protected by the protection film 16.

In the eleventh embodiment, the piezoelectric element 13 corresponding to a sedimentation limit unit is arranged on a face of the protection film 16 protecting the sensor unit 12 opposite from the substrate 11. Specifically, the piezoelectric element 13 has electrode patterns 53, 54 made of a piezoelectric element. The electrode patterns 53, 54 are arranged on the protection film 16 opposite from the substrate 11. Therefore, the electrode patterns 53, 54 constructing the piezoelectric element 13 are layered on the protection film 16 protecting the sensor unit 12. The electrode patterns 53, 54 are protected by a protection film 55.

The electrode patterns 53, 54 are made of piezoelectric element having comb-teeth shape. The electrode patterns 53, 54 are electrically connected to a non-illustrated circuit unit. Therefore, a predetermined voltage is applied to the electrode patterns 53, 54 from the circuit unit. A space between the electrode patterns 53, 54 is distorted by applying the voltage between the electrode patterns 53, 54, and vibration is generated. The vibration is parallel to a sensor face of the sensor unit 12 and perpendicular to a thickness direction of the substrate 11.

In the eleventh embodiment, the piezoelectric element 13 has the electrode patterns 53, 54 layered on a side of the sensor unit 12 opposite from the substrate 11. That is, a face of the sensor unit 12 opposite from the substrate 11 is covered by the electrode patterns 53, 54 of the piezoelectric element 13. Therefore, when vibration is generated by the electrode patterns 53, 54 of the piezoelectric element 13, the sensor unit 12 is also vibrated. Thus, self-cleaning of the sensor unit 12 can be performed by self-vibration.

(Twelfth Embodiment)

Figure 13:
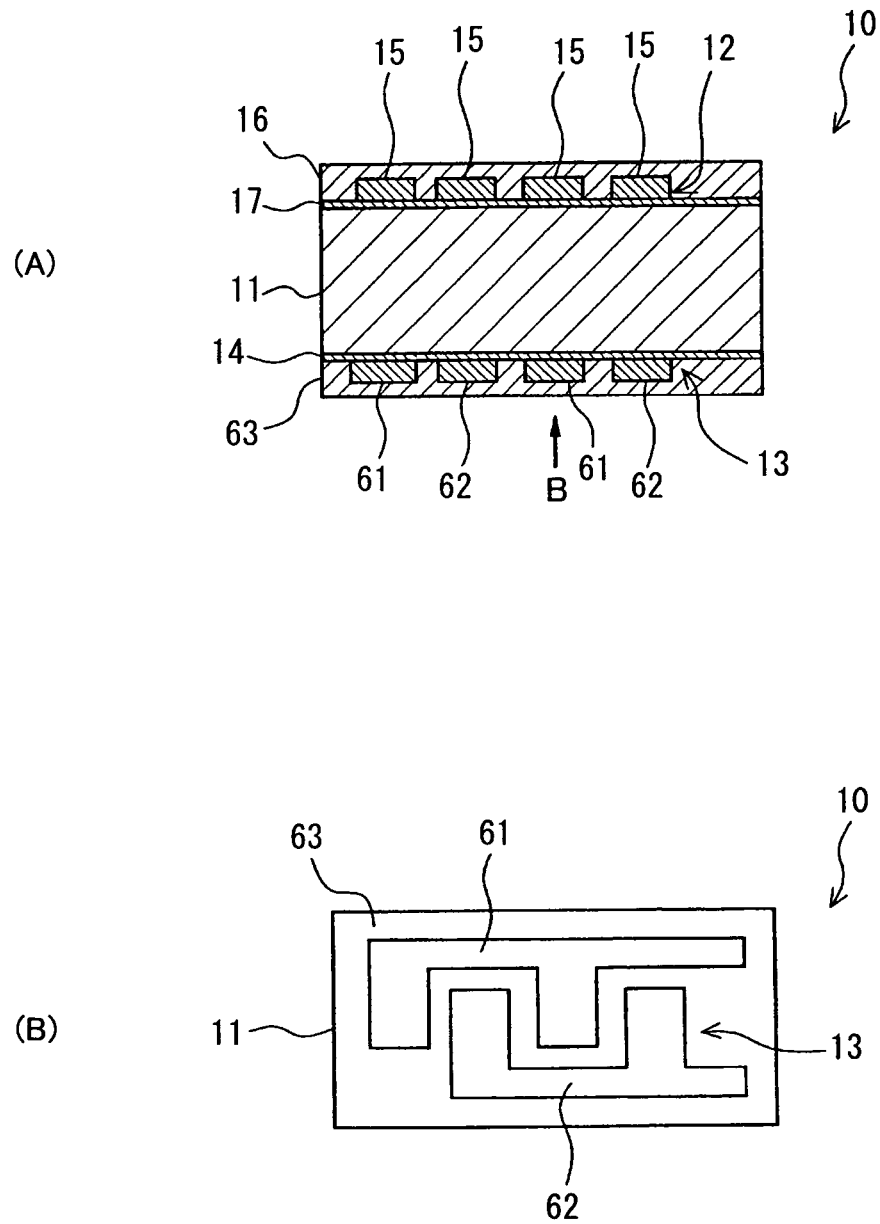
FIG. 13(A) is a cross-sectional view illustrating a concentration sensor device according to a twelfth embodiment, the view corresponding to FIG. 10(B)
FIG. 13(B) is a schematic plan view taken in an arrow direction B of FIG. 13(A)

FIG. 13 shows a concentration sensor device according to a twelfth embodiment.

In the twelfth embodiment, as shown in FIG. 13, a concentration sensor device 10 includes the substrate 11, the sensor unit 12 and the piezoelectric element 13. As shown in FIG. 13(B), the insulation film 14 is arranged on an end face of the substrate 11 opposite from the sensor unit 12, and the insulation film 17 is arranged between the substrate 11 and the sensor unit 12. As shown in FIG. 13(A), the sensor unit 12 has plural electrodes 15. The electrodes 15 have structure similar to the first embodiment.

In the twelfth embodiment, the piezoelectric element 13 is arranged on a face of the substrate 11 opposite from the sensor unit 12. Specifically, the piezoelectric element 13 corresponding to a sedimentation limit unit has electrode patterns 61, 62 made of piezoelectric element. The electrode patterns 61, 62 are arranged on the substrate 11 opposite from the sensor unit 12. The electrode patterns 61, 62 are protected by a protection film 63.

The electrode patterns 61, 62 are made of piezoelectric element having comb-teeth shape. The electrode patterns 61, 62 are electrically connected to a non-illustrated circuit unit. Therefore, a predetermined voltage is applied to the electrode patterns 61, 62 from the circuit unit. A space between the electrode patterns 61, 62 is distorted by applying the voltage between the electrode patterns 61, 62. The distortion becomes compression wave transmitted in the thickness direction of the substrate 11 so as to vibrate the sensor unit 12.

In the twelfth embodiment, the piezoelectric element 13 has the electrode patterns 61, 62 on a face of the substrate 11 opposite from the sensor unit 12. That is, the substrate 11 has the electrode patterns 61, 62 of the piezoelectric element 13 on a face opposite from the sensor unit 12. Therefore, vibration of the piezoelectric element 13 is transmitted to the sensor unit 12 through the substrate 11. Thus, separation of foreign object adhering to the sensor unit 12 can be promoted.

The ninth embodiment and the twelfth embodiment may be combined with each other. That is, in the concentration sensor device 10 of the ninth embodiment, the sensor unit 12 having the comb-teeth electrode pattern 41, 42 corresponding to a first electrode pattern is arranged on a first face of the substrate 11, and the comb-teeth electrode pattern 61, 62 corresponding to a second electrode pattern is arranged on a second face of the substrate 11. The piezoelectric element 13 is constructed by the electrode pattern 41, 42 defining the sensor unit 12, and the electrode pattern 61, 62 arranged opposite from the sensor unit 12. Therefore, the sensor unit 12 vibrates due to the electrode pattern 41, 42, and vibrates due to vibration of the electrode pattern 61, 62 transmitted through the substrate 11. Thus, the sensor unit 12 vibrates in plural directions. Accordingly, separation of foreign object adhering to the sensor unit 12 can be promoted, and self-cleaning of the sensor unit 12 can be performed by self-vibration.

The eleventh embodiment and the twelfth embodiment may be combined with each other. That is, in the concentration sensor device 10 of the eleventh embodiment, the comb-teeth electrode pattern 53, 54 corresponding to a first electrode pattern is layered on the sensor unit 12, and the comb-teeth electrode pattern 61, 62 corresponding to a second electrode pattern is arranged on a face of the substrate 11 opposite from the sensor unit 12. The piezoelectric element 13 is constructed by the electrode pattern 53, 54 covering the sensor unit 12, and the electrode pattern 61, 62 arranged opposite from the sensor unit 12. Therefore, the sensor unit 12 vibrates due to the electrode pattern 53, 54, and vibrates due to vibration of the electrode pattern 61, 62 transmitted through the substrate 11. Thus, the sensor unit 12 vibrates in plural directions. Accordingly, separation of foreign object adhering to the sensor unit 12 can be promoted, and self-cleaning of the sensor unit 12 can be performed by self-vibration.

(Thirteenth Embodiment)

Figure 14:
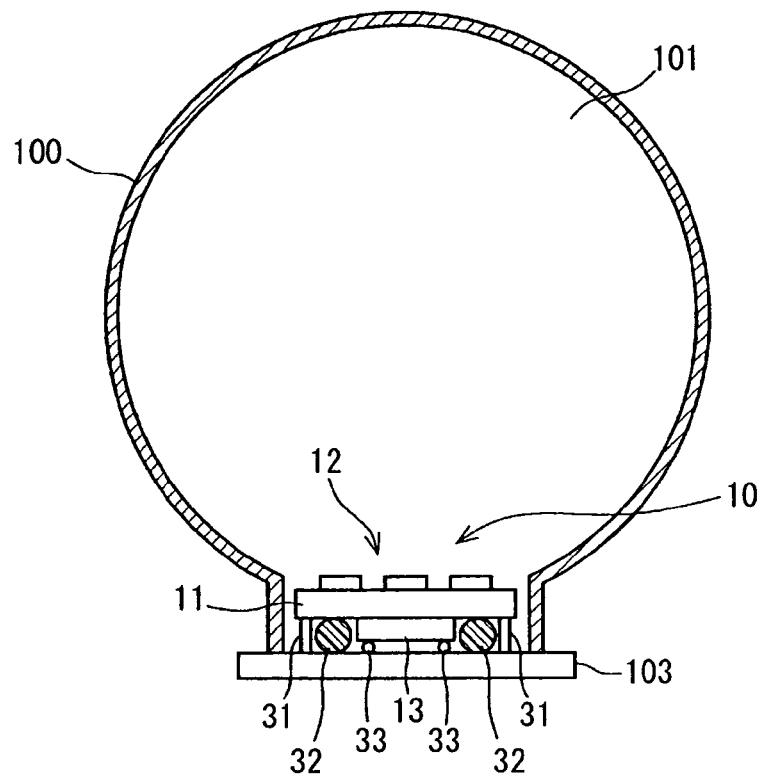
FIG. 14 is a schematic view illustrating arrangement position of a concentration sensor device according to a thirteenth embodiment to a pipe portion.

FIG. 14 shows a concentration sensor device according to a thirteenth embodiment.

In the thirteenth embodiment, as shown in FIG. 14, a concentration sensor device 10 is arranged in a pipe portion 100 having an aperture. In this case, a mount substrate 103 is arranged outside of the pipe portion 100, and is used for mounting the device 10. A rib 31 and a seal 32 are arranged between the device 10 and the mount substrate 103. Mixture fuel is prevented from flowing toward inside of the rib 31 and the seal 32. The mount substrate 103 and the device 10 are electrically connected by a solder ball 33 or boding wire, for example. Further, in a case shown in FIG. 14, the piezoelectric element 13 of the device 10 is directly and electrically connected to the mount substrate 103 by the solder ball 33, for example, without passing through the circuit unit of the substrate 11. When the rib 31 and the seal 32 are arranged between the device 10 and the mount substrate 103, mixture fuel is prevented from flowing toward inside of the solder ball 33 and the bonding wire. Therefore, corrosion and damage of the solder ball 33 and the boding wire can be prevented.

(Fourteenth Embodiment)

Figure 15:
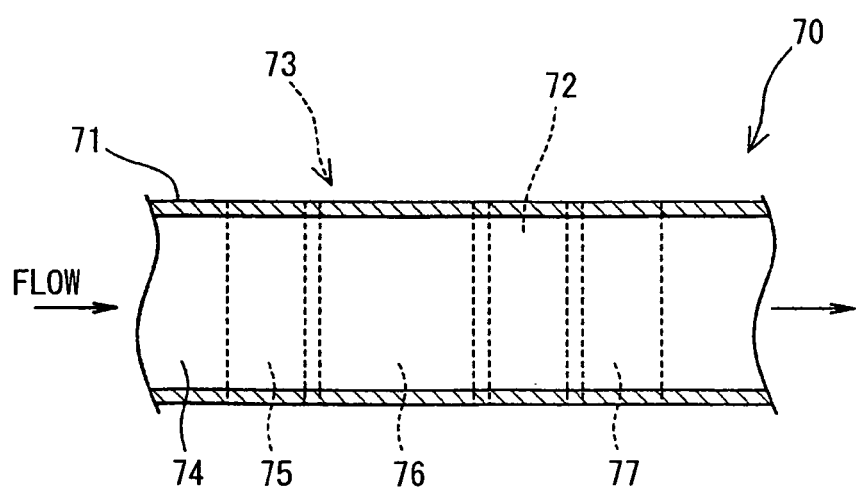
FIG. 15 is a schematic view illustrating a concentration sensor device according to a fourteenth embodiment.

FIG. 15 shows a concentration sensor device according to a fourteenth embodiment.

In the fourteenth embodiment, as shown in FIG. 15, a concentration sensor device 70 includes a passage portion 71, a sensor unit 72 and a sedimentation limit unit 73. The passage portion 71 has a tube shape, and defines a fuel passage 74 as a liquid passage through which mixture fuel flows. The mixture fuel flows in the fuel passage 74 from left corresponding to an upstream side to right corresponding to a downstream side in FIG. 15. The sensor unit 72 has a non-illustrated substrate, and a non-illustrated electrode arranged on the substrate, similarly to the above embodiments.

The sedimentation limit unit 73 has a charge part 75 and a trap part 76 at an upstream side of the sensor unit 72 in a flowing direction of fuel in the fuel passage 74. The charge part 75 applies voltage to the mixture fuel flowing through the fuel passage 74. The charge part 75 has a mesh shape made of conductive metal, for example. The charge part 75 charges the mixture fuel flowing through fuel passage 74 with electricity. The trap part 76 is arranged between the charge part 75 and the sensor unit 72. The trap part 76 is arranged at an upstream side of the sensor unit 72, and is arranged at a downstream side of the charge part 75. The trap part 76 collects foreign object contained in the mixture fuel charged by the charge part 75.

Figure 16:
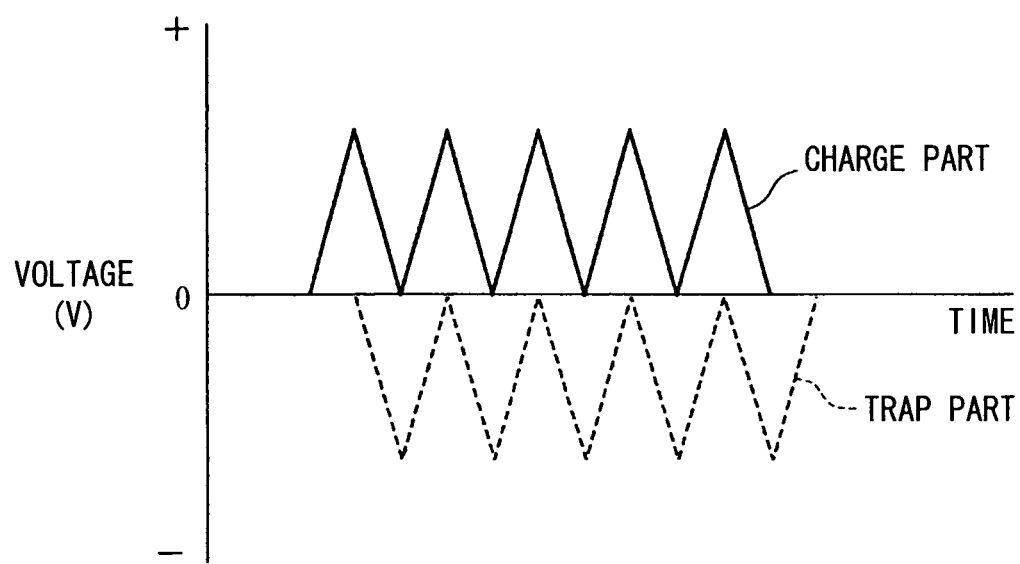
FIG. 16 is a diagram illustrating a variation of voltage applied to a charge part and a trap part in the fourteenth embodiment.

As shown in FIG. 16, alternate voltage equal to or higher than 1 kHz is applied to the charge part 75 and the trap part 76. Polarities of the voltages applied to the charge part 75 and the trap part 76 are different from each other. For example, when the charge part 75 is positively (+) charged, the trap part 76 is negatively (−) charged. Further, when the charge part 75 is positively (+) charged, the charge part 75 maintains the positive voltage without inverting to a negative voltage. Similarly, when the trap part 76 is negatively (−) charged, the trap part 76 maintains the negative voltage without inverting to a positive voltage. Thus, the charge part 75 and the trap part 76 maintain positive or negative polarity. When the charge part 75 is positively charged, the minimum value of the voltage is 0V to be a grounded voltage. Similarly, when the trap part 76 is negatively charged, the maximum value of the voltage is 0V.

In the fourteenth embodiment, the charge part 75 and the trap part 76 are arranged at the upstream side of the sensor unit 72, and the polarities of the charge part 75 and the trap part 76 are different from each other. Therefore, mixture fuel flowing through the fuel passage 74 is positively charged, when passing through the charge part 75, because the positive voltage is applied. Thus, a foreign object contained in the mixture fuel is positively charged. The mixture fuel containing the positively-charged foreign object passes through the trap part 76 after passing through the charge part 75. Because the negative voltage having a polarity opposite from the charge part 75 is applied to the trap part 76, the positively-charged foreign object is collected by the trap part 76. Thus, the foreign object contained in the mixture fuel is collected by the trap part 76, so as to be restricted from flowing into the sensor unit 12.

When mixture fuel passes through the charge part 75 and the trap part 76, the mixture fuel is positively or negatively charged. The charged mixture fuel may electrically affect non-illustrated equipment arranged at a downstream side of the device 70. As shown in FIG. 15, the sedimentation limit unit 73 has an eliminator 77 to remove electricity, and the eliminator 77 is located at the downstream side of the sensor unit 72 in the flowing direction of mixture fuel. The eliminator 77 has a mesh shape made of conductive metal, for example. Electricity charged on mixture fuel can be removed when the charged mixture fuel passes through the eliminator 77.

In the fourteenth embodiment, the sedimentation limit unit 73 disposed in the fuel passage 74 defined by the passage portion 71 includes the charge part 75 and the trap part 76, which are separated from the sensor unit 72. Mixture fuel flowing through the fuel passage 74, and foreign object contained in the mixture fuel are charged when the charge part 75 applies voltage. When the mixture fuel passes through the trap part 76, the foreign object contained in the mixture fuel is collected before passing through the sensor unit 72. Therefore, adhesion and sedimentation of the foreign object relative to the sensor unit 72 can be reduced. Thus, accuracy for detecting specific component contained in mixture fuel can be increased.

Further, in the fourteenth embodiment, the sedimentation limit unit 73 has the eliminator 77 at the downstream side of the sensor unit 72. Electricity of the mixture fuel charged by the charge part 75 and the trap part 76 is removed by the eliminator 77. The charged mixture fuel may electrically affect equipment and device arranged at a downstream side of the sensor unit 72. Therefore, the eliminator 77 removes electricity of the mixture fuel passing through the sensor unit 72. Thus, the mixture fuel can be restricted from affecting equipment and device arranged at the downstream side of the sensor unit 72. Accordingly, influence to outside can be reduced.

In the fourteenth embodiment, a polarity of voltage applied to the charge part 75 is different from that applied to the trap part 76. The charge part 75 and the trap part 76 maintain their polarity without inversion. Therefore, the trap of the foreign object charged by the charge part 75 can be achieved by the trap part 76, such that the foreign object is restricted from moving toward the sensor unit 72. Thus, adhesion and sedimentation of the foreign object relative to the sensor unit 72 can be reduced, and accuracy for detecting specific component contained in mixture fuel can be increased.

In the fourteenth embodiment, voltage applied to mixture fuel at the charge part 75 and the trap part 76 is alternate voltage equal to or higher than 1 kHz. The maximum value of the negative voltage and the minimum value of the positive voltage are set to be the grounded voltage. When direct voltage or alternate voltage having low frequency is applied to mixture fuel, electrochemical reaction may be generated in the mixture fuel and a variety of components contained in the mixture fuel. Therefore, the alternate voltage equal to or higher than 1 kHz is applied to the charge part 75 and the trap part 76 so as to prevent an irreversible reaction in the mixture fuel. Thus, components of the mixture fuel are prevented from changing, such that influence to outside can be reduced.

The polarities of the charge part 75 and the trap part 76 are different from each other. When the charge part 75 is negatively charged, the trap part 76 is positively charged.

(Fifteenth Embodiment)

Figure 17:
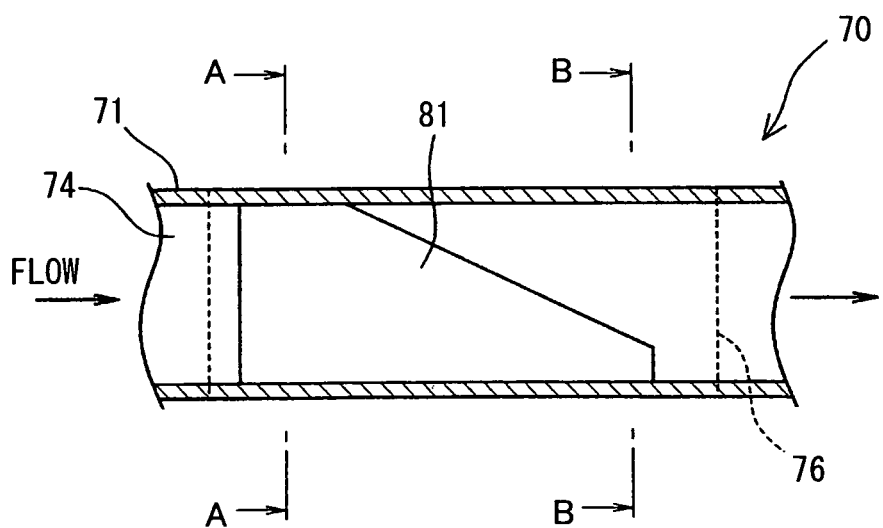
FIG. 17 is a schematic view illustrating a concentration sensor device according to a fifteenth embodiment.

FIG. 17 shows a concentration sensor device according to a fifteenth embodiment.

In the fifteenth embodiment, as shown in FIG. 17, the trap part 76 of the concentration sensor device 70 includes an electrode member 81 extending parallel to an axis of the fuel passage 74. The electrode member 81 has a board shape, and at least one or more of the electrode member 81 is arranged in the fuel passage 74. A width of the electrode member 81 is decreased from the upstream side to the downstream side in the flowing direction of fuel in the fuel passage 74. Here, the width of the electrode member 81 represents a length in a chord direction of the passage portion 71 defining the fuel passage 74.

Figure 18:
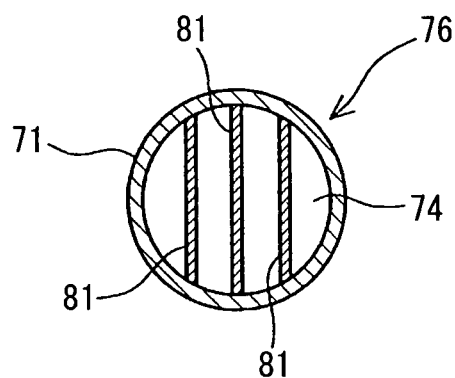
FIG. 18(A) is a cross-sectional view taken along line A-A of FIG. 17.
FIG. 18(B) is a cross-sectional view taken along line B-B of FIG. 17.

As shown in FIG. 18(A), at an upstream side of the fuel passage 74, the electrode member 81 has a width corresponding to a chord of the passage portion 71. That is, the electrode member 81 stands up from a first inner wall of the passage portion 71 so as to be perpendicular to the flowing direction of fuel, and extends to a second inner wall opposing to the first inner wall. Therefore, the electrode member 81 has the width corresponding to the chord of the passage portion 71, at an upstream side of the fuel passage 74. In contrast, as shown in FIG. 18(B), at a downstream side of the fuel passage 74, the width of the electrode member 81 is decreased. That is, an end of the electrode member 81 does not extend to the second inner wall opposing to the first inner wall, while the electrode member 81 stands up from the first inner wall of the passage portion 71 so as to be perpendicular to the flowing direction of fuel. Thus, the width of the electrode member 81 is set to be larger at the upstream side, and is set to be smaller at the downstream side.

Figure 19:
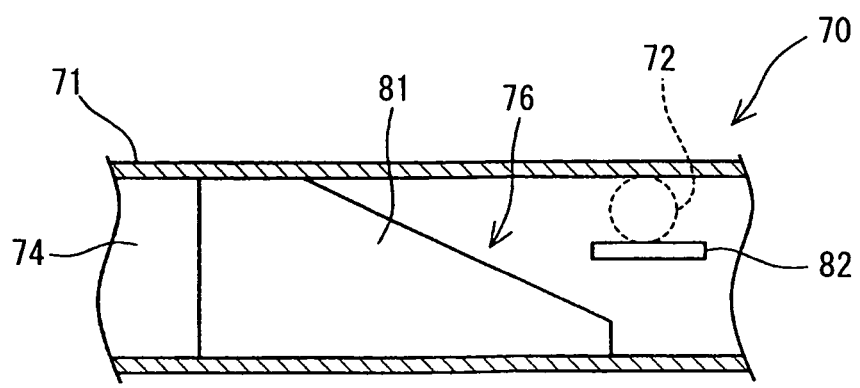
FIG. 19 is a schematic view illustrating a concentration sensor device according to a fifteenth embodiment.

As shown in FIG. 19, the device 70 may include a wall member 82. The wall member 82 separates a flow of mixture fuel passing through the charge part 75 into the sensor unit 72 or the trap part 76. That is, the wall member 82 is arranged between the sensor unit 72 and the trap part 76 in the fuel passage 74 so as to branch the flow of mixture fuel. Foreign object of the mixture fuel charged by passing through the charge part 75 is collected by the electrode member 81 of the trap part 76. The width of the electrode member 81 is set to become smaller toward the downstream side. Therefore, when the electrode member 81 of FIG. 19 is used, the foreign object contained in the mixture fuel easily moves downward of FIG. 19 along the electrode member 81. The wall member 82 is located above a downstream end of the electrode member 81 of FIG. 19, thereby mixture fuel containing foreign objects flows under the wall member 82. Thus, mixture fuel containing little foreign object flows above the wall member 82, and the sensor unit 72 is arranged above the wall member 82. Therefore, foreign objects are restricted from flowing toward the sensor unit 72.

In the fifteenth embodiment, the trap part 76 has at least one or more board-shaped electrode member 81. The board-shaped electrode member 81 extends is a direction of the axis of the fuel passage 74, and the width of the electrode member 81 is decreased from the upstream side to the downstream side. Therefore, a foreign object contained in the mixture fuel passing through the charge part 75 is effectively removed at the upstream side having the long width of the electrode member 81. Further, because the electrode member 81 extends parallel to the fuel passage 74, pressure loss of the mixture fuel flowing through the fuel passage 74 can be reduced. Thus, the pressure loss of the mixture fuel can be reduced, and the foreign object contained in the mixture fuel can be collected at the upstream side of the sensor unit 72. Therefore, a concentration detection accuracy of the sensor unit 72 can be made high.

Further, in the fifteenth embodiment, the wall member 82 is arranged in the fuel passage 74. The wall member 82 separates a flow of mixture fuel into the electrode member 81 of the trap part 76, or the sensor unit 72, thereby the foreign object contained in the mixture fuel is difficult to flow into the sensor unit 72. Thus, adhesion and sedimentation of the foreign object relative to the sensor unit 72 can be reduced, and accuracy for detecting specific component contained in mixture fuel can be increased.

(Sixteenth, Seventeenth and Eighteenth Embodiments)

Figure 20:
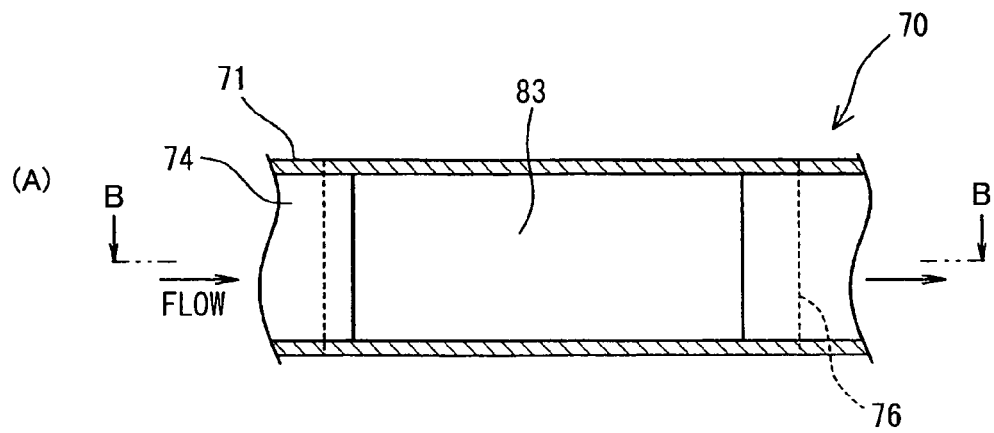
FIG. 20(A) is a schematic view illustrating a concentration sensor device according to a sixteenth embodiment.
FIG. 20(B) is a cross-sectional view taken along line B-B of FIG. 20(A)
Figure 22:
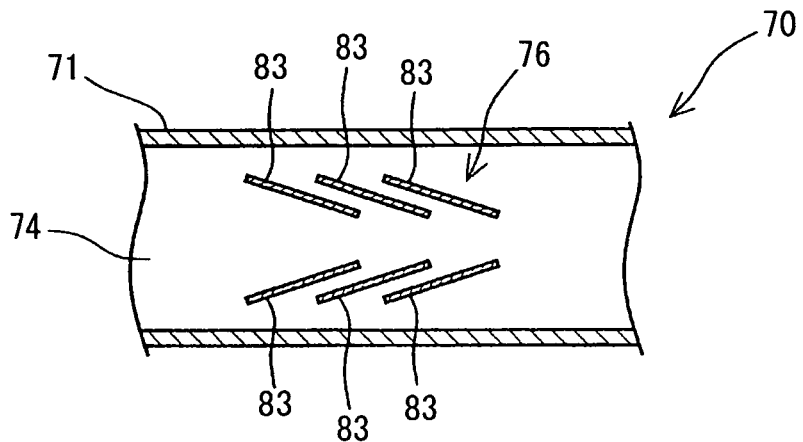
FIG. 22 is a schematic view illustrating a concentration sensor device according to a seventeenth embodiment.
Figure 24:
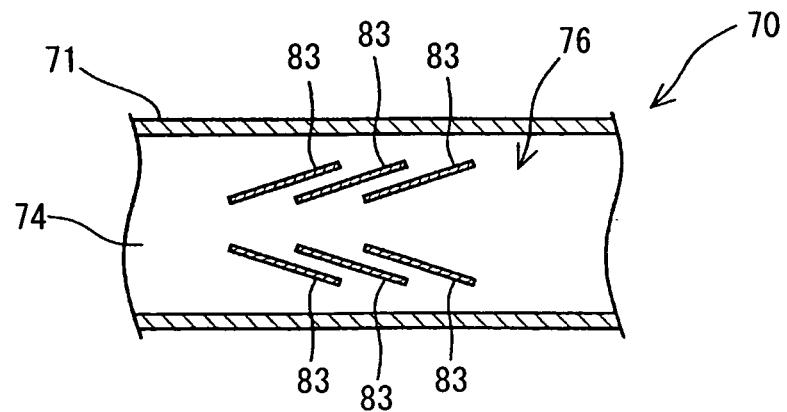
FIG. 24 is a schematic view illustrating a concentration sensor device according to an eighteenth embodiment.

Concentration sensor devices according to a sixteenth, a seventeenth and an eighteenth embodiment are shown in FIG. 20, FIG. 22 and FIG. 24, respectively.

In the sixteenth embodiment, as shown in FIG. 20, the trap part 76 of the concentration sensor device 70 has an electrode member 83 extending to be inclined relative to an axis of the fuel passage 74. The electrode member 83 has a board shape, and at least one or more electrode member 83 is arranged in the fuel passage 74. The electrode member 83 has a constant width from the upstream side to the downstream side in the flowing direction of fuel in the fuel passage 74. The electrode member 83 is located in this state, thereby at least a part of a width of the fuel passage is made narrower from the upstream side to the downstream side.

Figure 21:
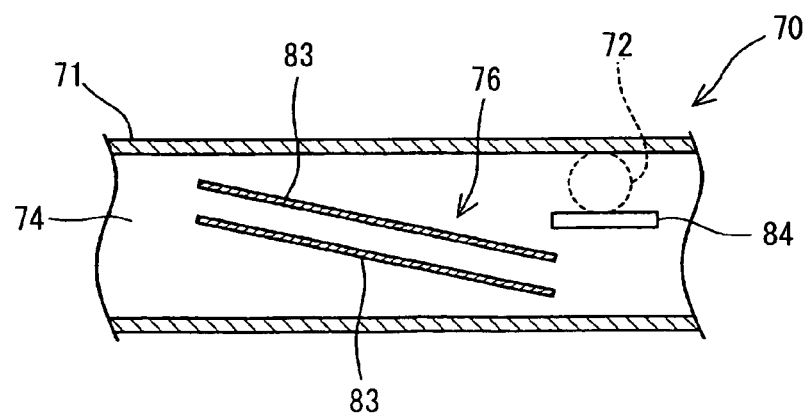
FIG. 21 is a schematic view illustrating a concentration sensor device according to a sixteenth embodiment.

As shown in FIG. 21, the device 70 may include a wall member 84. The wall member 84 separates a flow of mixture fuel passing through the charge part 75 into the sensor unit 72 or the trap part 76. Foreign object contained in the mixture fuel and charged by passing through the charge part 75 is collected by the electrode member 83 of the trap part 76. The electrode member 83 makes a part of the fuel passage 74 to become narrow from the upstream side to the downstream side. The wall member 84 separates the fuel passage 74 made narrow by the electrode member 83 and the sensor unit 72. Therefore, the foreign object contained in the mixture fuel easily moves downward of FIG. 21 along the electrode member 83. Thus, mixture fuel containing little foreign object flows above the wall member 84, and the sensor unit 72 is arranged above the wall member 84.

In the seventeenth embodiment, as shown in FIG. 22, the trap part 76 of the concentration sensor device 70 has electrode members 83 extending to be inclined relative to an axis of the fuel passage 74. The electrode member 83 has a board shape, and at least one or more electrode members 83 are arranged in the fuel passage 74. The electrode members 83 oppose to each other through an interval. The interval is set to become larger at the upstream side, and is set to become smaller at the downstream side. Further, plural sets of the opposing electrode members 83 are arranged in the fuel passage 74. Therefore, the electrode member 83 narrows the width of the fuel passage 74 from the upstream side to the downstream side, at a center part of the fuel passage 74 in the radial direction.

Figure 23:
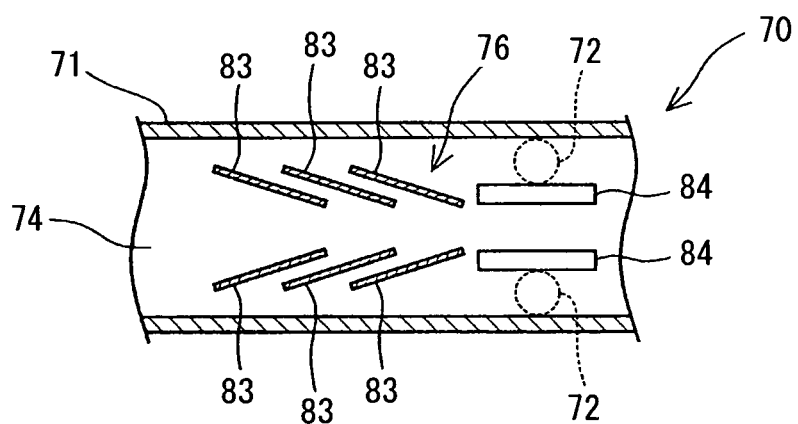
FIG. 23 is a schematic view illustrating a concentration sensor device according to a seventeenth embodiment.

As shown in FIG. 23, the device 70 may include wall members 84. In the seventeenth embodiment, the wall member 84 extends in the axis direction of the fuel passage 74 at a downstream side of the most downstream electrode member 83 narrowing the fuel passage 74. The sensor unit 72 is arranged on a circumference side from the wall member 84 in the radial direction of the passage portion 71. Mixture fuel containing foreign object charged by the charge part 75 flows between the electrode members 83 of the trap part 76, and arrives between the wall members 84. At this time, foreign object left in the mixture fuel after passing between the electrode members 83 is guided toward the center part of the fuel passage 74 together with the mixture fuel, due to the electrode member 83. Thus, the left foreign object passes between the wall members 84. Therefore, foreign object contained in the mixture fuel is difficult to flow into the sensor unit 72.

In the eighteenth embodiment, as shown in FIG. 24, the trap part 76 of the concentration sensor device 70 has an electrode member 83 extending to be inclined relative to an axis of the fuel passage 74. The electrode member 83 has a board shape, and at least one or more electrode members 83 are arranged in the fuel passage 74. The electrode members 83 oppose to each other through an interval. The interval is set to become narrower at the upstream side, and is set to become wider at the downstream side. Further, plural sets of the opposing electrode members 83 are arranged in the fuel passage 74. Therefore, the electrode member 83 narrows a circumference side width of the fuel passage 74 from the upstream side to the downstream side.

Figure 25:
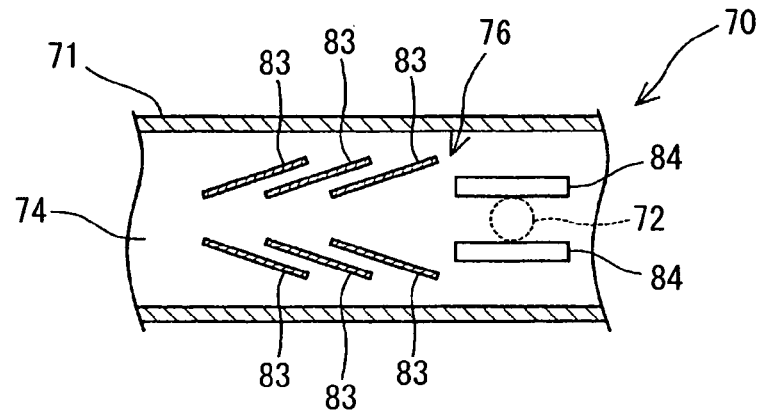
FIG. 25 is a schematic view illustrating a concentration sensor device according to an eighteenth embodiment.

As shown in FIG. 25, the device 70 may include wall members 84. In the eighteenth embodiment, the wall member 84 extends in the axis direction of the fuel passage 74 at a downstream side of the most downstream electrode member 83 narrowing the fuel passage 74. The sensor unit 72 is arranged at an inner side from the wall member 84 in the radial direction of the passage portion 71. That is, the sensor unit 72 is arranged between the wall members 84. Mixture fuel containing foreign object charged by the charge part 75 flows between the electrode members 83 of the trap part 76. At this time, foreign object left in the mixture fuel after passing between the electrode members 83 is guided toward the circumference part of the fuel passage 74, due to the electrode member 83. Thus, the left foreign object passes outside of the wall members 84. Therefore, foreign object contained in the mixture fuel is difficult to flow into the sensor unit 72:

In the sixteenth, seventeenth, eighteenth embodiments, the trap part 76 includes at least one or more board-shaped electrode members 83. The board-shaped electrode members 83 extends to be inclined to the axis of the fuel passage 74. The board-shaped electrode members 83 narrows at least a part of the width of the fuel passage 74 from the upstream side to the downstream side. Therefore, liquid flowing through the fuel passage 74 flows between the electrode members 83, and a dimension between the electrode members 83 gradually becomes narrow. Thus, foreign object contained in the mixture fuel is easily collected by the trap part 76. Further, the wall member 84 guides mixture fuel containing less foreign object toward the sensor unit 72. Accordingly, foreign object contained in mixture fuel can be collected at the upstream side of the sensor unit 72, such that concentration detection accuracy of the sensor unit 72 can be made higher.

(Nineteenth and Twentieth Embodiments)

Figure 26:
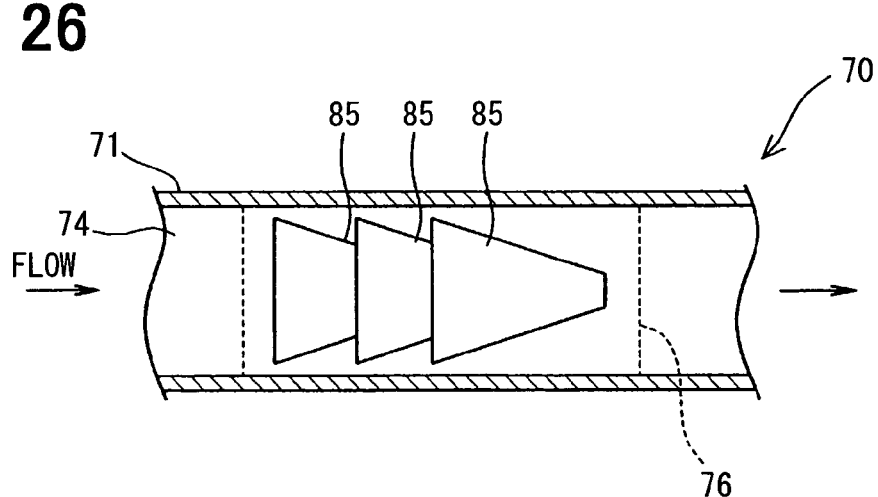
FIG. 26 is a schematic view illustrating a concentration sensor device according to a nineteenth embodiment.
Figure 28:
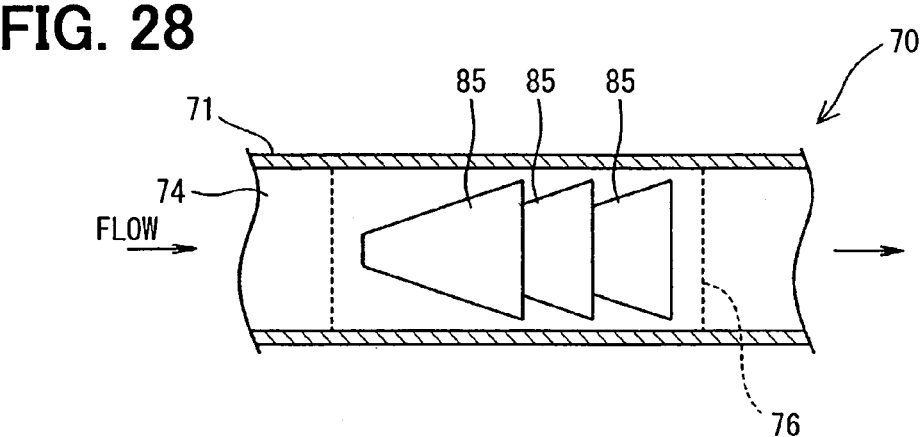
FIG. 28 is a schematic view illustrating a concentration sensor device according to a twentieth embodiment.

Concentration sensor devices according to nineteenth and twentieth embodiment are shown in FIG. 26 and FIG. 28, respectively.

In the nineteenth embodiment, as shown in FIG. 26, the trap part 76 of the concentration sensor device 70 has at least one or more electrode member 85. The electrode member 85 has a cone shape or a pyramid shape, and ends of the electrode member 85 are opened like a tube. The cone shape or the pyramid shape may be truncated, and a plurality of the truncated shapes are arranged to be overlap with each other to form plural steps. In the nineteenth embodiment, the electrode member 85 has a cone-tube shape, in which an inner diameter of the cone-tube shape is decreased from the upstream side to the downstream side, in the fuel passage 74. The electrode member 85 may have a mesh texture, or may be porous, such that a pressure loss of mixture fuel passing through the electrode member 85 is reduced.

Figure 27:
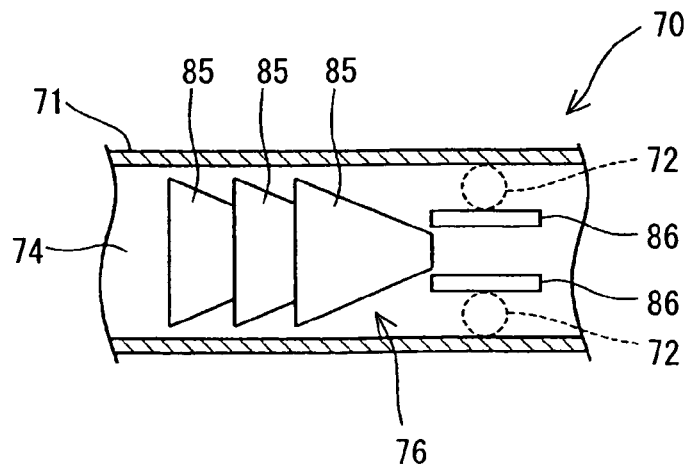
FIG. 27 is a schematic view illustrating a concentration sensor device according to a nineteenth embodiment.

Further, as shown in FIG. 27, the device 70 may include wall members 86. In the nineteenth embodiment, the wall member 86 extends in the axis direction of the fuel passage 74 at a downstream side of the most downstream electrode member. The sensor unit 72 is arranged at a circumference side from the wall member 86 in the radial direction of the passage portion 71. Flow of mixture fuel containing foreign object charged by the charge part 75 is guided by the electrode member 85 of the trap part 76, and arrives between the wall members 86. At this time, foreign object left in the mixture fuel after passing through the electrode members 85 is guided toward the center part of the fuel passage 74, due to the electrode member 85, and passes between the wall members 86. Therefore, foreign object contained in the mixture fuel is difficult to flow into the sensor unit 72.

In the twentieth embodiment, as shown in FIG. 28, the trap part 76 of the concentration sensor device 70 has at least one or more electrode member 85. The electrode member 85 has a cone shape or a pyramid shape, and ends of the electrode member 85 are opened like a tube. The cone shape or the pyramid shape may be truncated, and a plurality of the truncated shapes are arranged to be overlap with each other to form plural steps. In the twentieth embodiment, the electrode member 85 has a cone-tube shape, and an inner diameter of the cone-tube shape is enlarged from the upstream side to the downstream side, in the fuel passage 74. Therefore, the electrode member 85 has a shape in a manner that a flow of fuel is guided from the center part of the passage portion 71 toward the circumference side of the fuel passage 74. The electrode member 85 may have a mesh texture, or may be porous, such that a pressure loss of mixture fuel passing through the electrode member 85 is reduced.

Figure 29:
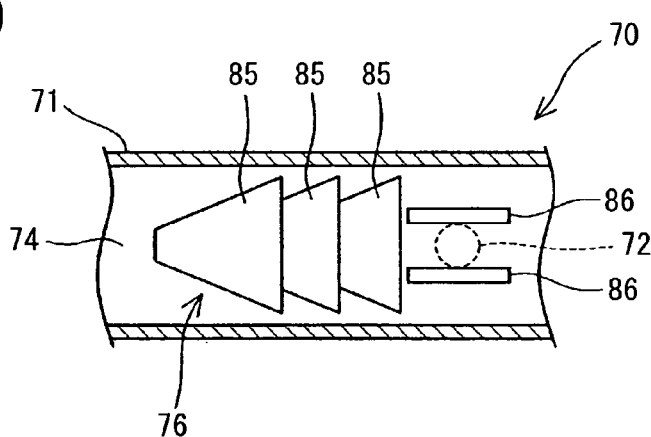
FIG. 29 is a schematic view illustrating a concentration sensor device according to a twentieth embodiment.

Further, as shown in FIG. 29, the device 70 may include wall members 86. In the twentieth embodiment, the wall member 86 extends in the axis direction of the fuel passage 74 at a downstream side of the most downstream electrode member 85. The sensor unit 72 is arranged at an inner side from the wall members 86 in the radial direction of the passage portion 71. That is, the sensor unit 72 is arranged between the wall members 86. Mixture fuel containing foreign object charged by the charge part 75 is guided by the electrode member 85 of the trap part 76 toward the circumference side of the fuel passage 74, and passes outside of the wall members 86. Therefore, foreign object contained in the mixture fuel is difficult to flow into the sensor unit 72.

In the nineteenth embodiment, the trap part 76 has at least one or more electrode member 85. The inner diameter of the electrode member 85 is decreased from the upstream side to the downstream side. Therefore, when mixture fuel passes through the electrode member 85, the inner diameter of the electrode member 85 is gradually decreased. Thus, foreign object contained in the mixture fuel is easily collected by the trap part 76.

In the twentieth embodiment, the trap part 76 has at least one or more electrode member 85. The electrode member 85 has a shape in a manner that a flow of fuel is guided toward the inner wall of the passage portion 71 from the upstream side to the downstream side, in the fuel passage 74. Therefore, when mixture fuel passes through the electrode member 85, the mixture fuel gradually becomes closer to the inner wall of the passage portion 71. Thus, foreign object contained in the mixture fuel is easily collected by the trap part 76, and the pressure loss of mixture fuel becomes relatively small.

Further, in the nineteenth and twentieth embodiments, the wall member 86 guides mixture fuel toward the sensor unit 72, and the guided mixture fuel contains less foreign object after passing through the trap part 76. Accordingly, foreign object contained in mixture fuel can be collected at the upstream side of the sensor unit 72, such that concentration detection accuracy of the sensor unit 72 can be made higher.

(21st Embodiment)

Figure 30:
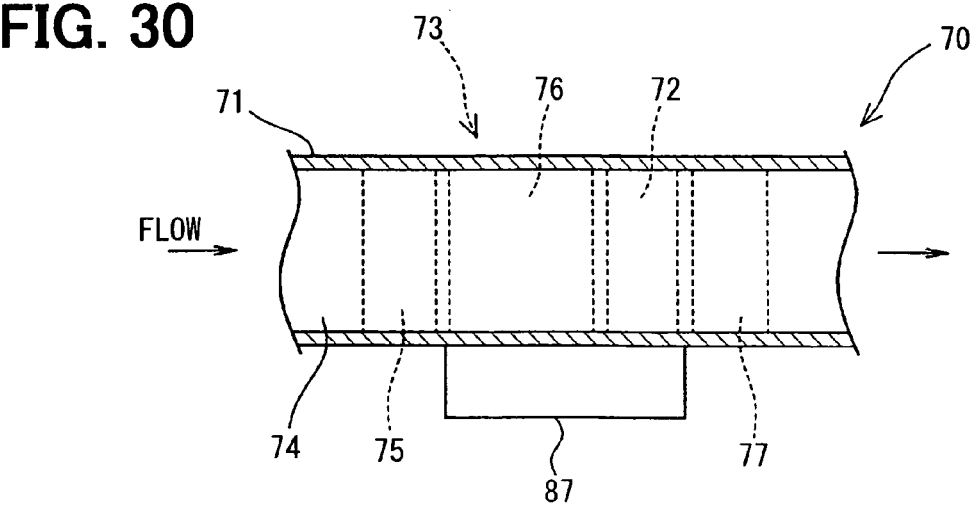
FIG. 30 is a schematic view illustrating a concentration sensor device according to a 21st embodiment.

FIG. 30 shows a concentration sensor device, according to a 21st embodiment.

In the 21st embodiment, as shown in FIG. 30, a concentration sensor device 70 has a vibration generator 87 corresponding to a vibration providing portion. The vibration generator 87 is arranged outside of the passage portion 71, and gives vibration to the passage portion 71. Foreign objects may be accumulated to the charge part 75 and the trap part 76 arranged in the fuel passage 74 after a long time use. The vibration generator 87 intermittently makes the passage portion 71 defining the fuel passage 74 to vibrate. The charge part 75 and the trap part 76 vibrate together with the passage portion 71. Especially when the vibration generator 87 is arranged adjacent to the charge part 75 and the trap part 76, the vibrations of the charge part 75 and the trap part 76 are promoted. Thus, sedimentation of the foreign objects to the charge part 75 and the trap part 76 can be reduced, such that operations of the charge part 75 and the trap part 76 can be maintained for a long time.

(22nd, 23rd and 24th Embodiments)

Figure 31:
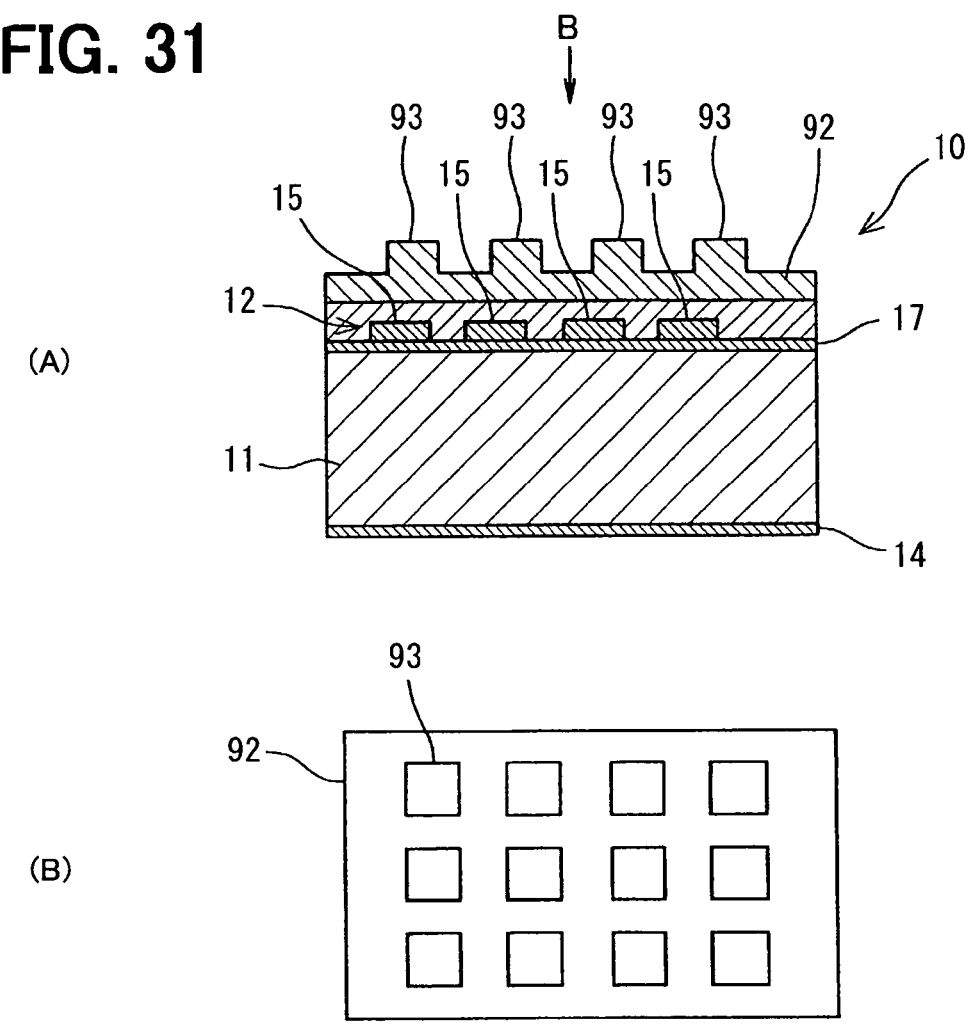
FIG. 31(A) is a cross-sectional view illustrating a concentration sensor device according to a 22nd embodiment.
FIG. 31(B) is a plan view taken in an arrow direction B of FIG. 31(A)
Figure 32:
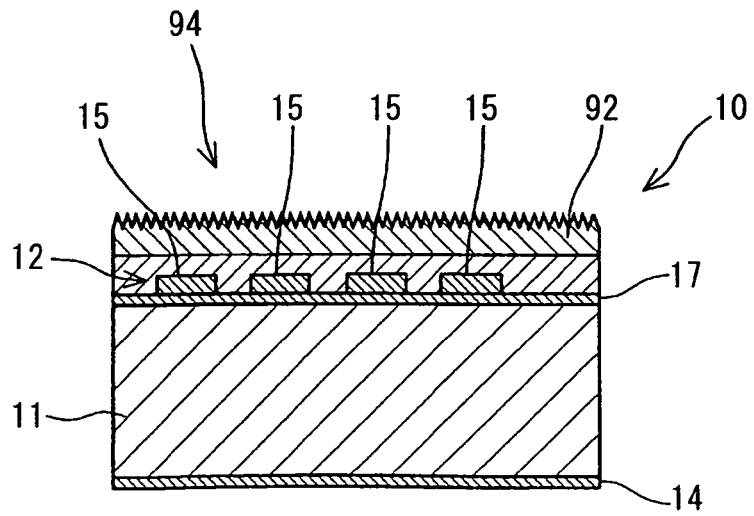
FIG. 32 is a cross-sectional view illustrating a concentration sensor device according to a 23rd embodiment, the view corresponding to FIG. 31(A)
Figure 33:
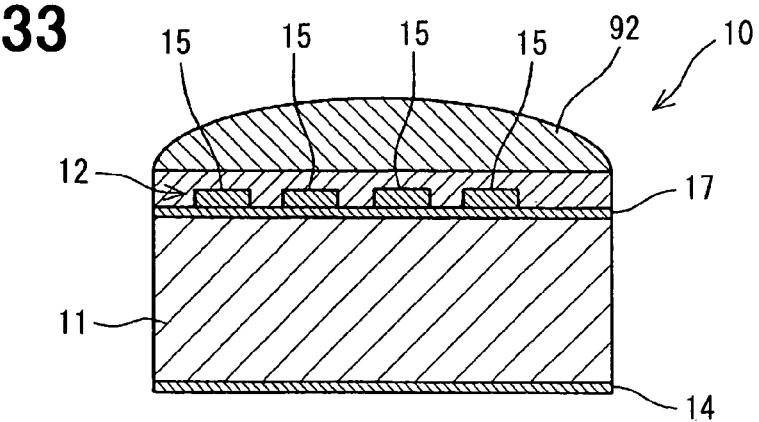
FIG. 33 is a cross-sectional view illustrating a concentration sensor device according to a 24th embodiment, the view corresponding to FIG. 31(A)

Concentration sensor devices according to 22nd, 23rd and 24th embodiments are shown in FIG. 31, FIG. 32 and FIG. 33, respectively.

In the 22nd embodiment, as shown in FIG. 31, a concentration sensor device 10 includes a substrate 11 and a sensor unit 12. An insulation film 14 is arranged on a face of the substrate 11 opposite from the sensor unit 12, and an insulation film 17 is arranged between the substrate 11 and the sensor unit 12. The sensor unit 12 has plural electrodes 15, similarly to the first embodiment. The electrodes 15 of the sensor unit 12 are protected by a protection film 16.

In the 22nd embodiment, the device 10 has a second protection film 92 on a face of the protection film 16 opposite from the substrate 11. The second protection film 92 has a rough face opposite from the sensor unit 12, and the rough face is exposed to mixture fuel. Specifically, in the device 10 of FIG. 31, the rough face of the second protection film 92 has projections 93 opposite from the sensor unit 12. The second protection film 92 corresponds to a protection film of claims.

In the 23rd embodiment, as shown in FIG. 32, the device 10 has a second protection film 92 on a face of the protection film 16 opposite from the substrate 11. The second protection film 92 has a rough face opposite from the sensor unit 12, and the rough face is exposed to mixture fuel. Specifically, in the device 10 of FIG. 32, the rough face of the second protection film 92 has sharp bumps 94 opposite from the sensor unit 12. The second protection film 92 is not limited to be constructed by the sharp bumps 94. For example, the rough face may be formed by damaging by sandblast.

In the 24th embodiment, as shown in FIG. 33, the device 10 has a second protection film 92 on a face of the protection film 16 opposite from the substrate 11. The second protection film 92 has a convex face opposite from the sensor unit 12, and the convex face is exposed to mixture fuel. Specifically, in the device 10 of FIG. 33, the second protection film 92 is formed into a convex shape protruding from the protection film 16 toward a direction opposite from the sensor unit 12.

In the 22nd, 23rd and 24th embodiments, the device 10 includes the second protection film 92 covering the sensor unit 12. The second protection film 92 has a sedimentation limit unit integrated with an end face of the second protection film 92 opposite from the sensor unit 12. In the 22nd embodiment, the second protection film 92 has the sedimentation limit unit opposite from the sensor unit 12, and the sedimentation limit unit is formed into the rough face having the projections 93. Further, in the 23rd embodiment, the second protection film 92 has the sedimentation limit unit opposite from the sensor unit 12, and the sedimentation limit unit is formed into the rough face having the bumps 94. Further, in the 24th embodiment, the second protection film 92 has the sedimentation limit unit opposite from the sensor unit 12, and the sedimentation limit unit is formed into the convex face. Therefore, in the 22nd, 23rd and 24th embodiments, foreign objects are restricted from adhering on the face of the second protection film 92 opposite from the sensor unit 12. Thus, adhesion and sedimentation of foreign objects to the sensor unit 12 can be reduced, such that accuracy for detecting a specific component contained in the mixture fuel can be increased.

(25th Embodiment)

Figure 34:
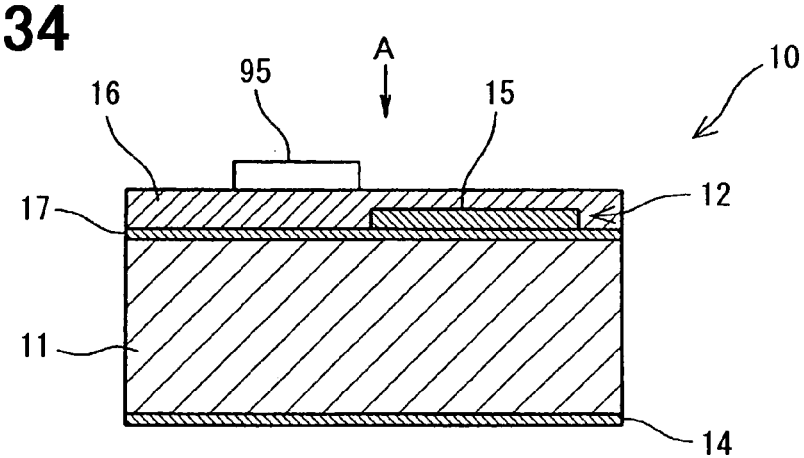
FIG. 34 is a cross-sectional view illustrating a concentration sensor device according to a 25th embodiment, the view corresponding to FIG. 31(A)
Figure 35:
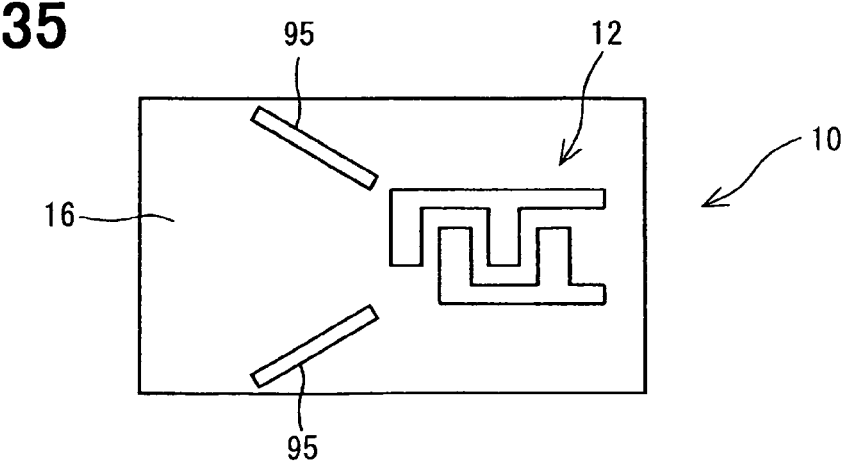
FIG. 35 is a plan view taken in an arrow direction A of FIG. 34.

A concentration sensor device 10 according to a 25th embodiment is shown in FIG. 34 and FIG. 35.

Figure 36:
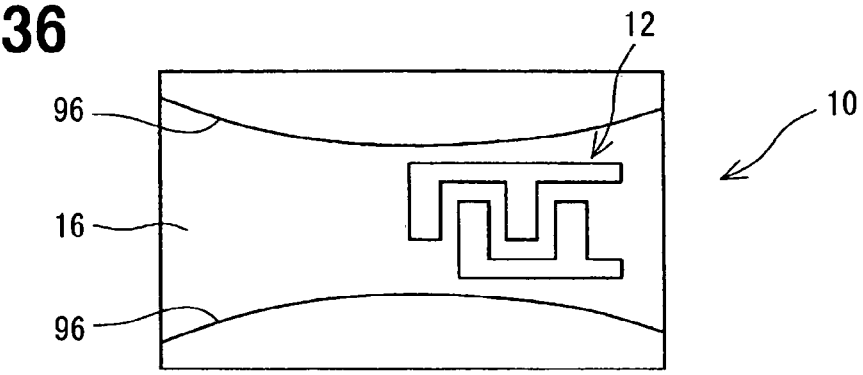
FIG. 36 is a plan view illustrating a modified concentration sensor device according to a 25th embodiment, the view corresponding to FIG. 35.

In the 25th embodiment, the concentration sensor device 10 has a passage formation part 95 on a side of the protection film 16 opposite from the sensor unit 12. The passage formation part 95 is defined on an end face of the protection film 16 opposite from the sensor unit 12. As shown in FIG. 35, the passage formation part 95 is arranged so as to define a flow of mixture fuel toward the sensor unit 12. Mixture fuel flowing through the fuel passage is guided toward the protection film 16 covering the sensor unit 12 opposite from the substrate 11, due to the passage formation part 95. Therefore, mixture fuel has a tendency to flow adjacent to a side of the sensor unit 12 opposite from the substrate 11. If a foreign object adheres on the protection film 16, the foreign object is removed by a flow of the mixture fuel formed by the passage formation part 95. As shown in FIG. 36, a passage formation part 96 may have a curve shape toward the sensor unit 12. The curve-shaped passage formation part 96 can guide the flow of the mixture fuel toward the sensor unit 12.

In the 25th embodiment, the protection film 16 has the passage formation part 95, 96. The passage formation part 95, 96 forms the flow of mixture fuel toward the sensor unit 12 on a surface of the protection film 16. Therefore, a foreign object adhering on the protection film 16 is removed by the flow of mixture fuel. Thus, the foreign object is restricted from adhering on the protection film 16. Accordingly, adhesion and sedimentation of foreign object to the sensor unit 12 can be reduced, such that accuracy for detecting a specific component contained in the mixture fuel can be increased.

(26th Embodiment)

Figure 37:
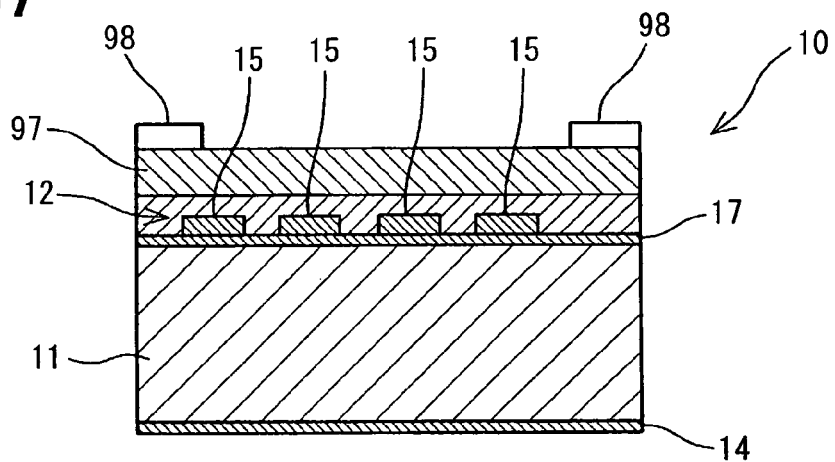
FIG. 37 is a cross-sectional view illustrating a concentration sensor device according to a 26th embodiment, the view corresponding to FIG. 31(A)

FIG. 37 shows a concentration sensor device 10 according to a 26th embodiment.

In the 26th embodiment, the concentration sensor device 10 has a porous member 97 on the protection film 16 opposite from the sensor unit 12. The porous member 97 is another protection film to protect the protection film 16. The porous member 97 has plural holes, which allows the mixture fuel to pass through the member 97 and limits a foreign object contained in the mixture fuel from passing through the member 97. Because the porous member 97 limits the passing of the foreign object, the foreign object contained in the mixture fuel does not contact the sensor unit 12.

When the sensor unit 12 is covered by the porous member 97, the foreign object contained in the mixture fuel easily adheres and accumulates on the face of the porous member 97 opposite from the sensor unit 12. The device 10 may further include a vibration generator 98 to give vibration to the porous member 97. The vibration generator 98 is made of a piezoelectric element, for example, and vibration is generated when electricity is supplied to the vibration generator 98. Vibration generated by the vibration generator 98 makes the porous member 97 to vibrate. Thus, foreign object adhering or accumulating on the porous member 97 is removed from the porous member 97, due to the vibration.

Figure 38:
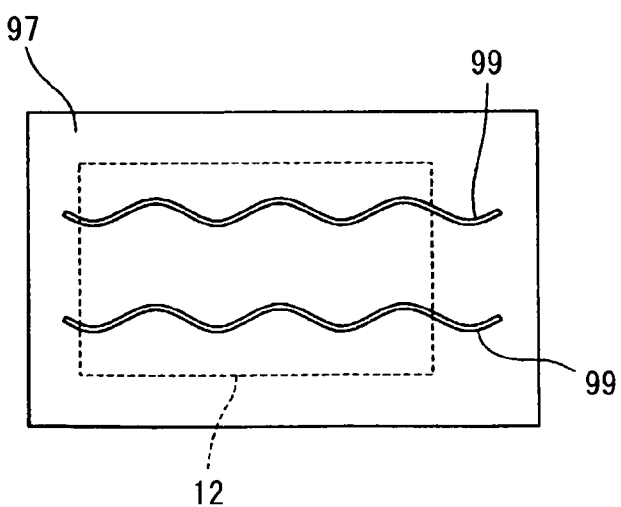
FIG. 38 is a plan view illustrating a modified concentration sensor device according to a 26th embodiment, the view corresponding to FIG. 35.

The vibration generator 98 may be a vibrator 99 shown in FIG. 38. The vibrator 99 has a membrane shape, and is arranged on the porous member 97 opposite from the sensor unit 12. When mixture fuel flows on a side of the porous member 97 opposite from the sensor unit 12, the vibrator 99 vibrates due to the flow of mixture fuel. Thus, vibration is provided to the porous member 97 by the vibrator 99. That is, the vibrator 99 corresponds to a vibration providing portion of claims. By using the vibrator 99, vibration can be provided to the porous member 97 by the flow of mixture fuel without electricity power.

In the 26th embodiment, the device 10 includes the protection film made of the porous member 97. Holes of the porous member 97 allow the mixture fuel to flow through the porous member 97, and limits a foreign object contained in the mixture fuel from passing through the porous member 97. Therefore, the foreign object accumulates to the porous member 97, and does not adhere on the sensor unit 12. Accordingly, adhesion and sedimentation of the foreign object to the sensor unit 12 can be reduced, such that accuracy for detecting a specific component contained in the mixture fuel can be increased.

Further, in the 26th embodiment, the vibration generator 98 provides vibration to the porous member 97. By using the porous member 97, foreign objects contained in the mixture fuel easily accumulate on a surface of the porous member 97. Therefore, when the porous member 97 is vibrated by the vibration generator 98, the foreign objects accumulating on the porous member 97 can be removed.

In the above embodiments, the through electrode 19 electrically connects the piezoelectric element 13 and the circuit unit 18. Alternatively, the piezoelectric element 13 and the circuit unit 18 may be connected through a bonding wire or bump, for example. Further, as shown in FIG. 14, a part of the device 10 such as the piezoelectric element 13 may be electrically connected to the outside mount substrate 103 through a bonding wire or the solder ball 33, for example.

In the above embodiments, the bio-origin alcohol contained in the mixture fuel is described as the specific component of the liquid. Alternatively, the liquid may be lubrication oil, alcohol or water, other than the mixture fuel.

A 27th embodiment will be described with reference to drawings, in a case that the present invention is applied for calculating a mixture ratio of mixture liquid constructed by alcohol and gasoline. Gasoline is constructed by several hundred kinds of components, but the components have permittivities equal to each other. Therefore, in the 27th embodiment, gasoline is regarded to be a single component contained in the mixture liquid, thereby the mixture liquid is regarded to be composed of two components, which are alcohol and gasoline.

(27th Embodiment)

Figure 39:
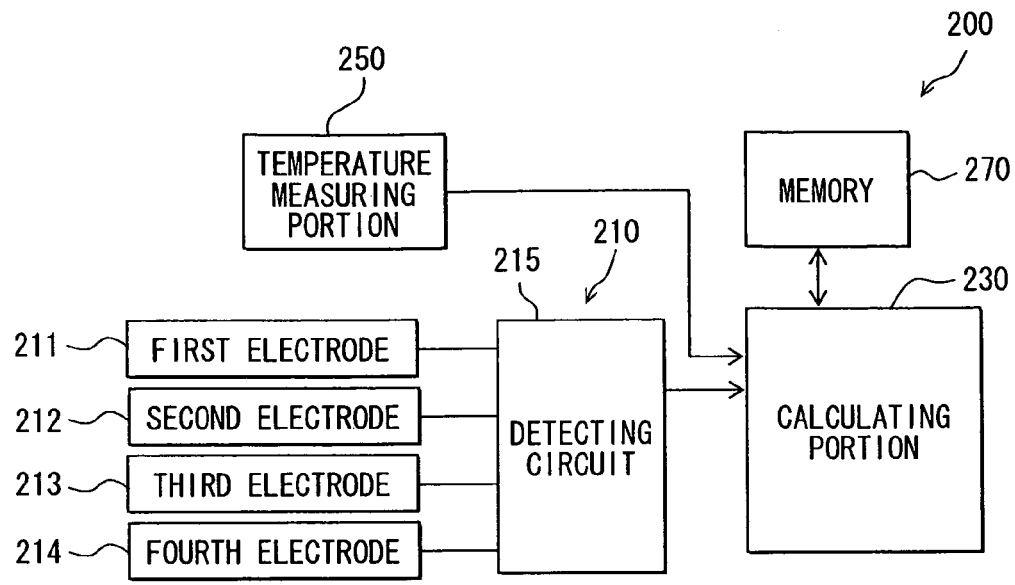
FIG. 39 is a block diagram illustrating a mixture ratio calculating device according to a 27th embodiment.
Figure 40:
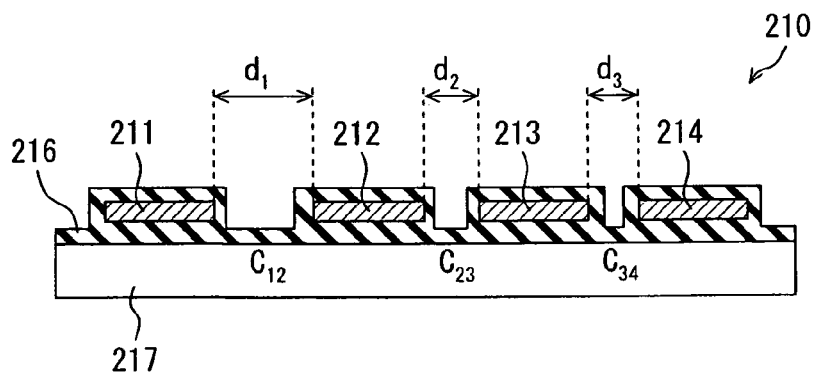
FIG. 40 is a cross-sectional view illustrating electrodes of the mixture ratio calculating device.
Figure 41:
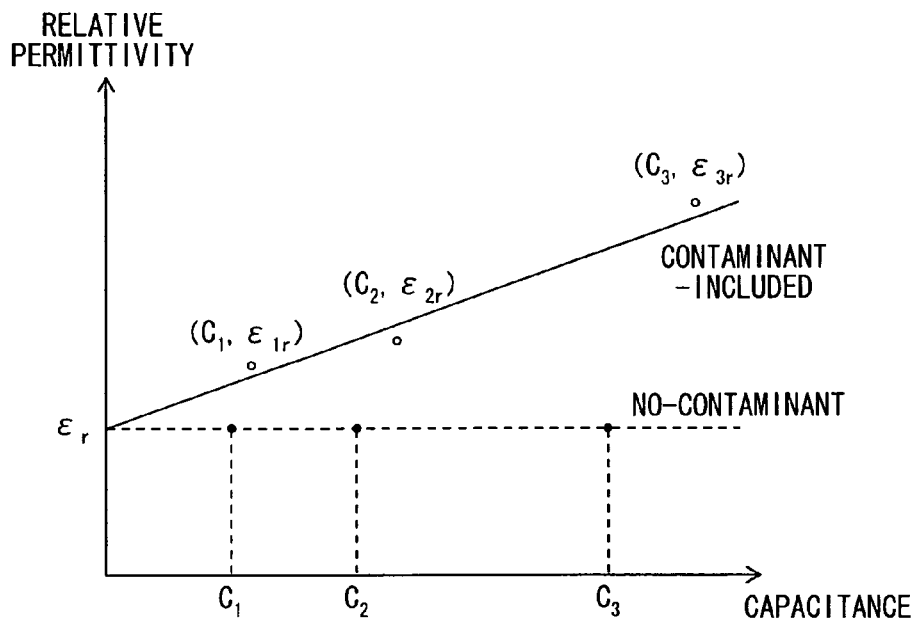
FIG. 41 is a graph illustrating a relationship between a capacitance and a relative permittivity.

FIG. 39 shows a block diagram illustrating a mixture ratio calculating device according to the 27th embodiment. FIG. 40 is a cross-sectional view illustrating schematic construction of electrodes. FIG. 41 is a graph between a capacitance and a relative permittivity. In FIG. 41, a horizontal axis represents the capacitance, and a vertical axis represents the relative permittivity.

As shown in FIG. 39, a mixture ratio calculating device 200 includes a sensor portion 210 and a calculating portion 230, as a main part. The sensor portion 210 measures a capacitance representing a permittivity of the mixture liquid, and converts the capacitance to an electric signal. The calculating portion 230 calculates a mixture ratio of the mixture liquid based on a signal output from the sensor portion 210. Further, the mixture ratio calculating device 200 includes a temperature measuring portion 250 and a memory 270.

The temperature measuring portion 250 measures a temperature of the mixture liquid. Electrodes 211-214 to be described below construct capacitors, and a vacuum capacitance of the capacitor in a vacuum state is memorized in the memory 270. The memory 270 further memorizes relative permittivities of alcohol and gasoline contained in the mixture liquid. The memory 270 further memorizes temperature characteristics of the relative permittivities.

The sensor portion 210 has four of the electrodes 211-214 and a detecting circuit 215. The electrodes 211-214 are located in the mixture liquid. The detecting circuit 215 detects capacitances representing permittivities of the mixture liquid measured by the electrodes 211-214, and converts the detected capacitance to an electric signal. As shown in FIG. 40, the electrode 211-214 has a rectangular cross-section, and is arranged on a substrate 217 through an insulating protection film 216. A surface of the electrode 211-214 is covered and protected by the protection film 216.

As shown in FIG. 40, when a first electrode 211 and a second electrode 212 oppose to each other, a capacitor $C_{12}$ is constructed by the first electrode 211 and the second electrode 212. When the second electrode 212 and a third electrode 213 oppose to each other, a capacitor $C_{23}$ is constructed by the second electrode 212 and the third electrode 213. When the third electrode 213 and a fourth electrode 214 oppose to each other, a capacitor $C_{34}$ is constructed by the third electrode 213 and the fourth electrode 214. Opposing areas between the capacitors $C_{12}$, $C_{23}$, $C_{34}$ are equal to each other. In contrast, an electrode interval $d_1$ between the first electrode 211 and the second electrode 212 is larger than an electrode interval $d_2$ between the second electrode 212 and the third electrode 213. The electrode interval $d_2$ is larger than an electrode interval $d_3$ between the third electrode 213 and the fourth electrode 214. Because the capacitance of the capacitor is proportional to the opposing area and a reciprocal of the electrode interval, a ratio among the capacitances of the capacitors $C_{12}$, $C_{23}$, $C_{34}$ is equal to a ratio among the reciprocals of the electrode intervals. In this embodiment, because the ratio among the electrode intervals $d_1$, $d_2$, $d_3$ is equal to 4:2:1, the ratio among the capacitances of the capacitors $C_{12}$, $C_{23}$, $C_{34}$ is equal to 1:2:4. In this embodiment, the protection film 216 located between adjacent electrodes 211, 212, 213, 214 is regarded not to exist.

The sensor portion 210 measures the capacitances $C_1$, $C_2$, $C_3$ of the capacitors $C_{12}$, $C_{23}$, $C_{34}$. The calculating portion 230 detects relative permittivities $\epsilon_{1r}$, $\epsilon_{2r}$, $\epsilon^{3r}$ of the mixture liquid based on the capacitances $C_1$, $C_2$, $C_3$. The calculating portion 230 calculates a regression line between the capacitances $C_1$, $C_2$, $C_3$ and the relative permittivities $\epsilon_{1r}$, $\epsilon_{2r}$, $\epsilon_{3r}$. Thus, a corrected relative permittivity $\epsilon_r$ can be calculated. A mixture ratio a, b of the mixture liquid is calculated based on the corrected relative permittivity $\epsilon_r$. The temperature measuring portion 250 and the memory 270 are connected to the calculating portion 230. The temperature measuring portion 250 measures temperature of the mixture liquid. The memory 270 memorizes the vacuum capacitance $C_{012}$, $C_{023}$, $C_{034}$ of the capacitor $C_{12}$, $C_{23}$, $C_{34}$ located in the vacuum state, the relative permittivities $\epsilon_{ar}$, $\epsilon_{br}$ of alcohol and gasoline, and the temperature characteristics of the relative permittivities $\epsilon_{ar}$, $\epsilon_{br}$. The calculating portion 230 obtains measurement result from the temperature measuring portion 250, and obtains parameter necessary for the calculation from the memory 270, so as to calculate the mixture ratio a, b.

Next, a method of calculating the mixture ratio will be described. The capacitance $C_1$, $C_2$, $C_3$ of the capacitor $C_{12}$, $C_{23}$, $C_{34}$ is measured by the detecting circuit 215 of the sensor portion 210, and the measured capacitance $C_1$, $C_2$, $C_3$ is converted to an electric signal. When the electric signal is input into the calculating portion 230 from the sensor portion 210, the calculating portion 230 obtains the vacuum capacitance $C_{012}$, $C_{023}$, $C_{034}$ from the memory 270. Division is performed between the measured capacitance $C_1$, $C_2$, $C_3$ and the vacuum capacitance $C_{012}$, $C_{023}$, $C_{034}$, thereby the relative permittivity $\epsilon_{1r}$, $\epsilon_{2r}$, $\epsilon_{3r}$ is calculated so as to correspond to a first calculating process of claims.

Calculations performed in the first calculating process will be described below. Because the capacitance is equal to a multiplication between the relative permittivity and the vacuum capacitance, relationship among the capacitance $C_1$, $C_2$, $C_3$, the relative permittivity $\epsilon_{1r}$, $\epsilon_{2r}$, $\epsilon_{3r}$, and the vacuum capacitance $C_{012}$, $C_{023}$, $C_{034}$ are shown in Formula (1A)-(1C).

(Formula 1)

$$C_1 = \epsilon_{1r} \times C_{012} \tag{1A}$$

$$C_2 = \epsilon_{2r} \times C_{023} \tag{1B}$$

$$C_3 = \epsilon_{3r} \times C_{034} \tag{1C}$$

As shown in Formula (2A)-(2C), when the capacitance $C_1$, $C_2$, $C_3$ is divided by the vacuum capacitance $C_{012}$, $C_{023}$, $C_{034}$, the relative permittivity $\epsilon_{1r}$, $\epsilon_{2r}$, $\epsilon_{3r}$ can be calculated from the capacitance $C_1$, $C_2$, $C_3$.

(Formula 2)

$$\epsilon_{1r} = C_1/C_{012} \tag{2A}$$

$$\epsilon_{2r} = C_2/C_{023} \tag{2B}$$

$$\epsilon_{3r} = C_3/C_{034} \tag{2C}$$

After the first calculating process is finished, the calculating portion 230 calculates a regression line between the measured capacitance $C_1$, $C_2$, $C_3$ and the calculated relative permittivity $\epsilon_{1r}$, $\epsilon_{2r}$, $\epsilon_{3r}$ so as to correspond to a second calculating process of claims. The regression line is calculated by using a known method of least squares, such that a description of the calculation is omitted.

After the second calculating process is finished, the calculating portion 230 calculates a relative permittivity (intercept) in the regression line by assigning zero in the capacitance. Thus, the corrected relative permittivity is calculated so as to correspond to a third calculating process of claims.

A reason will be described below why the corrected relative permittivity is calculated by defining the capacitance to be zero in the regression line. The corrected relative permittivity is a relative permittivity in which influence of contaminant is eliminated. When the mixture liquid is defined to have a relative permittivity $\epsilon_r$, and when the relative permittivity $\epsilon_r$ is defined to be varied by an error factor $\alpha_1$, $\alpha_2$, $\alpha_3$ by a foreign object adhering on the capacitor $C_{12}$, $C_{23}$, $C_{34}$, Formula (1A)-(1C) are changed to Formula (3A)-(3C).

(Formula 3)

$$C_1 = (\epsilon_r + \alpha_1) \times C_{012} \tag{3A}$$

$$C_2 = (\epsilon_r + \alpha_2) \times C_{023} \tag{3B}$$

$$C_3 = (\epsilon_r + \alpha_3) \times C_{034} \tag{3C}$$

Further, when the capacitor $C_{12}$, $C_{23}$, $C_{34}$ is defined to be varied by an error factor $\beta_1$, $\beta_2$, $\beta_3$ by a foreign object contained in the mixture liquid, Formula (1A)-(1C) are changed to Formula (4A)-(4C).

(Formula 4)

$$C_1 = \epsilon_r \times C_{012} + \beta_1 \tag{4A}$$

$$C_2 = \epsilon_r \times C_{023} + \beta_2 \tag{4B}$$

$$C_3 = \epsilon_r \times C_{034} + \beta_3 \tag{4C}$$

Based on Formula (3A)-(3C) and Formula (4A)-(4C), $\beta_1$ is equal to $\alpha_1 \times C_{012}$, $\beta_2$ is equal to $\alpha_2 \times C_{023}$, and $\beta_3$ is equal to $\alpha_3 \times C_{034}$, such that $\beta$ is proportional to $\alpha$.

Because the relative permittivity $\epsilon_r$ and the vacuum capacitance $C_{012}$, $C_{023}$, $C_{034}$ are constant, the multiplication $\epsilon_r \times C_{012}$, $\epsilon_r \times C_{023}$, $\epsilon_r \times C_{034}$ is constant. Therefore, when the error factor $\alpha$, $\beta$ does not exist, as shown in a broken line of FIG. 41, a liner line defined by connecting estimated values (black points) of the capacitance and the relative permittivity is parallel to the horizontal axis (capacitance). However, as shown in FIG. 41, actual measurement points (white points) are larger than the estimated values in both of the capacitance and the relative permittivity. This is because the relative permittivity of the foreign object such as organic or inorganic object contained in the mixture liquid is higher than the relative permittivity of the mixture liquid. That is, the error factor $\alpha$ has a positive value. Further, as shown in FIG. 41, as the capacitance is increased, both of the measured capacitance and the calculated relative permittivity are increased. That is, as the capacitance is increased, the error factor $\alpha$, $\beta$ is increased. As an interval between the electrodes becomes narrower (as the capacitance is increased), a ratio of the foreign object to the interval is increased, thereby influence of the foreign object adhering on the electrodes 211-214 becomes large. Therefore, as shown in a solid line of FIG. 41, the regression line calculated based on the measurement points is a rightward increasing line, in which the relative permittivity is proportional to the capacitance. A cross point between the regression line and the vertical axis is a relative permittivity to be obtained when the capacitance has the smallest value (when the interval between the electrodes is infinite). That is, the cross point represents a permittivity when the ratio of the foreign object to the interval is the lowest. Further, the cross point represents a permittivity when the influence of the contaminant is the smallest. Thus, a value of the cross point between the calculated regression line and the vertical axis (relative permittivity) corresponds to the relative permittivity $\epsilon_r$ of the mixture liquid in which the influence of the contaminant is eliminated. That is, when the capacitance is zero, a value of the relative permittivity of the regression line corresponds to the relative permittivity $\epsilon_r$ of the mixture liquid in which the influence of the contaminant is eliminated. In FIG. 41, plots of the points may be exaggerated for convenience.

After the third calculating process is finished, the calculating portion 230 obtains the relative permittivities $\epsilon_{ar}$, $\epsilon_{br}$ of alcohol and gasoline from the memory 270. The relative permittivity $\epsilon_{ar}$, $\epsilon_{br}$ corresponds to the temperature of the mixture liquid measured by the temperature measuring portion 250. The calculating portion 230 calculates the mixture ratio a, b based on the relative permittivities $\epsilon_r$, $\epsilon_{ar}$, $\epsilon_{br}$ so as to correspond to a fourth calculating process of claims.

Calculations performed in the fourth calculating process are described below. The relative permittivity of the mixture liquid is typically equal to a linear sum of multiplications between a relative permittivity of a component and a mixture ratio of the component. Thus, the relative permittivity $\epsilon_r$ of the mixture liquid is represented by Formula (5).

(Formula 5)

$$\epsilon_r = \epsilon_{ar} \times a + \epsilon_{br} \times b \quad (5)$$

Because the mixture liquid is constructed by two kinds components that are alcohol and gasoline, a sum of the mixture ratio a, b is equal to one, such that a relationship a+b=1 is defined. The mixture ratio a, b is defined in Formula (6A), (6B) by using Formula (5) and the relationship a+b=1.

(Formula 6)

$$a = (\epsilon_r - \epsilon_{br})/(\epsilon_{ar} - \epsilon_{br}) \quad (6A)$$

$$b = (\epsilon_{ar} - \epsilon_r)/(\epsilon_{ar} - \epsilon_{br}) \quad (6B)$$

Therefore, when the corrected relative permittivity $\epsilon_r$ and the relative permittivities $\epsilon_{ar}$, $\epsilon_{br}$ obtained from the memory 270 are incorporated into Formula (6A), (6B), the mixture ratio a, b can be calculated.

Next, operations and advantages of the mixture ratio calculating device 200 and the mixture ratio calculating method will be described. As described above, in the device 200, the regression line between the capacitance and the Permittivity is calculated, and a value of the permittivity is calculated based on the regression line by assigning zero in the capacitance. Thus, the mixture ratio calculating device 200 calculates the corrected relative permittivity $\epsilon_r$ of the mixture liquid. Therefore, when the mixture ratio is calculated based on the relative permittivity $\epsilon_r$, the detection accuracy of the mixture ratio can be restricted from decreasing, because the influence of the contaminant is eliminated in the relative permittivity $\epsilon_r$.

In this embodiment, the mixture ratio calculating device 200 and the mixture ratio calculating method are used for calculating the mixture ratio of the mixture liquid constructed by alcohol and gasoline. However, the device 200 and the method may be used for other fluid other than the mixture liquid.

In this embodiment, the relative permittivity $\epsilon_r$ is calculated so as to eliminate the influence of the contaminant, when the permittivity of the foreign object contained in the mixture liquid is higher than the permittivity of the mixture liquid. Alternatively, the relative permittivity $\epsilon_r$ can be calculated so as to eliminate the influence of the contaminant, even when the permittivity of the foreign object contained in the mixture liquid is lower than the permittivity of the mixture liquid. In this case, the error factor $\alpha$ of the relative permittivity has a negative value, thereby the error factor $\beta$ also has a negative value, because the error factor $\beta$ is proportional to the error factor $\alpha$. Further, in the case that the error factors $\alpha$, $\beta$ have the negative values, as the capacitance is increased (as the electrode interval becomes narrower), a ratio of the foreign object to the electrode interval is increased. Therefore, the values of the error factors $\alpha$, $\beta$ become large. Thus, in the case that the permittivity of the foreign object is lower than the permittivity of the mixture liquid, the regression line calculated between the relative permittivity and the capacitance becomes a rightward decreasing line. A cross point between the rightward decreasing regression line and the vertical axis (the relative permittivity) represents a relative permittivity to be obtained when the ratio of the foreign object to the electrode interval is the lowest. That is, the cross point represents the relative permittivity when the influence of the contaminant is the smallest. Thus, a value of the cross point between the calculated regression line and the vertical axis corresponds to the relative permittivity $\epsilon_r$ of the mixture liquid in which the influence of the contaminant is eliminated. That is, when the capacitance is zero, a value of the relative permittivity in the regression line corresponds to the relative permittivity $\epsilon_r$ of the mixture liquid in which the influence of the contaminant is eliminated. Thus, in the case that the permittivity of the foreign object is lower than the permittivity of the mixture liquid, the relative permittivity $\epsilon_r$ of the mixture liquid can be calculated by calculating the cross point between the calculated regression line and the vertical axis.

In this embodiment, the capacitances of the capacitors $C_{12}$, $C_{23}$, $C_{34}$ are different from each other, due to the different electrode intervals. Alternatively, the capacitances of the capacitors $C_{12}, C_{23}, C_{34}$ may be different from each other, due to the different opposing areas between electrodes. In this case, as the opposing area becomes smaller (as the capacitance becomes smaller), the ratio of the foreign object to the electrode interval is increased. Therefore, the relative permittivity calculated by assigning zero in the capacitance of the regression line corresponds to a relative permittivity in which the influence of the contaminant is the largest. The relative permittivity $\epsilon_r$ of the mixture liquid cannot be calculated based on the regression line. However, in the case that the capacitances of the capacitors $C_{12}, C_{23}, C_{34}$ are different from each other, due to the different opposing areas between electrodes, the relative permittivity $\epsilon_r$ of the mixture liquid can be calculated by calculating a regression line relative to the relative permittivity and a reciprocal of the capacitance. In this regression line, as the opposing area is increased (as the capacitance is increased), the reciprocal of the capacitance becomes smaller, and the ratio of, the foreign object to the electrode interval is decreased. Therefore, a cross point between the regression line and the vertical axis (relative permittivity) is a relative permittivity to be obtained when the capacitance is infinite (when the opposing area is infinite). That is, the cross point represents a relative permittivity when the ratio of the foreign object to the opposing area is the lowest. Further, the cross point represents a relative permittivity when the influence of the contaminant is the smallest. Thus, a value of the cross point between the calculated regression line and the vertical axis corresponds to the relative permittivity $\epsilon_r$ of the mixture liquid in which the influence of the contaminant is eliminated. That is, when the reciprocal of the capacitance is zero (when the capacitance and the opposing area are infinite), the relative permittivity in the regression line corresponds to the relative permittivity $\epsilon_r$ of the mixture liquid. Thus, in the case that the capacitances of the capacitors $C_{12}, C_{23}, C_{34}$ are different from each other, due to the different opposing areas between electrodes, the corrected relative permittivity $\epsilon_r$ can be calculated by calculating a regression line relative to the relative permittivity and the reciprocal of the capacitance and by assigning zero in the reciprocal of the capacitance in the regression line.

In this embodiment, the second calculating process is performed after the first calculating process is finished. Alternatively, a comparing process may be performed between the first calculating process and the second calculating process so as to compare the three calculated relative permittivities. When two of the calculated relative permittivities do not include an error factor, a difference between the two relative permittivities is zero. Therefore, the contaminant-free relative permittivity can be calculated by finding the two relative permittivities between which the difference of two relative permittivities becomes zero. Thus, when two of the relative permittivities not affected by the contaminant are detected, the second and third calculating processes can be omitted. Therefore, a process speed of the calculating portion 230 can be made fast.

In this embodiment, the electrode 211-214 has a rectangular cross-section. However, the electrode 211-214 is not limited to have the rectangular cross-section. The electrode 211-214 may have a comb-teeth shape, for example. Therefore, even when a size of the electrode is small, sufficient opposing area can be obtained between the electrodes. Thus, a size of the mixture ratio calculating device 200 can be made small.

In this embodiment, the sensor portion 210 has the four electrodes 211-214. However, the sensor portion 210 is not limited to have the four electrodes 211-214. Alternatively, the sensor portion 210 may have four or more electrodes. For example, the sensor portion 210 may have five electrodes. In this case, four capacitors are defined.

(28th Embodiment)

A mixture fluid concentrations detecting method detects concentrations of components of mixture fluid, and the mixture fluid is constructed by N (integer≥3) kinds of known components. Permittivities of the mixture fluid are measured at different temperatures of (N-1) points, and the concentrations of the components are calculated based on known permittivies of the components at the different temperatures of (N-1) points and the measured permittivities of the mixture fluid at the different temperatures of (N-1) points.

The concentrations of the components are detected by using a difference between the permittivies of the components and a difference between the temperature characteristics of the permittivities. When the concentrations (existing ratio) of the components are defined as $a_1, a_2, \ldots, a_N$, an equality of $a_1+a_2+\ldots+a_N=1$ is defined. Further, when the permittivities of the mixture fluid are measured at the different temperatures of (N-1) points, the permittivities $\epsilon_1, \epsilon_2, \ldots, \epsilon_{N-1}$ of (N-1) are obtained. The measured permittivity $\epsilon_1, \epsilon_2, \ldots, \epsilon_{N-1}$ is equal to a sum of multiplications between the known permittivity of the component and the concentration of the component at the same temperature. Therefore, the equalities of (N-1) can be defined. Thus, according to the concentration detecting method for the mixture fluid, simultaneous equation constructed by the equalities of N can be defined relative to unknowns of N of the concentrations $a_1, a_2, \ldots, a_N$. The concentrations $a_1, a_2, \ldots, a_N$ can be properly determined by solving the simultaneous equation.

Thus, the concentration detecting method detects the concentrations of the components of the mixture fluid constructed by N (integer≥3) kinds of known components. The method can properly detect the concentrations of the mixture fluid containing three or more components.

For example, in the above method, when the N is equal to 3, the mixture fluid is defined to contain three components A, B, C. For example, the component C is mixed in a mixture fluid containing the components A, B as an impurity. The components A, B, C are uniformly mixed without chemical reactions.

In the above method, the concentrations of the components are detected in the following procedure. When the mixture fluid contains the three components A, B, C, two different temperatures are set, and each the permittivities of the single component A, B, C, at the set temperatures is obtained in advance. Next, the permittivies of the mixture fluid are measured at the set temperatures.

The components A, B, C are defined to have concentrations a1, a2, a3, respectively. The two different temperatures are defined to be $T_1, T_2$, respectively. The components A, B, C are defined to have permittivities $\epsilon_{a1}, \epsilon_{b1}, \epsilon_{c1}$ at the temperature $T_1$, respectively. The components A, B, C are defined to have permittivies $\epsilon_{a2}, \epsilon_{b2}, \epsilon_{c2}$ at the temperature $T_2$, respectively. The mixture fluid is defined to have permittivies $\epsilon_1, \epsilon_2$ at the temperatures $T_1, T_2$, respectively. In this case, the following formulas are defined.

$$a1+a2+a3=1 \quad \text{(Formula A)}$$

$$\epsilon_1 = \epsilon_{a1} \cdot a1 + \epsilon_{b1} \cdot a2 + \epsilon_{c1} \cdot a3 \quad \text{(Formula B)}$$

$$\epsilon_2 = \epsilon_{a2} \cdot a1 + \epsilon_{b2} \cdot a2 + \epsilon_{c2} \cdot a3 \quad \text{(Formula C)}$$

The concentrations a1, a2, a3 of the components A, B, C can be calculated by solving the above simultaneous equation.

The above method is suitable for detecting concentrations of mixture fuel for an internal combustion engine in which water has a possibility to be mixed. For example, when bio-mixed-gasoline includes gasoline and ethanol as a main component, the components are ethanol, gasoline and water. Because gasoline contains hundreds of components having approximately the same permittivity, the gasoline can be defined as a single component. Further, when bio-mixed light oil includes light oil and fatty acid methyl ester as a main component, the components are fatty acid methyl ester, light oil and water.

Next, the concentration detecting method will be specifically described with reference to drawings.

Figure 42:
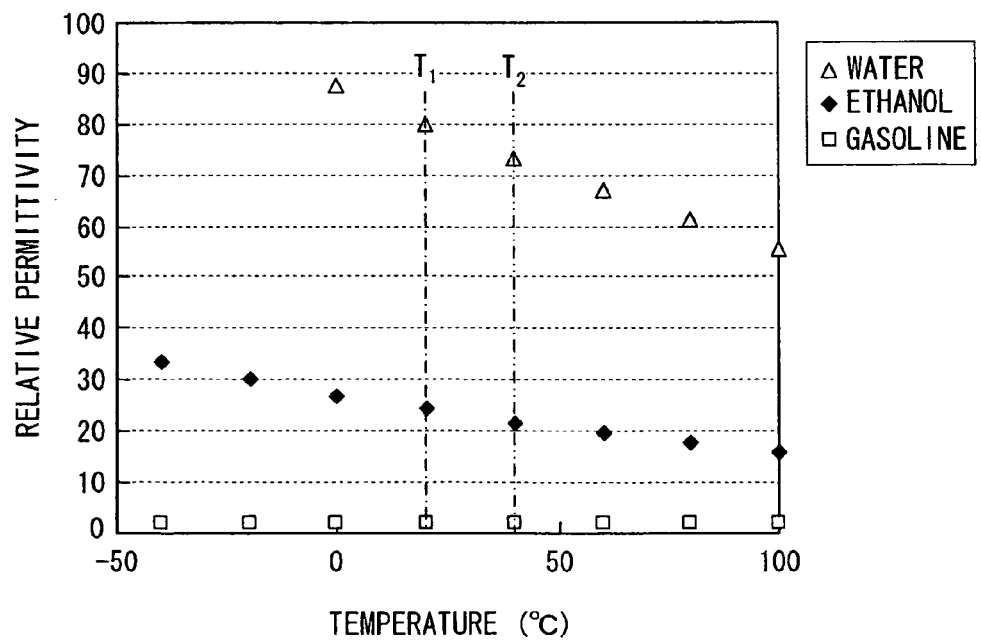
FIG. 42 is a graph illustrating temperature characteristics of relative permittivity as for ethanol, gasoline and water.

FIG. 42 shows temperature characteristics of a relative permittivity as for ethanol, gasoline and water.

Like the bio-mixed-gasoline, when a main component (gasoline, ethanol) and an impurity (water) are known, as shown in FIG. 42, temperature dependencies of the permittivities of the components are obtained in advance. Thus, as for ethanol, gasoline and water, the permittivies $\epsilon_{a1}, \epsilon_{b1}, \epsilon_{c1}$ at the temperature $T_1$, and the permittivies $\epsilon_{a2}, \epsilon_{b2}, \epsilon_{c2}$ at the temperature $T_2$ are obtained in advance. The temperature $T_1$, $T_2$ is not necessary for matching the measured temperatures of data of FIG. 42. The data are stored in a memory to be described below. The temperatures $T_1$, $T_2$ can be arbitrarily set by using a linear interpolation, and used for calculating Formulas A-C.

Figure 43:
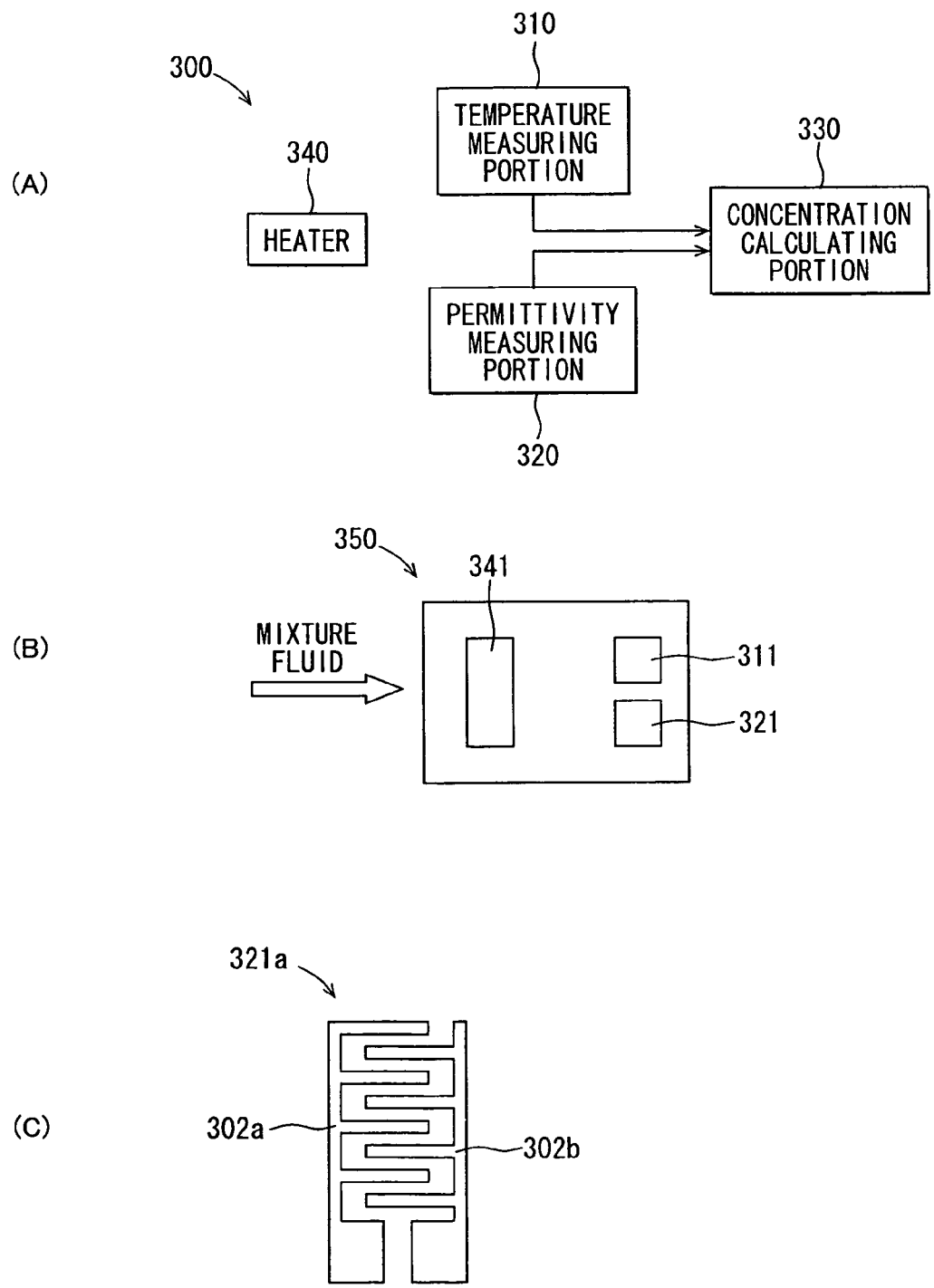
FIG. 43(A) is a diagram illustrating a concentration detecting device according to a 28th embodiment.
FIG. 43(B) is a plan view illustrating a sensor chip of a sensor part of the concentration detecting device of FIG. 43(A)
FIG. 43(C) is a plan view illustrating a capacitance detecting element of FIG. 43(B)

FIG. 43 shows a concentration detecting device for conducting the concentration detecting method. FIG. 43(A) shows a construction of the concentration detecting device 300. FIG. 43(B) shows a plan view illustrating a sensor chip 350, as a sensor part of the device 300. FIG. 43(C) shows a plan view illustrating a capacitance detecting element 321a, as an example of a capacitance detecting element 321 of FIG. 43(B).

The device 300 of FIG. 43(A) detects concentrations of components contained in mixture fluid containing N (integer≥3) kinds of know components. The device 300 includes a temperature measuring portion 310, a permittivity measuring portion 320 and a concentration calculating portion 330. The temperature measuring portion 310 measures temperatures of the mixture fluid at different points of (N−1). The permittivity measuring portion 320 measures permittivities of the mixture fluid at the different temperatures of (N−1) points. Known permittivities of the components at the different temperatures of (N−1) points are stored in a memory (not shown). The concentration calculating portion 330 calculates concentrations of the components based on the known permittivities stored in the memory and the measured permittivities of the mixture fluid at the different temperatures of (N−1) points.

The device 300 of FIG. 43(A) further includes a heater 340 to form the different temperatures of (N−1) points. The temperature of the mixture fluid can be changed by time passage, such that the permittivities of the mixture fluid are measured at the different temperatures of (N−1) points. However, when the device 300 includes the heater 340, the temperature of the mixture fluid can be changed in a short time. Thus, the device 300 can detect the concentrations of the components.

The heater 340 of the device 300 of FIG. 43(A) emits heat so as to form the different temperatures of (N−1) points. In contrast, the different temperatures of (N−1) points may be obtained by cooling. The heating or the cooling can be directly or indirectly performed in a range in which an irreversible reaction is not generated in an object to be measured. The heating may be performed by using a resistor heating, induction heating, electromagnetic heating, radiant heating, Pertier element or expansion valve. The cooling may be performed by using refrigerant cooling, forced-convection cooling, Peter element or compression valve.

The sensor chip 350 of FIG. 43(B) is made of a semiconductor board. A temperature detecting element 311 of the temperature measuring portion 310, a capacitance detecting element 321 of the permittivity measuring portion 320, and a heater element 341 of the heater 340 are arranged on the sensor chip 350. The sensor chip 350 is immersed in the mixture fluid, and the permittivities of the mixture fluid are measured at the different temperatures of (N−1) points. The temperature detecting element 311, the capacitance detecting element 321 and the heater element 341 are formed on a single chip such as the sensor chip 350. Therefore, size reduction and cost reduction are performed compared with a case in which a temperature detecting element and a capacitance detecting element are separately arranged in a pipe through which the mixture fluid flows. When the sensor chip 350 is made of the semiconductor board, micrometer-order wiring can be formed, such that the size can be made small into several millimeters cube.

The sensor chip 350 of FIG. 43(B) is not limited to be made of the semiconductor board. Alternatively, the sensor chip 350 may be made of a ceramic board having the temperature detecting element 311, the capacitance detecting element 321 and the heater element 341. Alternatively, the heater element 341 may be a separate part (separate chip), or the temperature detecting element 311 and the capacitance detecting element 321 may be separately formed on different chips.

When the capacitance detecting element is formed on the chip, as shown in FIG. 43(C), the capacitance detecting element 321a may be made of a pair of comb-teeth electrodes 302a, 302b. Thus, the mixture fluid can be easily introduced between the comb-teeth electrodes 302a, 302b arranged on the sensor chip 350 of FIG. 43(B). Further, a value of the detected capacitance can be increased by raising comb-teeth density, such that accuracy for measuring the permittivity can be raised.

Figure 44:
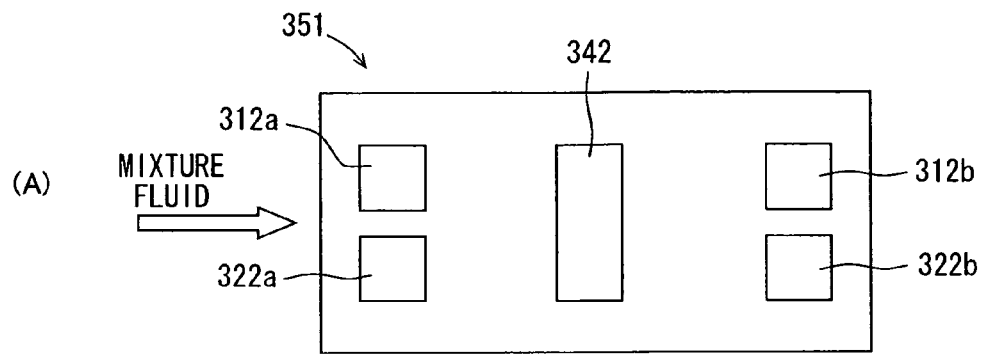
FIG. 44(A) is a plan view illustrating a sensor chip of a sensor part of the concentration detecting device.
FIG. 44(B) is a graph illustrating temperature distribution of the sensor chip in a flowing direction of mixture fluid.
FIG. 44(C) is a schematic cross-sectional view illustrating the sensor chip along the flowing direction of mixture fluid.
Figure 44:
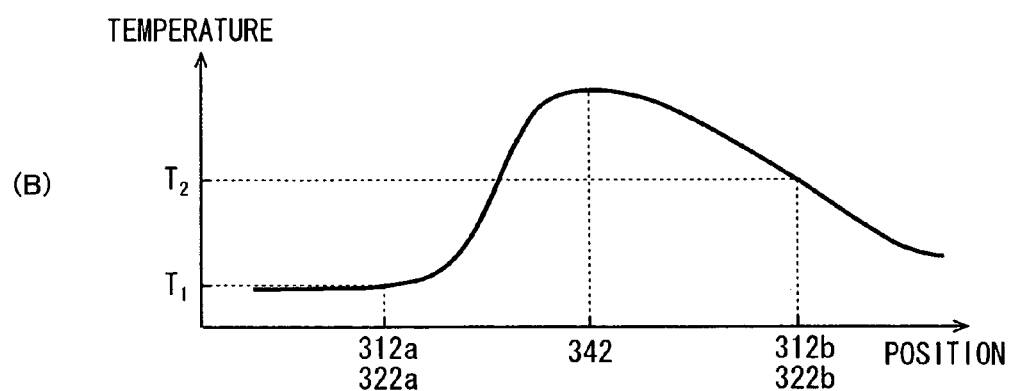
Figure 44:
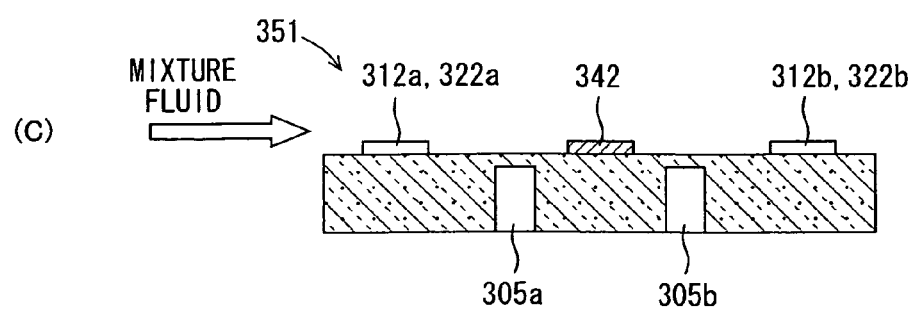

FIG. 44 shows another example of the sensor part of the device 300 of FIG. 43(A). FIG. 44(A) shows a plan view illustrating a sensor chip 351. FIG. 44(B) shows temperature distribution of the sensor chip 351 in a flowing direction of the mixture fluid. FIG. 44(C) shows a cross-sectional view illustrating the sensor chip 351 along the flowing direction of the mixture fluid.

As shown in FIG. 44(A), a heater element 342 is arranged on a center position of the sensor chip 351 in the flowing direction of the mixture fluid. A temperature detecting element 312a and a capacitance detecting element 322a are arranged at an upstream side of the heater element 342, and a temperature detecting element 312b and a capacitance detecting element 322b are arranged at a downstream side of the heater element 342. As shown in FIG. 44(B), permittivities of the mixture fluid at the different temperatures $T_1$, $T_2$ can be measured at the same time, by using the heater element 342.

As shown in FIG. 44(C), when the heater is arranged on the sensor chip, the sensor chip 351 may have a groove 305a, 305b to thermally separate the heater element 342 from the elements 312a, 312b, 322a, 322b. Thus, heat can be restricted from conducting from the heater element 342 to the elements 312a, 312b, 322a, 322b through the chip. In this case, the temperature and the permittivity can be properly measured, compared with a case in which the groove 305a, 305b is not defined in the sensor chip 351. Therefore, the concentrations of the components can be more accurately detected. The groove 305a, 305b is easily formed by etching, for example, in the sensor chip 351 made of the semiconductor board.

Figure 45:
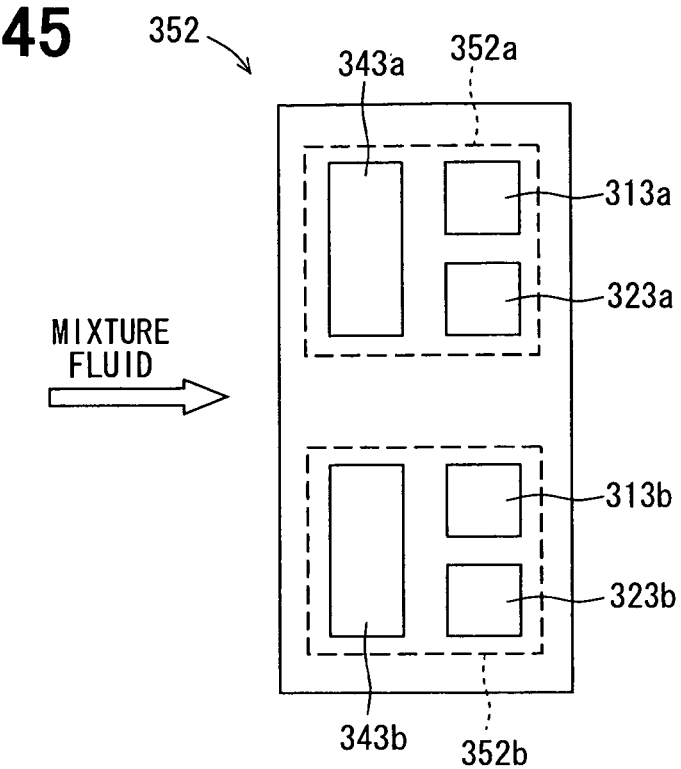
FIG. 45 is a plan view illustrating another example of the sensor chip of the concentration detecting device.

FIG. 45 shows a plan view illustrating another sensor chip 352.

A detection element 352a for the temperature $T_1$ and a detection element 352b for the temperature $T_2$ are arranged adjacent to each other on the sensor chip 352, and are located at the same position in the flowing direction of the mixture fluid. The detection element 352a defined by a broken line area of FIG. 45 is constructed by a heater element 343a, a temperature detecting element 313a and a capacitance detecting element 323a. The detection element 352b defined by a broken line area of FIG. 45 is constructed by a heater element 343b, a temperature detecting element 313b and a capacitance detecting element 323b. The sensor chip 352 may have only one of the heater elements 343a, 343b. Further, one of the detection elements 352a, 352b may be arranged on a top face of the sensor chip 352, and the other of the detection elements 352a, 352b may be arranged on a back face of the sensor chip 352.

Figure 46:
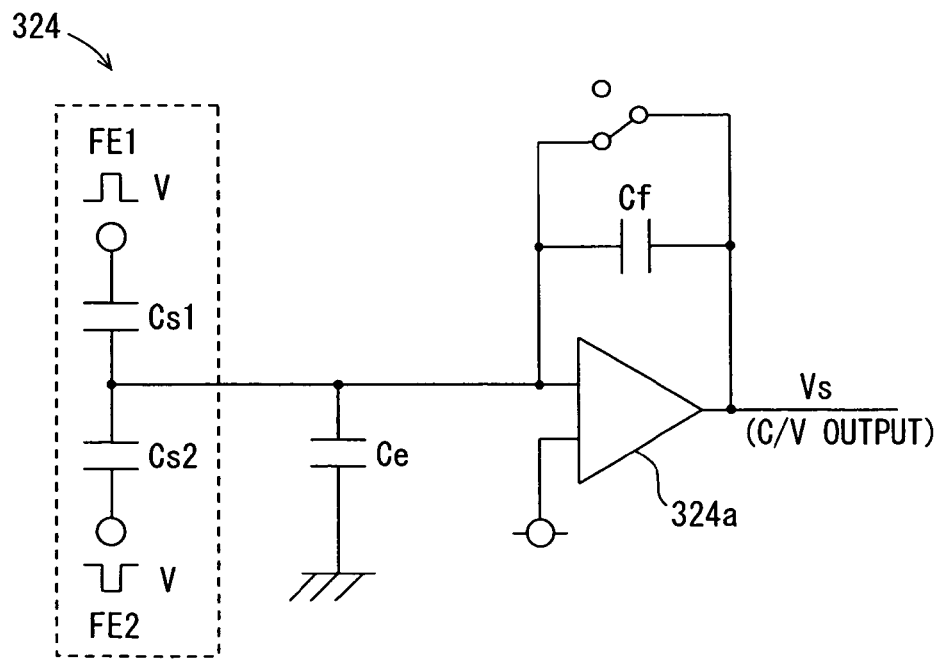
FIG. 46 is a circuit block diagram illustrating a permittivity measuring portion of the concentration detecting device.

FIG. 46 is a circuit block diagram illustrating a permittivity measuring portion 324, as an example of the permittivity measuring portion 320 of the device 300 of FIG. 43(A).

The permittivity measuring portion 324 of FIG. 46 includes two of capacitance detecting element Cs1, Cs2 connected in series with each other, and a C/V converter 324a having a feedback capacitance Cf. In the measuring of the permittivity of the mixture fluid, the capacitance detecting elements Cs1, Cs2 are driven by carrier waves FE1, FE2, respectively. The wave FE1, FE2 has a predetermined voltages V, and phases of the waves FE1, FE2 are opposite from each other. Signal output from a connection point between the capacitance detecting elements Cs1, Cs2 is input into the C/V converter 324a. At this time, the C/V converter 324a has an output voltage Vs defined by Formula D.

$$Vs = V(Cs1 - Cs2)/Cf \quad \text{(Formula D)}$$

C/V conversion is performed relative to a difference between the capacitance detecting elements Cs1, Cs2. The permittivity of the mixture fluid can be measured based on the output voltage Vs of Formula D. When the permittivity measuring portion 324 of FIG. 46 is used, influence of a parasitic capacitance Ce generated by wiring can be cancelled. Therefore, the permittivity can be more accurately measured, compared with a case in which a single capacitance detecting element is used. Thus, the concentrations of the components can be more accurately detected.

Figure 47:
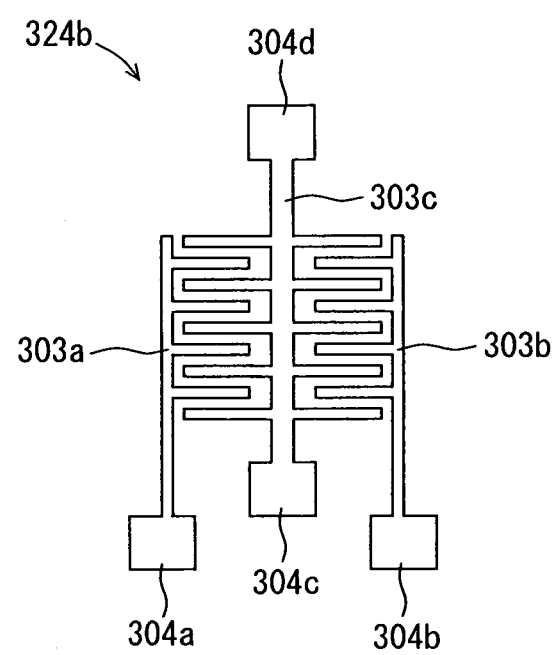
FIG. 47 is a schematic plan view illustrating two of capacitance detecting elements of FIG. 46.

FIG. 47 shows a schematic plan view illustrating a capacitance detecting element 324b, as an example of the two capacitance detecting elements Cs1, Cs2 of FIG. 46.

The capacitance detecting element 324b of FIG. 47 includes a comb-teeth electrode 303a having a pad 304a, a comb-teeth electrode 303b having a pad 304b, and a comb-teeth electrode 303c having pads 304c, 304d. The electrode 303a and the electrode 303c oppose to each other, and correspond to the capacitance detecting element Cs1 of FIG. 46. The carrier wave FE1 is input into the pad 304a. The electrode 303b and the electrode 303c oppose to each other, and correspond to the capacitance detecting element Cs2 of FIG. 46. The carrier wave FE2 is input into the pad 304b. Signal output from the pad 304c or the pad 304d is input into the C/V converter 324a of FIG. 46.

In the capacitance detecting element 324b of FIG. 47, the electrode 303c having the pads 304c, 304d may be constructed by a temperature detecting resistor so as to operate as the temperature detecting element. In a case that the capacitance detecting element of the permittivity measuring portion is made of the pair of electrodes, one of the electrodes may further operate as the temperature detecting element. Thus, size reduction and cost reduction can be achieved.

Figure 48:
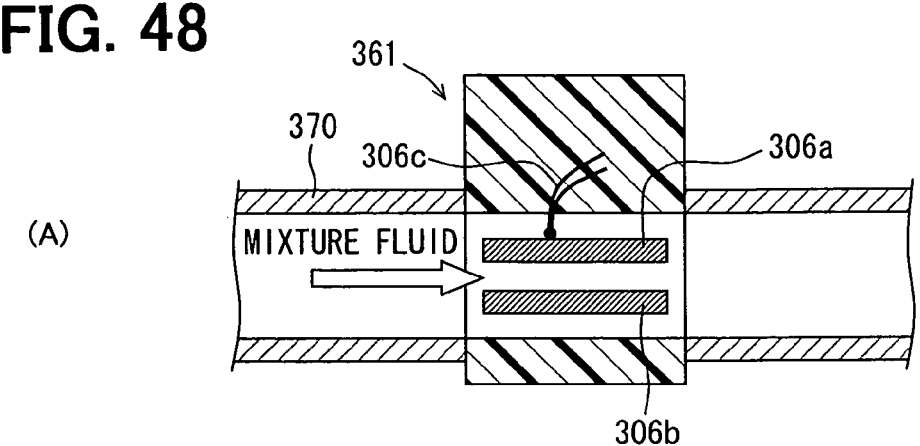
FIG. 48(A) is a schematic cross-sectional view illustrating another example of the sensor part of the concentration detecting device.
FIG. 48(B) is a schematic cross-sectional view illustrating another example of the sensor part of the concentration detecting device.

FIG. 48(A) or FIG. 48(B) shows another example of the sensor unit of the concentration detecting device 300 of FIG. 43(A). FIG. 48(A) is a schematic cross-sectional view illustrating a sensor part 361, and FIG. 48(B) is a schematic cross-sectional view illustrating a sensor part 362.

The sensor chip 350-352 of the concentration detecting device 300 of FIG. 43(A) is used by being immersed in the mixture fluid. In contrast, the sensor part 361, 362 is used by being mounted to a pipe 370. The sensor part 361 of FIG. 48(A) includes a pair of board-shaped electrodes 306a, 306b and a thermocouple 306c corresponding to the temperature detecting element. The sensor part 362 of FIG. 48(B) includes a pair of cylinder-shaped electrodes 307a, 307b, and a thermocouple 307c corresponding to the temperature detecting element.

In a case that permittivity of fuel in a vehicle is measured, a temperature of fuel passing through the pipe 370 can be changed by arranging a heater outside or inside of the pipe 370. When the sensor part 361, 362 is arranged at two positions among directly under the heater, upstream side of the heater, and downstream side of the heater, the concentrations of components can be measured without changing temperature setting of the heater of FIG. 44.

Figure 49:
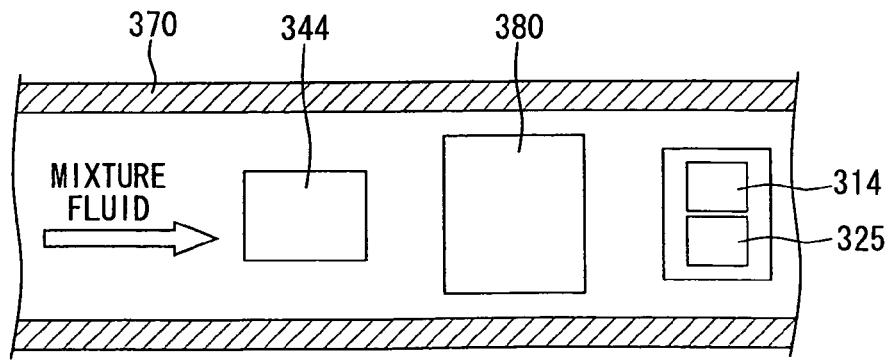
FIG. 49 is a schematic plan view illustrating a sensor chip when a capacitance detecting element having a large electrode dimension is used.

FIG. 49 shows another arrangement example, when a capacitance detecting element has a large electrode dimension like the sensor part 361, 362 of FIG. 48(A) and FIG. 48(B).

As shown in FIG. 49, an agitating portion 380 to agitate the mixture fluid is arranged between a heater element 344 and a set of a temperature detecting element 314 and a capacitance detecting element 325. The heater element 344 is arranged at an upstream side of the agitating portion 380 in a flowing direction of the mixture fluid, and the temperature detecting element 314 and the capacitance detecting element 325 are arranged at a downstream side of the agitating portion 380 in the flowing direction of the mixture fluid. The agitating portion 380 may be made of a fin, mesh or filter. Temperature variation of mixture fluid generated by using the heater element 344 can be eliminated by the agitating portion 380. Thus, the temperature and the permittivity can be properly measured. Therefore, the concentrations of the components can be more accurately measured by the arrangement of FIG. 49. Especially, when the capacitance detecting element having the large electrode dimension such as the sensor part 361,362 is used, the temperature of mixture fluid between the electrodes is required to be made uniform by using the agitating portion 380, because a volume of the mixture fluid between the electrodes is large.

By using the above sensor part, permittivities of mixture fluid containing three components A, B, C, for example, are measured at the two different temperatures. Simultaneous equation of Formula 1-3 is solved by using the concentration calculating portion 330 of FIG. 43(A). Thus, the concentrations a1, a2, a3 of the components A, B, C can be calculated. In a case that the mixture fluid contains N (integer$\geq$3) kinds components, permittivities of mixture fluid are measured at the different temperatures of (N–1) points, and Formula 1-3 are generalized. Thus, concentrations (existing ratio) of components $a_1, a_2, \ldots, a_N$ are calculated.

Thus, the concentration detecting method and the detecting device detect concentrations of components of mixture fluid containing N (integer$\geq$3) kinds known components. The concentration detecting method and the detecting device can accurately detect concentrations of mixture fluid containing three or more components.

Therefore, the method and the device can be used for detecting concentrations of mixture fuel having a possibility to accidentally contain water, when the mixture fuel is used for an internal combustion engine. For example, the components are constructed by ethanol, gasoline and water, or the components are constructed by fatty acid methyl ester, light oil and water.

Such changes and modifications are to be understood as being within the scope of the present invention as defined by the appended claims.

The invention claimed is:

1. A concentration sensor device comprising:
a sensor unit to detect a concentration of a specific component contained in liquid;
a substrate having a first face on which the sensor unit is arranged, the substrate having a second face which is opposite to the first face;
a sedimentation limit unit integrally arranged with the sensor unit or arranged at an upstream side of the sensor unit in a flowing direction of the liquid; and
an electrode portion arranged on the second face of the substrate, the electrode portion and the sensor unit sandwiching the substrate, wherein
the sensor unit has a comb-teeth shaped electrode pattern made of a first piezoelectric element made of PZT,
the electrode portion defines a potential difference between the electrode pattern and the electrode portion,
the sedimentation limit unit is configured to prevent sedimentation of a foreign object on the sensor unit,
the sedimentation limit unit includes a second piezoelectric made of PZT element to vibrate when electricity is supplied so as to promote the foreign object to be separated from the sensor unit, and
the second piezoelectric element of the sedimentation limit unit is defined by the first piezoelectric element of the electrode pattern of the sensor unit,
the comb-teeth shaped electrode pattern of the sensor unit further comprises a first comb-teeth electrode and a second comb-teeth electrode, the first and second comb-teeth electrodes have comb-teeth shapes disposed to face each other,
the sensor unit detects the concentration of the specific component contained in a mixture fuel by detecting a permittivity or a relative permittivity between the first comb-teeth electrode and the second comb-teeth electrode that face each other.

2. A concentration sensor device comprising:
a sensor unit to detect a concentration of a specific component contained in liquid;
a substrate having a first face on which the sensor unit is arranged, the substrate having a second face which is opposite to the first face; and
a sedimentation limit unit integrally arranged with the sensor unit or arranged at an upstream side of the sensor unit in a flowing direction of the liquid, wherein
the sedimentation limit unit is configured to prevent sedimentation of a foreign object on the sensor unit,
the sedimentation limit unit includes a first piezoelectric element made of PZT to vibrate when electricity is supplied so as to promote the foreign object to be separated from the sensor unit,
the sensor unit has a first comb-teeth electrode pattern made of a second piezoelectric element made of PZT,
the sedimentation limit unit is constructed by the first comb-teeth electrode pattern and a second comb-teeth electrode pattern, and
the second comb-teeth electrode pattern is made of a third piezoelectric element made of PZT and arranged on the second face of the substrate, the second comb-teeth electrode pattern and the sensor unit sandwiching the substrate,
the first comb-teeth electrode pattern of the sensor unit further comprises a first comb-teeth electrode and a second comb-teeth electrode, the first and second comb-teeth electrodes have comb-teeth shapes disposed to face each other,
the sensor unit detects the concentration of the specific component contained in a mixture fuel by detecting a permittivity or a relative permittivity between the first comb-teeth electrode and the second comb-teeth electrode that face each other.

3. A concentration sensor device comprising:
a sensor unit to detect a concentration of a specific component contained in liquid, the sensor unit having a first side and a second side which is opposite to the first side;
a substrate having a first face on which the first side of the sensor unit is arranged, the substrate having a second face which is opposite to the first face; and
a sedimentation limit unit integrally arranged with the sensor unit or arranged at an upstream side of the sensor unit in a flowing direction of the liquid, wherein
the sedimentation limit unit is configured to prevent sedimentation of a foreign object on the sensor unit,
the sedimentation limit unit includes a first piezoelectric element to made of PZT vibrate when electricity is supplied so as to promote the foreign object to be separated from the sensor unit,
the sedimentation limit unit has a first comb-teeth electrode pattern and a second comb-teeth electrode pattern,
the first comb-teeth electrode pattern is made of a second piezoelectric element made of PZT and layered on the second side of the sensor unit opposite from the substrate, and
the second comb-teeth electrode pattern is made of a third piezoelectric element made of PZT and arranged on the second face of the substrate, the second comb-teeth electrode pattern and the sensor unit sandwiching the substrate,
the sensor unit has a first comb-teeth electrode and a second comb-teeth electrode, the first and second comb-teeth electrodes have comb-teeth shapes disposed to face each other,
the sensor unit detects the concentration of the specific component contained in a mixture fuel by detecting a permittivity or a relative permittivity between the first comb-teeth electrode and the second comb-teeth electrodes that face each other.

4. A concentration sensor device comprising:
a sensor unit to detect a concentration of a specific component contained in liquid;
a sedimentation limit unit integrally arranged with the sensor unit or arranged at an upstream side of the sensor unit in a flowing direction of the liquid; and
a protection film arranged to cover the sensor unit, wherein
the protection film having a first side which is an end face and a second side opposite to the end face,
the sedimentation limit unit is arranged on the end face of the protection film, the sensor unit being arranged on the second side of the protection film, the sedimentation limit unit and the sensor unit sandwiching the protection film, and
the sedimentation limit unit is configured to prevent sedimentation of a foreign object on the sensor unit.

5. The concentration sensor device according to claim 4, wherein
the first side of the protection film has a rough face, the first side faces away from the sensor unit.

6. The concentration sensor device according to claim 4, wherein
the first side of the protection film has a convex face, the first side faces away from the sensor unit.

7. The concentration sensor device according to claim 4, wherein
the first side of the protection film has a passage formation part to define a flow of the liquid, the first side has a first end which is close to the sensor unit and a second end which is distant from the sensor unit, the passage formation part is arranged on the second end distant from the sensor unit.

8. The concentration sensor device according to claim 4, wherein
the protection film is a porous member having plural holes to allow the liquid to pass through the porous member and to limit the foreign object from passing through the porous member.

9. The concentration sensor device according to claim 8, further comprising:
a vibration providing portion to provide vibration to the porous member.

10. The concentration sensor device according to claim 4, wherein
the sensor unit has a first comb-teeth electrode and a second comb-teeth electrode, the first and second comb-teeth electrodes have comb-teeth shapes disposed to face each other,
the sensor unit detects the concentration of the specific component contained in a mixture fuel by measuring a permittivity or a relative permittivity between the first comb-teeth electrode and the second comb-teeth electrode that face each other,
the sedimentation limit unit has a piezoelectric material applied to the first comb-teeth electrode and the second comb-teeth electrode, and vibrates the sensor unit by supplying electricity to the piezoelectric material, and
a voltage pattern applied between the first comb-teeth electrode and the second comb-teeth electrode is switched between when measuring the permittivity or the relative permittivity and when making the sensor unit to vibrate.

* * * * *